US012741965B2

(12) United States Patent
Suto et al.

(10) Patent No.: US 12,741,965 B2
(45) Date of Patent: Sep. 22, 2026

(54) MODULATORS OF PROGRAMMED DEATH-LIGAND-1

(71) Applicant: SOUTHERN RESEARCH INSTITUTE, Birmingham, AL (US)

(72) Inventors: Mark J. Suto, Homewood, AL (US); Bini Mathew, Hoover, AL (US); Rebecca Boohaker, Birmingham, AL (US)

(73) Assignee: SOUTHERN RESEARCH INSTITUTE, Birmingham, AL (US)

( * ) Notice: Subject to any disclaimer, the term of this patent is extended or adjusted under 35 U.S.C. 154(b) by 492 days.

(21) Appl. No.: 18/270,450

(22) PCT Filed: Jan. 4, 2022

(86) PCT No.: PCT/US2022/011200

§ 371 (c)(1),
(2) Date: Jun. 29, 2023

(87) PCT Pub. No.: WO2022/150314

PCT Pub. Date: Jul. 14, 2022

(65) Prior Publication Data

US 2024/0010642 A1 Jan. 11, 2024

Related U.S. Application Data

(60) Provisional application No. 63/134,170, filed on Jan. 5, 2021.

(51) Int. Cl.

| | |
|---|---|
| *C07D 417/12* | (2006.01) |
| *C07C 233/81* | (2006.01) |
| *C07C 233/83* | (2006.01) |
| *C07C 237/36* | (2006.01) |
| *C07C 237/38* | (2006.01) |
| *C07D 211/66* | (2006.01) |
| *C07D 277/64* | (2006.01) |
| *C07K 5/078* | (2006.01) |

(52) U.S. Cl.

CPC .......... *C07D 417/12* (2013.01); *C07C 233/81* (2013.01); *C07C 233/83* (2013.01); *C07C 237/36* (2013.01); *C07C 237/38* (2013.01); *C07D 211/66* (2013.01); *C07D 277/64* (2013.01); *C07K 5/06139* (2013.01); *C07C 2601/02* (2017.05); *C07C 2601/04* (2017.05); *C07C 2601/08* (2017.05)

(58) Field of Classification Search

None

See application file for complete search history.

(56) References Cited

U.S. PATENT DOCUMENTS

| | | | |
|---|---|---|---|
| 5,698,710 | A | 12/1997 | Sisto et al. |
| 9,988,421 | B2 | 6/2018 | Lin et al. |
| 2019/0127420 | A1 | 5/2019 | Mathew et al. |
| 2020/0361871 | A1 | 11/2020 | Ma et al. |

FOREIGN PATENT DOCUMENTS

| | | |
|---|---|---|
| WO | 1998022494 A2 | 5/1998 |
| WO | WO 2000/041531 | 7/2000 |
| WO | WO 2003/037916 | 5/2003 |
| WO | WO 2003/051837 | 6/2003 |
| WO | WO 2007/007060 | 1/2007 |
| WO | WO 2010/133306 | 11/2010 |
| WO | WO 2020/257549 | 12/2020 |
| WO | WO 2021/113528 | 6/2021 |
| WO | WO 2021/123051 | 6/2021 |
| WO | WO 2022/150314 | 7/2022 |

OTHER PUBLICATIONS

Pimenta, Daniel C., et al. "Design of Inhibitors for Human Tissue Kallikrein Using Non-Natural Aromatic and Basic Amino Acids" Biological Chemistry. vol. 383, No. 5, May 2002, pp. 853-857. www.degruyterbrill.com, https://doi.org/10.1515/BC.2002.091. (Year: 2002).*

Guzik, Katarzyna, et al. "Development of the Inhibitors That Target the PD-1/PD-L1 Interaction—A Brief Look at Progress on Small Molecules, Peptides and Macrocycles." Molecules, vol. 24, No. 11, May 2019, p. 2071. DOI.org (Crossref), https://doi.org/10.3390/molecules24112071. (Year: 2019).*

PubChem—SID: 367702775 Deposit Date: May 25, 2018, pp. 1-5; p. 2.

(Continued)

*Primary Examiner* — Clinton A Brooks
*Assistant Examiner* — Kyle Nottingham
(74) *Attorney, Agent, or Firm* — Ballard Spahr LLP

(57) ABSTRACT

The present disclosure is concerned with substituted phenyl and heterocycloalkyl compounds for the treatment of various cancers such as, for example, sarcomas, carcinomas, hematological cancers, solid tumors, breast cancer, cervical cancer, gastrointestinal cancer, colorectal cancer, brain cancer, skin cancer, prostate cancer, ovarian cancer, bladder cancer, thyroid cancer, testicular cancer, pancreatic cancer, endometrial cancer, melanomas, gliomas, leukemias, lymphomas, chronic myeloproliferative disorders, myelodysplastic syndromes, myeloproliferative neoplasms, and plasma cell neoplasms (myelomas). This abstract is intended as a scanning tool for purposes of searching in the particular art and is not intended to be limiting of the present invention.

17 Claims, No Drawings

(56) References Cited

OTHER PUBLICATIONS

Notification of Transmittal of the International Search Report and Written Opinion issued by the United States Patent and Trademark Office dated May 13, 2022, for PCT/US2022/011200 (12 pages).
Pubchem, SID 384812607, Available Date: Jul. 20, 2019 [retrieved on Feb. 22, 2021]. Retrieved from the Internet: <URL: https://pubchem.ncbi.nlm.nih.gov/substance/384812607> entire document.
Alexander et al, J., (1988) (Acyloxy)alkyl carbamates as novel bioreversible prodrugs for amines: increased permeation through biological membranes, Med. Chem. 31, 318-22.
Almarsson O, et al. (2004) Crystal engineering of the composition of pharmaceutical phases. Do pharmaceutical co-crystals represent a new path to improved medicines? Chem Commun (Camb). (17):1889-96.
Desai PV, et al., (2012) How hydrogen bonds impact P-glycoprotein transport and permeability. Bioorg Med Chem Lett. Nov. 1;22(21):6540-8.
"Disorder"; Merriam-Webster.com, attached as a pdf, 9 pages, also available at https://www.merriam-webster.com/dictionary/disorder (last visitied Oct. 2, 2023) (Year:2023).
Dixon SM, et al., (2006) Slow-binding human serine racemase inhibitors from high-throughput screening of combinatorial libraries. J Med Chem. 49(8):2388-97.
Dixon SM, et al., (2006) Aminodeoxychorismate synthase inhibitors from one-bead one-compound combinatorial libraries: "staged" inhibitor design. J Med Chem. 49(25):7413-26.
Gensini, Martina, et al., (2010) Modulation on C- and N-Terminal Moieties of a Series of Potent and Selective Linear Tachykinin NK2 Receptor Antagonists ChemMedChem. Jan.;5(1):65-78.
Sampaio-Dias IE, et al., (2019) Synthesis, Pharmacological, and Biological Evaluation of MIF-1 Picolinoyl Peptidomimetics as Positive Allosteric Modulators of D2R. ACS Chem Neurosci. 10(8):3690-3702.
Ziebart et al., (2010) Targeting multiple chorismate-utilizing enzymes with a single inhibitor: validation of a three-stage design. J Med Chem. 53(9):3718-29.

* cited by examiner

MODULATORS OF PROGRAMMED DEATH-LIGAND-1

CROSS-REFERENCE TO RELATED APPLICATIONS

This Application is a national stage filing under 35 U.S.C. § 371 of International Application No. PCT/US2022/011200, filed on Jan. 4, 2022, which claims the benefit of U.S. Provisional Application No. 63/134,170, filed on Jan. 5, 2021, the contents of which are incorporated herein by reference in their entireties.

BACKGROUND

Programmed Cell Death-1 (PD-1) is a cell surface protein important in the regulation of the immune system, specifically involving T-cells, which promote immune tolerance to self-antigens. The interaction between this surface receptor and its predominant ligand, 1 (PDL-1), has emerged as a prime therapeutic target for overcoming the tumor survival mechanism known as immune evasion. A critical barrier to therapeutic success with large biologics, such as checkpoint antibodies, is that the efficacy in solid tumors is limited, partially due to poor tumor penetrance, and the solution to this lies within the adaptability of small molecule design. Expression of PDL-1 on cells within the tumor microenvironment, thereby engaging the PD-1 checkpoint pathway, masks cancerous cells to the tumor infiltrating $CD8^+$ cytotoxic T-lymphocytes (CTLs). This is significant in that CTLs are rendered inactive towards cancerous cells, subsequently triggering exhaustion, and eventual cell death. Moreover, high PDL-1 expression on tumor cells is linked to poor prognosis, and is an indicator of tumor-induced immune evasion. It has been demonstrated that intravenous (i.v.) administration of an antibody-based checkpoint inhibitor is sufficient to disrupt this downregulating checkpoint interaction, negating the effect of PDL-1 expression, and restoring CTL anti-tumor activity. Specifically, the use of therapeutic antibodies against PD-1 have been reported to have a response rate of 19% in patients with advanced triple negative breast cancer when the tumor expresses PDL-1, and a 46% response rate when provided as combination therapy with paclitaxel, a chemotherapeutic agent, in patients who do not have high levels of PDL-1. However, such antibody therapies, while showing some efficacy in metastatic disease, have several disadvantages, including adverse side effects (e.g., colitis, endocrinopathies, and inflammatory arthritis), high dosage requirements, and the need for intravenous administration. Thus, there remains a need for compounds and compositions for modulating PDL-1 and methods of making and using same in the treatment of, for example, cancer.

SUMMARY

In accordance with the purpose(s) of the invention, as embodied and broadly described herein, the invention, in one aspect, relates to compounds and compositions for use in the prevention and treatment of disorders of uncontrolled cellular proliferation such as, for example, cancers including, but not limited to, sarcomas, carcinomas, hematological cancers, solid tumors, breast cancer, cervical cancer, gastrointestinal cancer, colorectal cancer, brain cancer, skin cancer, prostate cancer, ovarian cancer, bladder cancer, thyroid cancer, testicular cancer, pancreatic cancer, endometrial cancer, melanomas, gliomas, leukemias, lymphomas, chronic myeloproliferative disorders, myelodysplastic syndromes, myeloproliferative neoplasms, and plasma cell neoplasms (myelomas).

Thus, disclosed are compounds having a structure represented by a formula selected from:

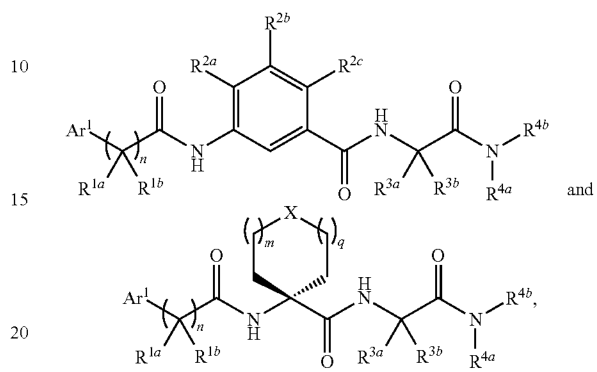

wherein each of n, m, and q, when present, is independently selected from 0 and 1; wherein X, when present, is selected from —O—, —S—, and —$NR^{10}$—; wherein $R^{10}$, when present, is selected from hydrogen and C1-C4 alkyl; wherein each of $R^{1a}$ and $R^{1b}$, when present, is independently selected from hydrogen, halogen, and C1-C4 alkyl; or wherein each of $R^{1a}$ and $R^{1b}$, when present, together comprise a C3-C6 cycloalkyl; wherein each of $R^{2a}$, $R^{2b}$, and $R^{2c}$, when present, is independently selected from hydrogen, halogen, and —$CH_2NR^{11a}R^{11b}$, provided that at least one of $R^{2a}$, $R^{2b}$, and $R^{2c}$ is —$CH_2NR^{11a}R^{11b}$; wherein each of $R^{11a}$ and $R^{11b}$, when present, is independently selected from hydrogen and C1-C4 alkyl; wherein each of $R^{3a}$ and $R^{3b}$ is independently selected from hydrogen and C1-C4 alkyl, or wherein each of $R^{3a}$ and $R^{3b}$ together comprise a C3-C6 cycloalkyl; wherein each of $R^{4a}$ and $R^{4b}$ is independently selected from hydrogen and C1-C4 alkyl; and wherein $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

Also disclosed are pharmaceutical compositions comprising an effective amount of a disclosed compound, and a pharmaceutically acceptable carrier.

Also disclosed are methods for treating a disorder of uncontrolled cellular proliferation in a subject, the method comprising administering to the subject an effective amount of a compound having a structure represented by a formula selected from:

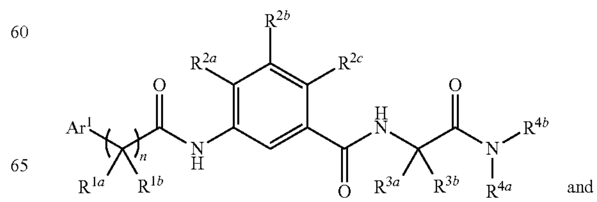

-continued

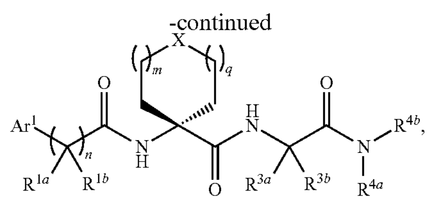

wherein each of n, m, and q, when present, is independently selected from 0 and 1; wherein X, when present, is selected from —O—, —S—, —$NR^{10}$—, and —$CR^{12a}R^{12b}$; wherein $R^{10}$, when present, is selected from hydrogen and C1-C4 alkyl; wherein each of $R^{12a}$ and $R^{12b}$, when present, is independently selected from hydrogen and C1-C4 alkyl; wherein each of $R^{1a}$ and $R^{1b}$, when present, is independently selected from hydrogen, halogen, and C1-C4 alkyl; or wherein each of $R^{1a}$ and $R^{1b}$, when present, together comprise a C3-C6 cycloalkyl; wherein each of $R^{2a}$, $R^{2b}$, and $R^{2c}$, when present, is independently selected from hydrogen, halogen, and —$CH_2NR^{11a}R^{11b}$, provided that at least one of $R^{2a}$, $R^{2b}$, and $R^{2c}$ is —$CH_2NR^{11a}R^{11b}$; wherein each of $R^{11a}$ and $R^{11b}$, when present, is independently selected from hydrogen and C1-C4 alkyl; wherein each of $R^{3a}$ and $R^{3b}$ is independently selected from hydrogen and C1-C4 alkyl, or wherein each of $R^{3a}$ and $R^{3b}$ together comprise a C3-C6 cycloalkyl; wherein each of $R^{4a}$ and $R^{4b}$ is independently selected from hydrogen and C1-C4 alkyl; and wherein $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that when X is —$CR^{12a}R^{12b}$, then each of m and q is 1, or a pharmaceutically acceptable salt thereof.

Also disclosed are methods for modifying programmed death-ligand-1 (PDL-1) signaling in a subject, the method comprising administering to the subject an effective amount of a compound having a structure represented by a formula selected from:

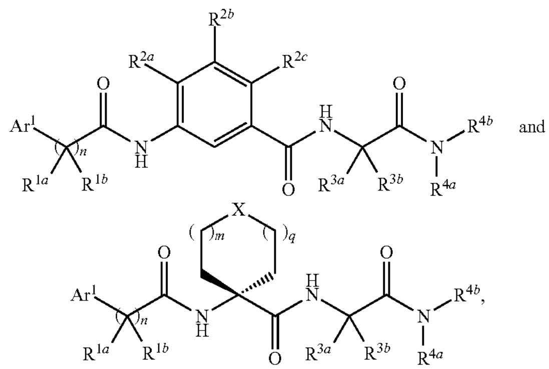

wherein each of n, m, and q, when present, is independently selected from 0 and 1; wherein X, when present, is selected from —O—, —S—, —$NR^{10}$—, and —$CR^{12a}R^{12b}$; wherein $R^{10}$, when present, is selected from hydrogen and C1-C4 alkyl; wherein each of $R^{12a}$ and $R^{12b}$, when present, is independently selected from hydrogen and C1-C4 alkyl; wherein each of $R^{1a}$ and $R^{1b}$, when present, is independently selected from hydrogen, halogen, and C1-C4 alkyl; or wherein each of $R^{1a}$ and $R^{1b}$, when present, together comprise a C3-C6 cycloalkyl; wherein each of $R^{2a}$, $R^{2b}$, and $R^{2c}$, when present, is independently selected from hydrogen, halogen, and —$CH_2NR^{11a}R^{11b}$, provided that at least one of $R^{2a}$, $R^{2b}$, and $R^{2c}$ is —$CH_2NR^{11a}R^{11b}$; wherein each of $R^{11a}$ and $R^{11b}$, when present, is independently selected from hydrogen and C1-C4 alkyl; wherein each of $R^{3a}$ and $R^{3b}$ is independently selected from hydrogen and C1-C4 alkyl, or wherein each of $R^{3a}$ and $R^{3b}$ together comprise a C3-C6 cycloalkyl; wherein each of $R^{4a}$ and $R^{4b}$ is independently selected from hydrogen and C1-C4 alkyl; and wherein $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that when X is —$CR^{12a}R^{12b}$, then each of m and q is 1, or a pharmaceutically acceptable salt thereof, thereby modifying PDL-1 signaling in the subject.

Also disclosed are methods for modifying PDL-1 signaling in a cell, the method comprising contacting the cell with an effective amount of a compound having a structure represented by a formula selected from:

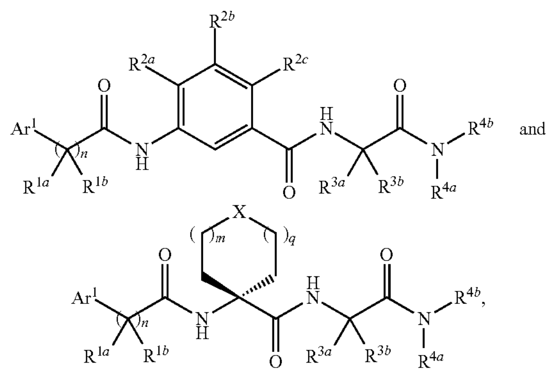

wherein each of n, m, and q, when present, is independently selected from 0 and 1; wherein X, when present, is selected from —O—, —S—, —$NR^{10}$—, and —$CR^{12a}R^{12b}$; wherein $R^{10}$, when present, is selected from hydrogen and C1-C4 alkyl; wherein each of $R^{12a}$ and $R^{12b}$, when present, is independently selected from hydrogen and C1-C4 alkyl; wherein each of $R^{1a}$ and $R^{1b}$, when present, is independently selected from hydrogen, halogen, and C1-C4 alkyl; or wherein each of $R^{1a}$ and $R^{1b}$, when present, together comprise a C3-C6 cycloalkyl; wherein each of $R^{2a}$, $R^{2b}$, and $R^{2c}$, when present, is independently selected from hydrogen, halogen, and —$CH_2NR^{11a}R^{11b}$, provided that at least one of $R^{2a}$, $R^{2b}$, and $R^{2c}$ is —$CH_2NR^{11a}R^{11b}$; wherein each of $R^{11a}$ and $R^{11b}$, when present, is independently selected from hydrogen and C1-C4 alkyl; wherein each of $R^{3a}$ and $R^{3b}$ is independently selected from hydrogen and C1-C4 alkyl, or wherein each of $R^{3a}$ and $R^{3b}$ together comprise a C3-C6 cycloalkyl; wherein each of $R^{4a}$ and $R^{4b}$ is independently selected from hydrogen and C1-C4 alkyl; and wherein $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that when X is —$CR^{12a}R^{12b}$, then each of m and q is 1, or a pharmaceutically acceptable salt thereof, thereby modifying PDL-1 signaling in the cell.

Also disclosed are kits comprising a compound having a structure represented by a formula selected from:

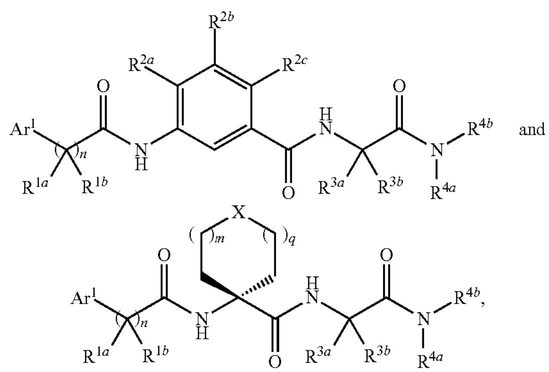

and wherein each of n, m, and q, when present, is independently selected from 0 and 1; wherein X, when present, is selected from —O—, —S—, —$NR^{10}$—, and —$CR^{12a}R^{12b}$; wherein $R^{10}$, when present, is selected from hydrogen and C1-C4 alkyl; wherein each of $R^{12a}$ and $R^{12b}$, when present, is independently selected from hydrogen and C1-C4 alkyl; wherein each of $R^{1a}$ and $R^{1b}$, when present, is independently selected from hydrogen, halogen, and C1-C4 alkyl; or wherein each of $R^{1a}$ and $R^{1b}$, when present, together comprise a C3-C6 cycloalkyl; wherein each of $R^{2a}$, $R^{2b}$, and $R^{2c}$, when present, is independently selected from hydrogen, halogen, and —$CH_2NR^{11a}R^{11b}$, provided that at least one of $R^{2a}$, $R^{2b}$, and $R^{2c}$ is —$CH_2NR^{11a}R^{11b}$; wherein each of $R^{11a}$ and $R^{11b}$, when present, is independently selected from hydrogen and C1-C4 alkyl; wherein each of $R^{3a}$ and $R^{3b}$ is independently selected from hydrogen and C1-C4 alkyl, or wherein each of $R^{3a}$ and $R^{3b}$ together comprise a C3-C6 cycloalkyl; wherein each of $R^{4a}$ and $R^{4b}$ is independently selected from hydrogen and C1-C4 alkyl; and wherein $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that when X is —$CR^{12a}R^{12b}$, then each of m and q is 1, or a pharmaceutically acceptable salt thereof, and one or more of: (a) at least one agent associated with the treatment of a disorder of uncontrolled cellular proliferation; (b) instructions for administering the compound in connection with treating a disorder of uncontrolled cellular proliferation; and (c) instructions for treating a disorder of uncontrolled cellular proliferation.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the aspects "consisting of" and "consisting essentially of."

Ranges can be expressed herein as from "about" one particular value, and/or to "about" another particular value.

When such a range is expressed, another aspect includes from the one particular value and/or to the other particular value. Similarly, when values are expressed as approximations, by use of the antecedent “about,” it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as “about” that particular value in addition to the value itself. For example, if the value “10” is disclosed, then “about 10” is also disclosed. It is also understood that each unit between two particular units are also disclosed. For example, if 10 and 15 are disclosed, then 11, 12, 13, and 14 are also disclosed.

As used herein, the terms “about” and “at or about” mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is “about” or “approximate” whether or not expressly stated to be such. It is understood that where “about” is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, “$IC_{50}$,” is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half-maximal (50%) inhibitory concentration (IC) of a substance.

As used herein, “$EC_{50}$,” is intended to refer to the concentration of a substance (e.g., a compound or a drug) that is required for 50% agonism of a biological process, or component of a process, including a protein, subunit, organelle, ribonucleoprotein, etc. In one aspect, an $EC_{50}$ can refer to the concentration of a substance that is required for 50% agonism in vivo, as further defined elsewhere herein. In a further aspect, $EC_{50}$ refers to the concentration of agonist that provokes a response halfway between the baseline and maximum response.

As used herein, the terms “optional” or “optionally” means that the subsequently described event or circumstance can or cannot occur, and that the description includes instances where said event or circumstance occurs and instances where it does not.

As used herein, the term “subject” can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term “patient” includes human and veterinary subjects.

As used herein, the term “treatment” refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term “subject” also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term “prevent” or “preventing” refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term “diagnosed” means having been subjected to a physical examination by a person of skill, for example, a physician, and found to have a condition that can be diagnosed or treated by the compounds, compositions, or methods disclosed herein.

As used herein, the terms “administering” and “administration” refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage forms can comprise inventive a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index ($14^{th}$ edition), the Physicians' Desk Reference ($64^{th}$ edition), and The Pharmacological Basis of Therapeutics ($12^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; anti-cancer and anti-neoplastic agents such as kinase inhibitors, poly ADP ribose polymerase (PARP) inhibitors and other DNA damage response modifiers, epigenetic agents such as bromodomain and extra-terminal (BET) inhibitors, histone deacetylase (HDAc) inhibitors, iron chelotors and other ribonucleotides reductase inhibitors, proteasome inhibitors and Nedd8-activating enzyme (NAE) inhibitors, mammalian target of rapamycin (mTOR) inhibitors, traditional cytotoxic agents such as paclitaxel, dox, irinotecan, and platinum compounds, immune checkpoint blockade agents such as cytotoxic T lymphocyte antigen-4 (CTLA-4) monoclonal antibody (mAB), programmed cell death protein 1 (PD-1)/programmed cell death-ligand 1 (PD-L1) mAB, cluster of differentiation 47 (CD47) mAB, toll-like receptor (TLR) agonists and other immune modifiers, cell therapeutics such as chimeric antigen receptor T-cell (CAR-T)/chimeric antigen receptor natural killer (CAR-NK) cells, and proteins such as interferons (IFNs), interleukins (ILs), and mAbs; anti-ALS agents such as entry inhibitors, fusion inhibitors, non-nucleoside reverse transcriptase inhibitors (NNRTIs), nucleoside reverse transcriptase inhibitors (NRTIs), nucleotide reverse transcriptase inhibitors, NCP7 inhibitors, protease inhibitors, and integrase inhibitors; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent (s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $—(CH_2)_a—$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $—OA^1$ where $A^1$ is alkyl or cycloalkyl as defined above. "Alkoxy" also includes polymers of alkoxy groups as just described; that is, an alkoxy can be a polyether such as $—OA^1\text{-}OA^2$ or $—OA^1\text{-}(OA^2)_a\text{-}OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C{=}C(A^3A^4)$ are intended to include both the E and Z isomers. This can be presumed in structural formulae herein wherein an asymmetric alkene is present, or it can be explicitly indicated by the bond symbol C═C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound.

Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, $—NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl can be two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C═O.

The terms "amine" or "amino" as used herein are represented by the formula $—NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is $—NH_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula $—N(\text{-alkyl})_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula $—OC(O)A^1$ or $—C(O)OA^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula $-(A^1O(O)C\text{-}A^2\text{-}C(O)O)_a—$ or $-(A^1O(O)C\text{-}A^2\text{-}OC(O))_a—$, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula $-(A^1O\text{-}A^2O)_a—$, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein can be used interchangeably and refer to F, Cl, Br, or I.

The terms "pseudohalide," "pseudohalogen," or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl", "heteroaryl", "bicyclic heterocycle" and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula $—N_3$.

The term "nitro" as used herein is represented by the formula $—NO_2$.

The term "nitrile" or "cyano" as used herein is represented by the formula —CN.

The term "silyl" as used herein is represented by the formula $-SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas $—S(O)A^1$, $—S(O)_2A^1$, $—OS(O)_2A^1$, or $—OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S═O. The term "sulfonyl" is used herein to refer to the sulfo-oxo group represented by the formula $—S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A'S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A'S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogen of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; $—(CH_2)_{0-4}R^\circ$; $—(CH_2)_{0-4}OR^\circ$; $—O(CH_2)_{0-4}R^\circ$, $—O—(CH_2)_{0-4}C(O)OR^\circ$; $—(CH_2)_{0-4}CH(OR^\circ)_2$; $—(CH_2)_{0-4}SR^\circ$; $—(CH_2)_{0-4}Ph$, which may be substituted with $R^\circ$; $—(CH_2)_{0-4}O(CH_2)_{0-1}Ph$ which may be substituted with $R^\circ$; $—CH{=}CHPh$, which may be substituted with $R^\circ$; $—(CH_2)_{0-4}O(CH_2)_{0-1}$-pyridyl which may be substituted with $R^\circ$; $—NO_2$; $—CN$; $—N_3$; $—(CH_2)_{0-4}N(R^\circ)_2$; $—(CH_2)_{0-4}N(R^\circ)C(O)R^\circ$; $—N(R^\circ)C(S)R^\circ$; $—(CH_2)_{0-4}N(R^\circ)C(O)NR^\circ_2$; $—N(R^\circ)C(S)NR^\circ_2$; $—(CH_2)_{0-4}N(R^\circ)C(O)OR^\circ$; $—N(R^\circ)N(R^\circ)C(O)R^\circ$; $—N(R^\circ)N(R^\circ)C(O)NR^\circ_2$; $—N(R^\circ)N(R^\circ)C(O)OR^\circ$; $—(CH_2)_{0-4}C(O)R^\circ$; $—C(S)R^\circ$; $—(CH_2)_{0-4}C(O)OR^\circ$; $—(CH_2)_{0-4}C(O)SR^\circ$; $—(CH_2)_{0-4}C(O)OSiR^\circ_3$; $—(CH_2)_{0-4}OC(O)R^\circ$; $—OC(O)(CH_2)_{0-4}SR—$, $SC(S)SR^\circ$; $—(CH_2)_{0-4}SC(O)R^\circ$; $—(CH_2)_{0-4}C(O)NR^\circ_2$; $—C(S)NR^\circ_2$; $—C(S)SR^\circ$; $—(CH_2)_{0-4}OC(O)NR^\circ_2$; $—C(O)N(OR^\circ)R^\circ$; $—C(O)C(O)R^\circ$; $—C(O)CH_2C(O)R^\circ$; $—C(NOR^\circ)R^\circ$; $—(CH_2)_{0-4}SSR^\circ$; $—(CH_2)_{0-4}S(O)_2R^\circ$; $—(CH_2)_{0-4}S(O)_2OR^\circ$; $—(CH_2)_{0-4}OS(O)_2R^\circ$; $—S(O)_2NR^\circ_2$; $—(CH_2)_{0-4}S(O)R^\circ$; $—N(R^\circ)S(O)_2NR^\circ_2$; $—N(R^\circ)S(O)_2R^\circ$; $—N(OR^\circ)R^\circ$; $—C(NH)NR^\circ_2$; $—P(O)_2R^\circ$; $—P(O)R^\circ_2$; $—OP(O)R^\circ_2$; $—OP(O)(OR^\circ)_2$; $SiR^\circ_3$; $—(C_{1-4}$ straight or branched alkylene)$O—N(R^\circ)_2$; or $—(C_{1-4}$ straight or branched alkylene)$C(O)O—N(R^\circ)_2$, wherein each $R^\circ$ may be substituted as defined below and is independently hydrogen, $C_{1-6}$ aliphatic, $—CH_2Ph$, $—O(CH_2)_{0-1}Ph$, $—CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $—(CH_2)_{0-2}R^\bullet$, $-(haloR^\bullet)$, $—(CH_2)_{0-2}OH$, $—(CH_2)_{0-2}OR^\bullet$, $—(CH_2)_{0-2}CH(OR^\bullet)_2$; $—O(haloR^\bullet)$, $—CN$, $—N_3$, $—(CH_2)_{0-2}C(O)R^\bullet$, $—(CH_2)_{0-2}C(O)OH$, $—(CH_2)_{0-2}C(O)OR^\bullet$, $—(CH_2)_{0-2}SR^\bullet$, $—(CH_2)_{0-2}SH$, $—(CH_2)_{0-2}NH_2$, $—(CH_2)_{0-2}NHR^\bullet$, $—(CH_2)_{0-2}NR^\bullet_2$, $—NO_2$, $—SiR^\bullet_3$, $—OSiR^\bullet_3$, $—C(O)SR^\bullet$, $—(C_{1-4}$ straight or branched alkylene)$C(O)OR^\bullet$, or $—SSR^\bullet$ wherein each $R^\bullet$ is unsubstituted or where preceded by "halo" is substituted only with one or more halogens, and is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $—O(C(R^*_2))_{2-3}O—$, or $—S(C(R^*_2))_{2-3}S—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $—O(CR^*_2)_{2-3}O—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $—R^\bullet$, $-(haloR^\bullet)$, $—OH$, $—OR^\bullet$, $—O(haloR^\bullet)$, $—CN$, $—C(O)OH$, $—C(O)OR^\bullet$, $—NH_2$, $—NHR^\bullet$, $—NR^\bullet_2$, or $—NO_2$, wherein each $R^\bullet$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $—R^\dagger$, $—NR^\dagger_2$, $—C(O)R^\dagger$, $—C(O)OR^\dagger$, $—C(O)C(O)R^\dagger$, $—C(O)CH_2C(O)R^\dagger$, $—S(O)_2R^\dagger$, $—S(O)_2NR^\dagger_2$, $—C(S)NR^\dagger_2$, $—C(NH)NR^\dagger_2$, or $—N(R^\dagger)S(O)_2R^\dagger$; wherein each $R^\dagger$ is independently hydrogen, $C_{1-6}$ aliphatic which may be substituted as defined below, unsubstituted $—OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $—R^\bullet$, $-(haloR^\bullet)$, $—OH$, $—OR^\bullet$, $—O(haloR^\bullet)$, $—CN$, $—C(O)OH$, $—C(O)OR^\bullet$, $—NH_2$, $—NHR^\bullet$, $—NR^\bullet_2$, or $—NO_2$, wherein each $R^\bullet$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

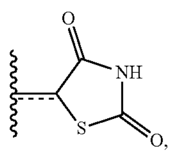

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and 1 or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (e.e.). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

The compounds according to this disclosure may form prodrugs at hydroxyl or amino functionalities using alkoxy, amino acids, etc., groups as the prodrug forming moieties. For instance, the hydroxymethyl position may form mono-, di- or triphosphates and again these phosphates can form prodrugs. Preparations of such prodrug derivatives are discussed in various literature sources (examples are: Alexander et al., J. Med. Chem. 1988, 31, 318; Aligas-Martin et al., PCT WO 2000/041531, p. 30). The nitrogen function converted in preparing these derivatives is one (or more) of the nitrogen atoms of a compound of the disclosure.

"Derivatives" of the compounds disclosed herein are pharmaceutically acceptable salts, prodrugs, deuterated forms, radio-actively labeled forms, isomers, solvates and combinations thereof. The "combinations" mentioned in this context are refer to derivatives falling within at least two of the groups: pharmaceutically acceptable salts, prodrugs, deuterated forms, radio-actively labeled forms, isomers, and solvates. Examples of radio-actively labeled forms include compounds labeled with tritium, phosphorous-32, iodine-129, carbon-11, fluorine-18, and the like.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

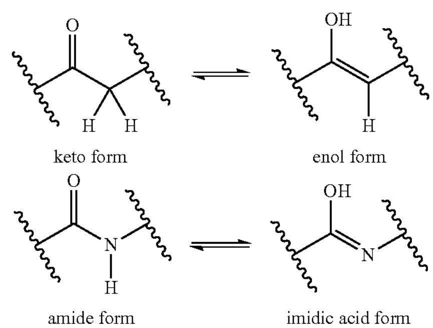

keto form enol form amide form imidic acid form

Likewise, amides with an N-hydrogen can exist in an equilibrium of the amide form and the imidic acid form. As another example, pyrazoles can exist in two tautomeric forms, $N^1$-unsubstituted, 3-$A^3$ and $N^1$-unsubstituted, 5-$A^3$ as shown below.

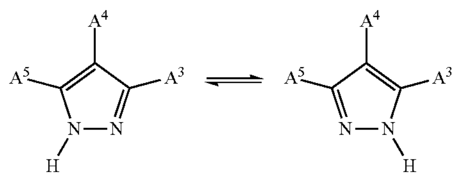

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

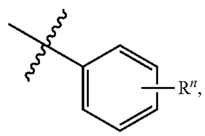

which is understood to be equivalent to a formula:

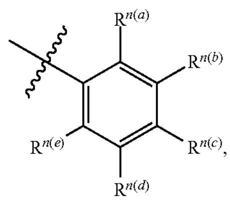

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Strem Chemicals (Newburyport, MA), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B—F, C-D, C-E, and C—F are considered disclosed. Likewise, any subset or combination of these is also disclosed. Thus, for example, the sub-group of A-E, B—F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compounds and compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds useful in treating disorders associated with a disorder of uncontrolled cellular proliferation such as, for example, cancers including, but not limited to, sarcomas, carcinomas, hematological cancers, solid tumors, breast cancer, cervical cancer, gastrointestinal cancer, colorectal cancer, brain cancer, skin cancer, prostate cancer, ovarian cancer, bladder cancer, thyroid cancer, testicular cancer, pancreatic cancer, endometrial cancer, melanomas, gliomas, leukemias, lymphomas, chronic myeloproliferative disorders, myelodysplastic syndromes, myeloproliferative neoplasms, and plasma cell neoplasms (myelomas).

In one aspect, the compounds of the invention are useful in the treatment of disorders of uncontrolled cellular proliferation, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula selected from:

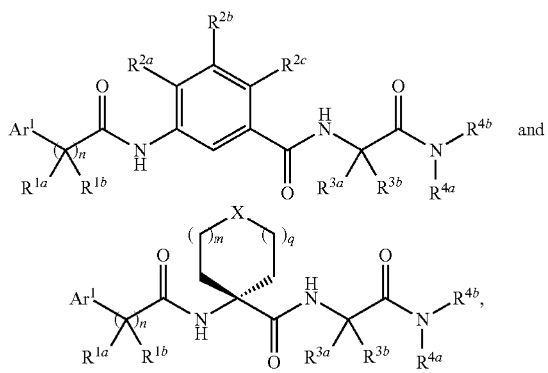

wherein each of n, m, and q, when present, is independently selected from 0 and 1; wherein X, when present, is selected from —O—, —S—, and —$NR^{10}$—; wherein $R^{10}$, when present, is selected from hydrogen and C1-C4 alkyl; wherein each of $R^{1a}$ and $R^{1b}$, when present, is independently selected from hydrogen, halogen, and C1-C4 alkyl; or wherein each of $R^{1a}$ and $R^{1b}$, when present, together comprise a C3-C6 cycloalkyl; wherein each of $R^{2a}$, $R^{2b}$, and $R^{2c}$, when present, is independently selected from hydrogen, halogen, and —$CH_2NR^{11a}R^{11b}$, provided that at least one of $R^{2a}$, $R^{2b}$, and $R^{2c}$ is —$CH_2NR^{11a}R^{11b}$; wherein each of $R^{11a}$ and $R^{11b}$, when present, is independently selected from hydrogen and C1-C4 alkyl; wherein each of $R^{3a}$ and $R^{3b}$ is independently selected from hydrogen and C1-C4 alkyl, or wherein each of $R^{3a}$ and $R^{3b}$ together comprise a C3-C6 cycloalkyl; wherein each of $R^{4a}$ and $R^{4b}$ is independently selected from hydrogen and C1-C4 alkyl; and wherein $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

In various aspects, the compound has a structure represented by a formula:

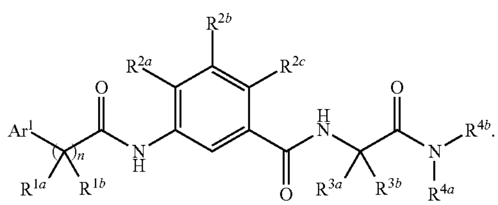

In various aspects, the compound has a structure represented by a formula:

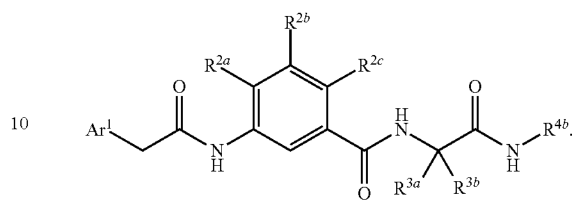

In various aspects, the compound has a structure represented by a formula:

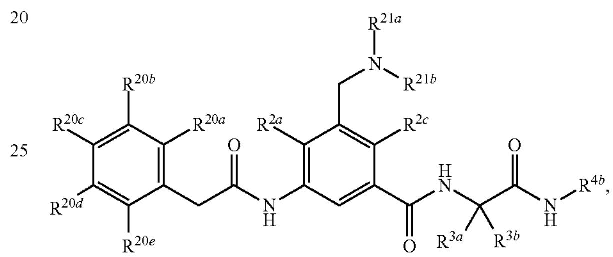

wherein each of $R^{20a}$, $R^{20b}$, $R^{20c}$, $R^{20d}$, and $R^{20e}$, is independently selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{21a}$ and $R^{21b}$ is independently selected from hydrogen and C1-C4 alkyl.

In various aspects, the compound has a structure represented by a formula:

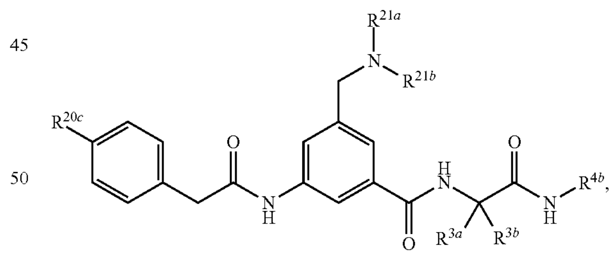

In various aspects, the compound is selected from:

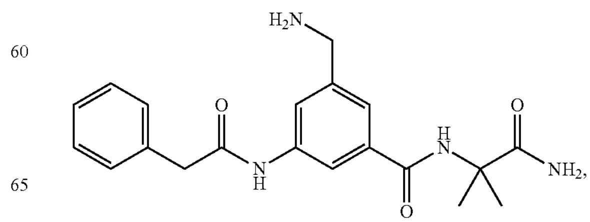

-continued
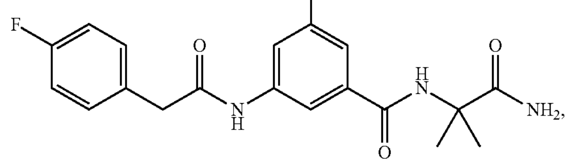
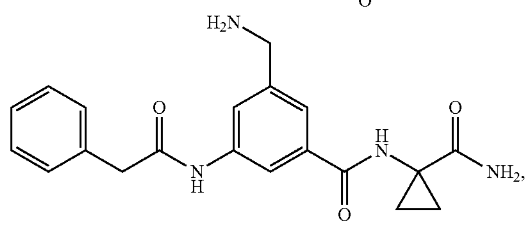
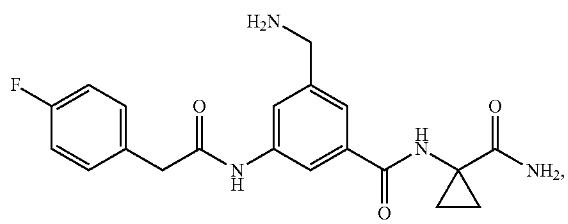
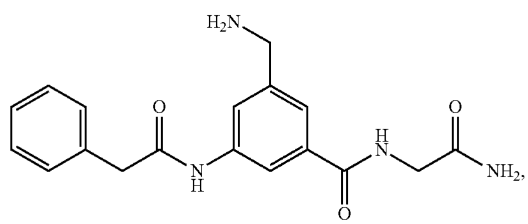
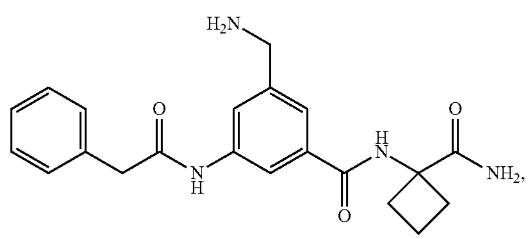
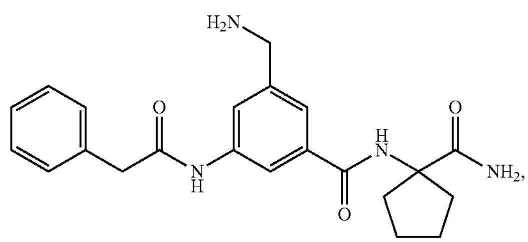
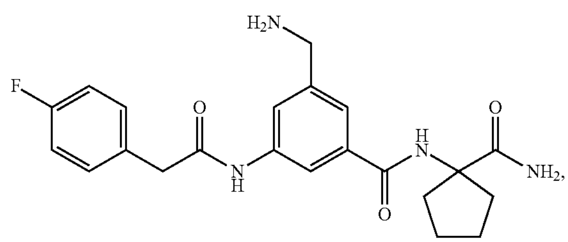
-continued
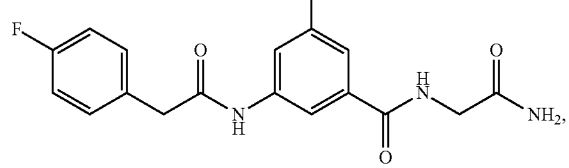
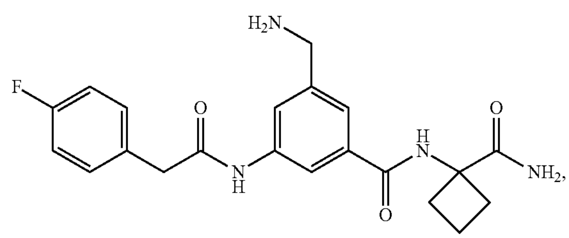
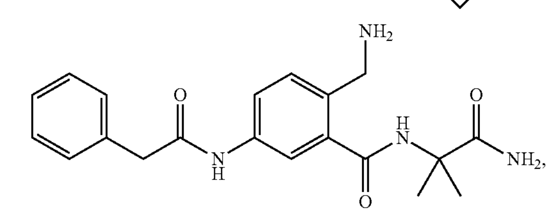
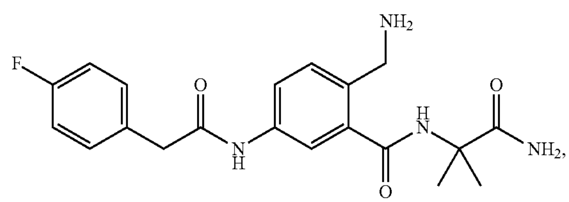
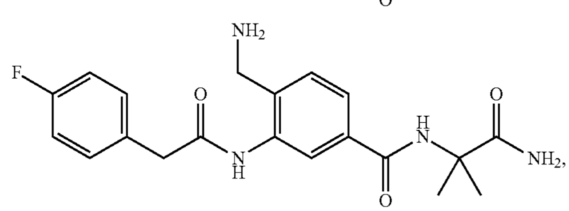
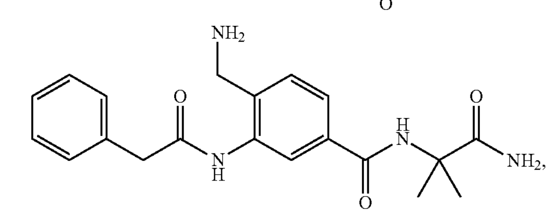
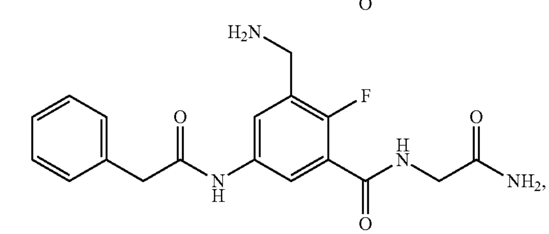
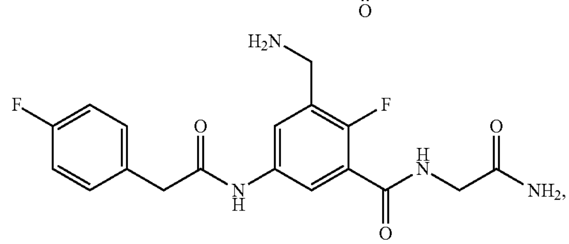

-continued

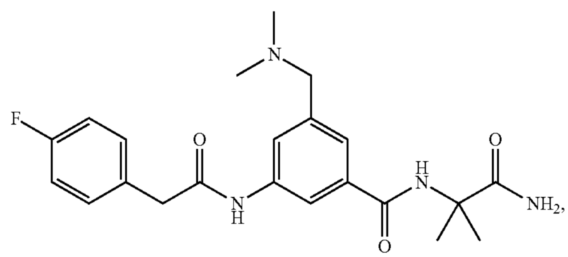

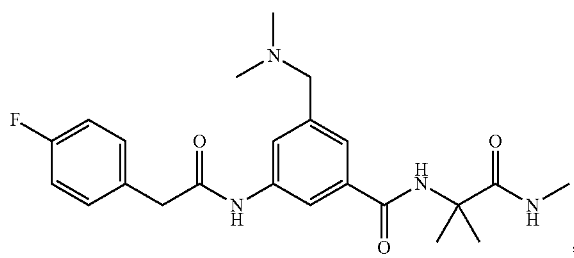

,

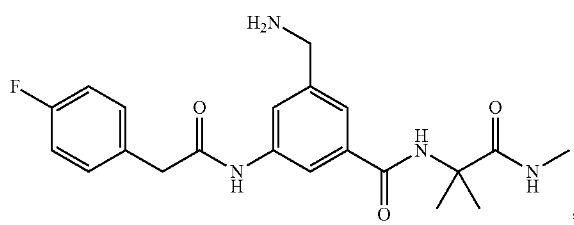

,

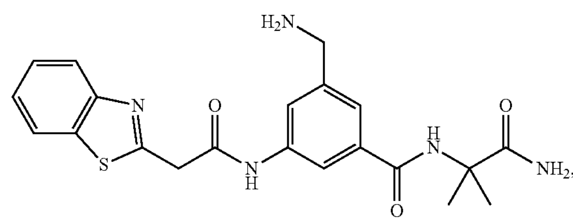

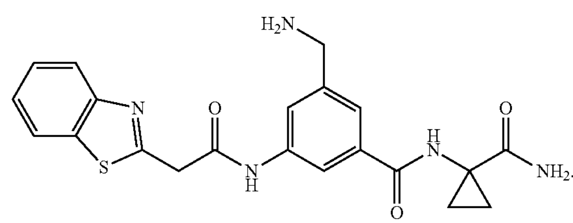

In various aspects, the compound has a structure represented by a formula:

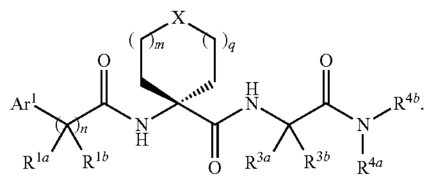

In various aspects, the compound has a structure represented by a formula:

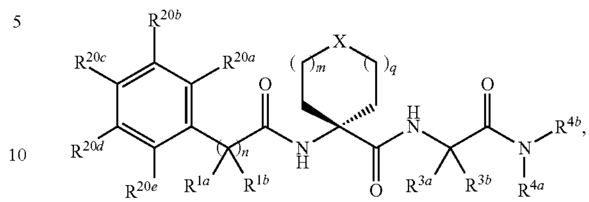

wherein each of $R^{20a}$, $R^{20b}$, $R^{20c}$, $R^{20d}$, and $R^{20e}$, is independently selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

In various aspects, the compound has a structure represented by a formula:

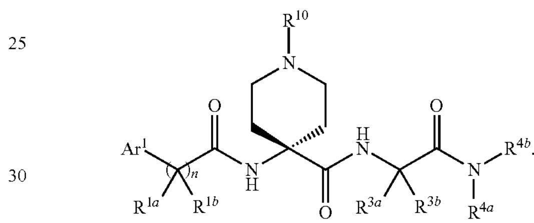

In various aspects, the compound has a structure represented b a formula:

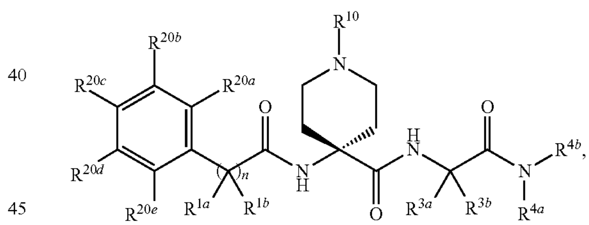

wherein each of $R^{20a}$, $R^{20b}$, $R^{20c}$, $R^{20d}$, and $R^{20e}$, is independently selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

In various aspects, the compound has a structure represented by a formula:

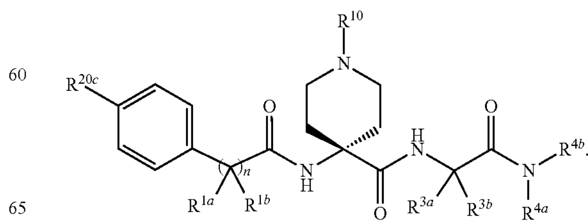

In various aspects, the compound is selected from:
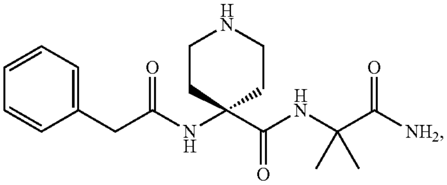
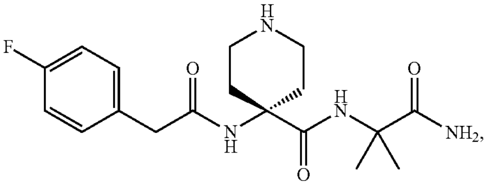
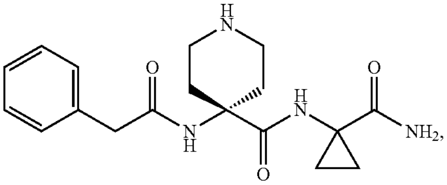
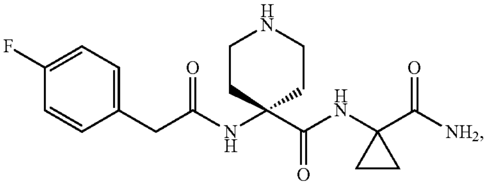
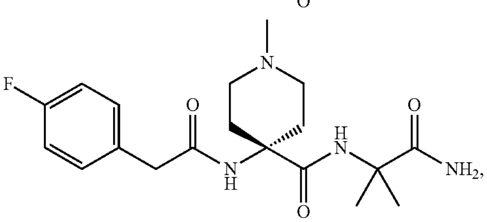
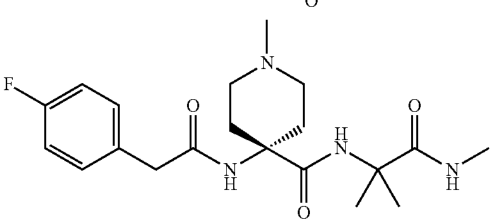
,
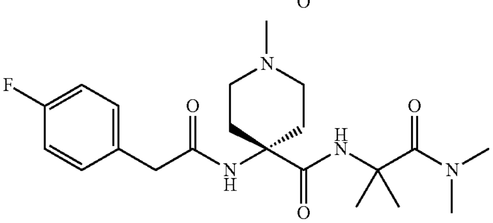
,
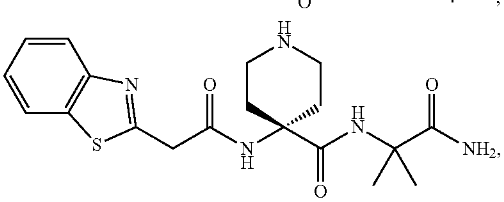
-continued
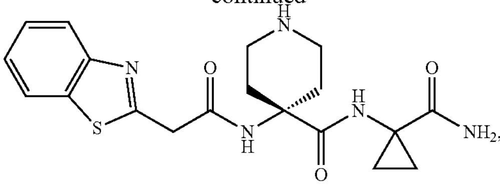
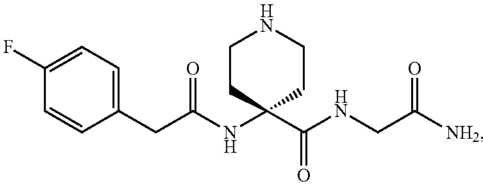
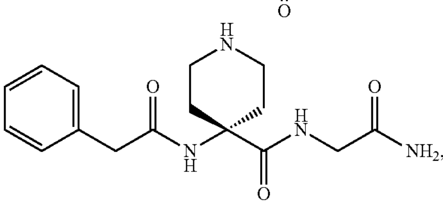
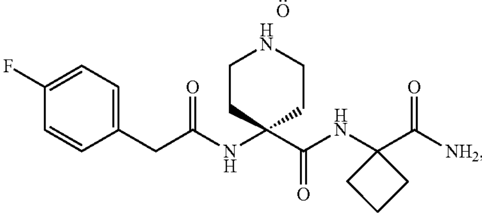
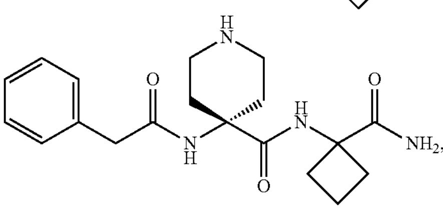
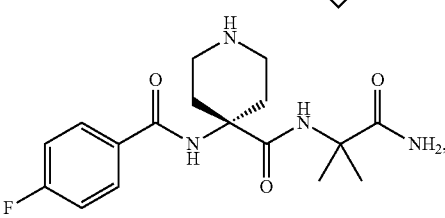
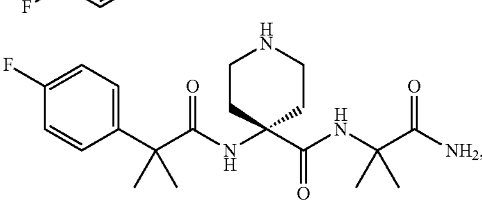
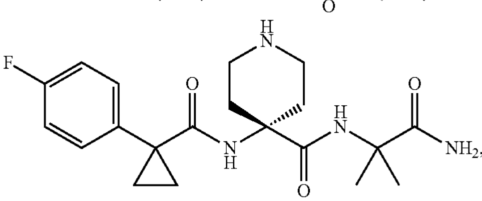
and
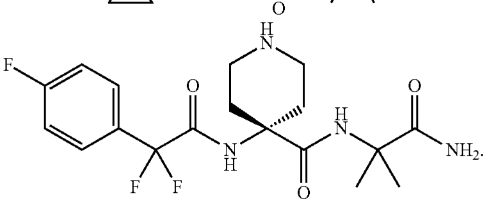

In one aspect, each of n, m, and q, when present, is independently selected from 0 and 1. In a further aspect, each of n, m, and q, when present, is 0. In a still further aspect, each of n, m, and q, when present, is 1.

In one aspect, n is selected from 0 and 1. In a further aspect, n is 0. In a still further aspect, n is 1.

In one aspect, each of m and q is independently selected from 0 and 1. In a further aspect, m is 0 and q is 1. In a still further aspect, m is 1 and q is 0. In yet a further aspect, each of m and q is 0. In an even further aspect, each of m and q is 1.

a. X Groups

In one aspect, X is selected from —O—, —S—, and —$NR^{10}$—. In a further aspect, X is selected from —O— and —S—. In a still further aspect, X is selected from —S— and —$NR^{10}$—In yet a further aspect, X is selected from —O— and —$NR^{10}$—. In an even further aspect, X is X is —O—. In a still further aspect, X is —S—. In yet a further aspect, X is —$NR^{10}$—.

In one aspect, X is selected from —O—, —S—, —$NR^{10}$—, and —$CR^{12a}R^{12b}$. In a further aspect, X is selected from —S—, —$NR^{10}$—, and —$CR^{12a}R^{12b}$. In a still further aspect, X is selected from —$NR^{10}$— and —$CR^{12a}R^{12b}$. In yet a further aspect, X is selected from —O—, —S—, and —$CR^{12a}R^{12b}$. In an even further aspect, X is selected from —O— and —$CR^{12a}R^{12b}$. In a still further aspect, X is —$CR^{12a}R^{12b}$.

b. $R^{1a}$ and $R^{1b}$ Groups

In one aspect, each of $R^{1a}$ and $R^{1b}$, when present, is independently selected from hydrogen, halogen, and C1-C4 alkyl; or each of $R^{1a}$ and $R^{1b}$, when present, are covalently bonded and, together with the intermediate atoms, comprise a C3-C6 cycloalkyl.

Thus, in one aspect, each of $R^{1a}$ and $R^{1b}$, when present, is independently selected from hydrogen, halogen, and C1-C4 alkyl. In a further aspect, each of $R^{1a}$ and $R^{1b}$, when present, is independently selected from hydrogen, —F, —Cl, —Br, methyl, ethyl, n-propyl, and isopropyl. In a still further aspect, each of $R^{1a}$ and $R^{1b}$, when present, is independently selected from hydrogen, —F, —Cl, methyl, and ethyl. In yet a further aspect, each of $R^{1a}$ and $R^{1b}$, when present, is independently selected from hydrogen, —F, —Cl, and methyl.

In a further aspect, each of $R^{1a}$ and $R^{1b}$, when present, is hydrogen.

In a further aspect, each of $R^{1a}$ and $R^{1b}$, when present, is independently selected from hydrogen and halogen. In a still further aspect, each of $R^{1a}$ and $R^{1b}$, when present, is independently selected from hydrogen, —F, —Cl, and —Br. In yet a further aspect, each of $R^{1a}$ and $R^{1b}$, when present, is independently selected from hydrogen, —F, and —Cl. In an even further aspect, each of $R^{1a}$ and $R^{1b}$, when present, is independently selected from hydrogen and —F.

In a further aspect, each of $R^{1a}$ and $R^{1b}$, when present, is independently halogen. In a still further aspect, each of $R^{1a}$ and $R^{1b}$, when present, is independently selected from —F, —Cl, and —Br. In yet a further aspect, each of $R^{1a}$ and $R^{1b}$, when present, is independently selected from —F and —Cl. In an even further aspect, each of $R^{1a}$ and $R^{1b}$, when present, is —F.

In a further aspect, each of $R^{1a}$ and $R^{1b}$, when present, is independently selected from hydrogen and C1-C4 alkyl. In a further aspect, each of $R^{1a}$ and $R^{1b}$, when present, is independently selected from hydrogen, methyl, ethyl, n-propyl, and isopropyl. In a still further aspect, each of $R^{1a}$ and $R^{1b}$, when present, is independently selected from hydrogen, methyl, and ethyl. In yet a further aspect, each of $R^{1a}$ and $R^{1b}$, when present, is independently selected from hydrogen and methyl.

In a further aspect, each of $R^{1a}$ and $R^{1b}$, when present, is independently C1-C4 alkyl. In a further aspect, each of $R^{1a}$ and $R^{1b}$, when present, is independently selected from methyl, ethyl, n-propyl, and isopropyl. In a still further aspect, each of $R^{1a}$ and $R^{1b}$, when present, is independently selected from methyl and ethyl. In yet a further aspect, each of $R^{1a}$ and $R^{1b}$, when present, is methyl.

In one aspect, each of $R^{1a}$ and $R^{1b}$, when present, are covalently bonded and, together with the intermediate atoms, comprise a C3-C6 cycloalkyl. In a further aspect, each of $R^{1a}$ and $R^{1b}$, when present, are covalently bonded and, together with the intermediate atoms, comprise a C3-C5 cycloalkyl. In a still further aspect, each of $R^{1a}$ and $R^{1b}$, when present, are covalently bonded and, together with the intermediate atoms, comprise a C3-C4 cycloalkyl. In yet a further aspect, each of $R^{1a}$ and $R^{1b}$, when present, are covalently bonded and, together with the intermediate atoms, comprise a C3 cycloalkyl. In an even further aspect, each of $R^{1a}$ and $R^{1b}$, when present, are covalently bonded and, together with the intermediate atoms, comprise a C4 cycloalkyl. In a still further aspect, each of $R^{1a}$ and $R^{1b}$, when present, are covalently bonded and, together with the intermediate atoms, comprise a C5 cycloalkyl. In yet a further aspect, each of $R^{1a}$ and $R^{1b}$, when present, are covalently bonded and, together with the intermediate atoms, comprise a C6 cycloalkyl. In an even further aspect, the cycloalkyl is unsubstituted.

c. $R^{2a}$, $R^{2b}$, and $R^{2c}$ Groups

In one aspect, each of $R^{2a}$, $R^{2b}$, and $R^{2c}$, when present, is independently selected from hydrogen, halogen, and —$CH_2NR^{11a}R^{11b}$, provided that at least one of $R^{2a}$, $R^{2b}$, and $R^{2c}$ is —$CH_2NR^{11a}R^{11b}$. In a further aspect, each of $R^{2a}$, $R^{2b}$, and $R^{2c}$, when present, is independently selected from hydrogen, —F, —Cl, —Br, and —$CH_2NR^{11a}R^{11b}$. In a still further aspect, each of $R^{2a}$, $R^{2b}$, and $R^{2c}$, when present, is independently selected from hydrogen, —F, —Cl, and —$CH_2NR^{11a}R^{11b}$. In yet a further aspect, each of $R^{2a}$, $R^{2b}$, and $R^{2c}$, when present, is independently selected from hydrogen, —F, and —$CH_2NR^{11a}R^{11b}$.

In various aspects, each of $R^{2a}$, $R^{2b}$, and $R^{2c}$, when present, is —$CH_2NR^{11a}R^{11b}$In a further aspect, two of $R^{2a}$, $R^{2b}$, and $R^{2c}$, when present, is —$CH_2NR^{11a}R^{11b}$. In a still further aspect, $R^{2a}$, when present, is —$CH_2NR^{11a}R^{11b}$. In yet a further aspect, $R^{2b}$, when present, is —$CH_2NR^{11a}R^{11b}$. In an even further aspect, $R^{2c}$, when present, is —$CH_2NR^{11a}R^{11b}$.

In various aspects, two of $R^{2a}$, $R^{2b}$, and $R^{2c}$, when present, are hydrogen. In a further aspect, each of $R^{2a}$ and $R^{2c}$, when present, is hydrogen. In a still further aspect, each of $R^{2a}$ and $R^{2b}$, when present, is hydrogen. In yet a further aspect, each of $R^{2b}$ and $R^{2c}$, when present, is hydrogen.

In various aspects, two of $R^{2a}$, $R^{2b}$, and $R^{2c}$, when present, are independently selected from hydrogen and halogen. In a further aspect, two of $R^{2a}$, $R^{2b}$, and $R^{2c}$, when present, are independently selected from hydrogen, —F, —Cl, and —Br. In a still further aspect, two of $R^{2a}$, $R^{2b}$, and $R^{2c}$, when present, are independently selected from hydrogen, —F, and —Cl. In yet a further aspect, two of $R^{2a}$, $R^{2b}$, and $R^{2c}$, when present, are independently selected from hydrogen and —Cl. In an even further aspect, two of $R^{2a}$, $R^{2b}$, and $R^{2c}$, when present, are independently selected from hydrogen and —F.

d. $R^{3a}$ and $R^{3b}$ Groups

In one aspect, each of $R^{3a}$ and $R^{3b}$ is independently selected from hydrogen and C1-C4 alkyl, or each of $R^{3a}$ and $R^{3b}$ together comprise a C3-C6 cycloalkyl.

In various aspects, each of $R^{3a}$ and $R^{3b}$ is independently selected from hydrogen and C1-C4 alkyl. In a further aspect, each of $R^{3a}$ and $R^{3b}$ is independently selected from hydrogen, methyl, ethyl, n-propyl, and isopropyl. In a still further aspect, each of $R^{3a}$ and $R^{3b}$ is independently selected from hydrogen, methyl, and ethyl. In yet a further aspect, each of $R^{3a}$ and $R^{3b}$ is independently selected from hydrogen and ethyl. In an even further aspect, each of $R^{3a}$ and $R^{3b}$ is independently selected from hydrogen and methyl.

In various aspects, each of $R^{3a}$ and $R^{3b}$ is independently C1-C4 alkyl. In a further aspect, each of $R^{3a}$ and $R^{3b}$ is independently selected from methyl, ethyl, n-propyl, and isopropyl. In a still further aspect, each of $R^{3a}$ and $R^{3b}$ is independently selected from methyl and ethyl. In yet a further aspect, each of $R^{3a}$ and $R^{3b}$ is ethyl. In an even further aspect, each of $R^{3a}$ and $R^{3b}$ is methyl.

In a further aspect, each of $R^{3a}$ and $R^{3b}$ is hydrogen.

In various aspects, each of $R^{3a}$ and $R^{3b}$ is covalently bonded and, together with the intermediate atoms, comprise a C3-C6 cycloalkyl. In a further aspect, each of $R^{3a}$ and $R^{3b}$ is covalently bonded and, together with the intermediate atoms, comprise a C3-C5 cycloalkyl. In a still further aspect, each of $R^{3a}$ and $R^{3b}$ is covalently bonded and, together with the intermediate atoms, comprise a C3-C4 cycloalkyl. In yet a further aspect, each of $R^{3a}$ and $R^{3b}$ is covalently bonded and, together with the intermediate atoms, comprise a C3 cycloalkyl. In an even further aspect, each of $R^{3a}$ and $R^{3b}$ is covalently bonded and, together with the intermediate atoms, comprise a C4 cycloalkyl. In a still further aspect, each of $R^{3a}$ and $R^{3b}$ is covalently bonded and, together with the intermediate atoms, comprise a C5 cycloalkyl. In yet a further aspect, each of $R^{3a}$ and $R^{3b}$ is covalently bonded and, together with the intermediate atoms, comprise a C6 cycloalkyl. In an even further aspect, the cycloalkyl is unsubstituted.

e. $R^{4a}$ and $R^{4b}$ Groups

In one aspect, each of $R^{4a}$ and $R^{4b}$ is independently selected from hydrogen and C1-C4 alkyl. In a further aspect, each of $R^{4a}$ and $R^{4b}$ is independently selected from hydrogen, methyl, ethyl, n-propyl, and isopropyl. In a still further aspect, each of $R^{4a}$ and $R^{4b}$ is independently selected from hydrogen, methyl, and ethyl. In yet a further aspect, each of $R^{4a}$ and $R^{4b}$ is independently selected from hydrogen and ethyl. In an even further aspect, each of $R^{4a}$ and $R^{4b}$ is independently selected from hydrogen and methyl.

In various aspects, each of $R^{4a}$ and $R^{4b}$ is independently C1-C4 alkyl. In a further aspect, each of $R^{4a}$ and $R^{4b}$ is independently selected from methyl, ethyl, n-propyl, and isopropyl. In a still further aspect, each of $R^{4a}$ and $R^{4b}$ is independently selected from methyl and ethyl. In yet a further aspect, each of $R^{4a}$ and $R^{4b}$ is ethyl. In an even further aspect, each of $R^{4a}$ and $R^{4b}$ is methyl.

In a further aspect, each of $R^{4a}$ and $R^{4b}$ is hydrogen.

In various aspects, one of $R^{4a}$ and $R^{4b}$ is hydrogen and one of $R^{4a}$ and $R^{4b}$ is C1-C4 alkyl. In a further aspect, $R^{4a}$ is hydrogen and $R^{4b}$ is C1-C4 alkyl. In a still further aspect, $R^{4b}$ is hydrogen and $R^{4a}$ is C1-C4 alkyl.

f. $R^{10}$ Groups

In one aspect, $R^{10}$, when present, is selected from hydrogen and C1-C4 alkyl. In a further aspect, $R^{10}$, when present, is selected from hydrogen, methyl, ethyl, n-propyl, and isopropyl. In a still further aspect, $R^{10}$, when present, is selected from hydrogen, methyl, and ethyl. In yet a further aspect, $R^{10}$, when present, is selected from hydrogen and ethyl. In an even further aspect, $R^{10}$, when present, is selected from hydrogen and methyl.

In a further aspect, $R^{10}$, when present, is hydrogen.

In various aspects, $R^{10}$, when present, is C1-C4 alkyl. In a further aspect, $R^{10}$, when present, is selected from methyl, ethyl, n-propyl, and isopropyl. In a still further aspect, $R^{10}$, when present, is selected from methyl and ethyl. In yet a further aspect, $R^{10}$, when present, is ethyl. In an even further aspect, $R^{10}$, when present, is methyl.

g. $R^{11a}$ and $R^{11b}$ Groups

In one aspect, each of $R^{11a}$ and $R^{11b}$, when present, is independently selected from hydrogen and C1-C4 alkyl. In a further aspect, each of $R^{11a}$ and $R^{11b}$, when present, is independently selected from hydrogen, methyl, ethyl, n-propyl, and isopropyl. In a still further aspect, each of $R^{11a}$ and $R^{11b}$, when present, is independently selected from hydrogen, methyl, and ethyl. In yet a further aspect, each of $R^{11a}$ and $R^{11b}$, when present, is independently selected from hydrogen and ethyl. In an even further aspect, each of $R^{11a}$ and $R^{11b}$, when present, is independently selected from hydrogen and methyl.

In a further aspect, each of $R^{11a}$ and $R^{11b}$, when present, is hydrogen.

In various aspects, each of $R^{11a}$ and $R^{11b}$, when present, is independently C1-C4 alkyl. In a further aspect, each of $R^{11a}$ and $R^{11b}$, when present, is independently selected from methyl, ethyl, n-propyl, and isopropyl. In a still further aspect, each of $R^{11a}$ and $R^{11b}$, when present, is independently selected from methyl and ethyl. In yet a further aspect, each of $R^{11a}$ and $R^{11b}$, when present, is ethyl. In an even further aspect, each of $R^{11a}$ and $R^{11b}$, when present, is methyl.

h. $R^{12a}$ and $R^{12b}$ Groups

In one aspect, each of $R^{12a}$ and $R^{12b}$, when present, is independently selected from hydrogen and C1-C4 alkyl. In a further aspect, each of $R^{12a}$ and $R^{12b}$, when present, is independently selected from hydrogen, methyl, ethyl, n-propyl, and isopropyl. In a still further aspect, each of $R^{12a}$ and $R^{12b}$, when present, is independently selected from hydrogen, methyl, and ethyl. In yet a further aspect, each of $R^{12a}$ and $R^{12b}$, when present, is independently selected from hydrogen and ethyl. In an even further aspect, each of $R^{12a}$ and $R^{12b}$, when present, is independently selected from hydrogen and methyl.

In a further aspect, each of $R^{12a}$ and $R^{12b}$, when present, is hydrogen.

In various aspects, each of $R^{12a}$ and $R^{12b}$, when present, is independently C1-C4 alkyl. In a further aspect, each of $R^{12a}$ and $R^{12b}$, when present, is independently selected from methyl, ethyl, n-propyl, and isopropyl. In a still further aspect, each of $R^{12a}$ and $R^{12b}$, when present, is independently selected from methyl and ethyl. In yet a further aspect, each of $R^{12a}$ and $R^{12b}$, when present, is ethyl. In an even further aspect, each of $R^{12a}$ and $R^{12b}$, when present, is methyl.

i. $R^{20a}$, $R^{20b}$, $R^{20c}$, $R^{20d}$, and $R^{20e}$ Groups

In one aspect, each of $R^{20a}$, $R^{20b}$, $R^{20c}$, $R^{20d}$, and $R^{20e}$ is independently selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, each of $R^{20a}$, $R^{20b}$, $R^{20c}$, $R^{20d}$, and $R^{20e}$ is independently selected from hydrogen, —F, —Cl, —CN, —$NH_2$, —OH, —$NO_2$, methyl, ethyl, n-propyl, isopropyl, ethenyl, n-propenyl, isopropenyl, —$CH_2F$, —$CHF_2$, —$CF_3$, $—CH_2CH_2F$, $—CH_2CH_2CH_2F$, $—CH(CH_3)CH_2F$, $—CH_2Cl$, $—CHCl_2$, $—CCl_3$, $—CH_2CH_2Cl$, $—CH_2CH_2CH_2Cl$, $—CH(CH_3)CH_2Cl$, $—CH_2CN$, $—CH_2CH_2CN$, $—CH_2CH_2CH_2CN$, $—CH(CH_3)CH_2CN$, $—CH_2OH$, $—CH_2CH_2OH$, $—CH_2CH_2CH_2OH$, $—CH(CH_3)CH_2OH$, $—OCH_2F$, $—OCHF_2$, $—OCF_3$, $—OCH_2CH_2F$, $—OCH_2CH_2CH_2F$, $—OCH(CH_3)CH_2F$, $—OCH_3$, $—OCH_2CH_3$, $—OCH_2CH_2CH_3$, $—OCH(CH_3)_2$, $—NHCH_3$, $—NHCH_2CH_3$, $—NHCH_2CH_2CH_3$, $—NHCH(CH_3)_2$, $—N(CH_3)_2$, $—N(CH_2CH_3)_2$, $—N(CH_3)(CH_2CH_3)$, $—N(CH_2CH_2CH_3)_2$, $—N(CH(CH_3)_2)_2$, $—CH_2NH_2$, $—CH_2CH_2NH_2$, $—CH_2CH_2CH_2NH_2$, and $—CH(CH_3)CH_2NH_2$. In a still further aspect, each of $R^{20a}$, $R^{20b}$, $R^{20c}$, $R^{20d}$, and $R^{20e}$ is independently selected from hydrogen, —F, —Cl, —CN, $—NH_2$, —OH, $—NO_2$, methyl, ethyl, ethenyl, $—CH_2F$, $—CHF_2$, $—CF_3$, $—CH_2CH_2F$, $—CH_2Cl$, $—CHCl_2$, $—CCl_3$, $—CH_2CH_2Cl$, $—CH_2CN$, $—CH_2CH_2CN$, $—CH_2OH$, $—CH_2CH_2OH$, $—OCH_2F$, $—OCHF_2$, $—OCF_3$, $—OCH_2CH_2F$, $—OCH_3$, $—OCH_2CH_3$, $—NHCH_3$, $—NHCH_2CH_3$, $—N(CH_3)_2$, $—N(CH_2CH_3)_2$, $—N(CH_3)(CH_2CH_3)$, $—CH_2NH_2$, and $—CH_2CH_2NH_2$. In yet a further aspect, each of $R^{20a}$, $R^{20b}$, $R^{20c}$, $R^{20d}$, and $R^{20e}$ is independently selected from hydrogen, —F, —Cl, —CN, $—NH_2$, —OH, $—NO_2$, methyl, $—CH_2F$, $—CHF_2$, $—CF_3$, $—CH_2Cl$, $—CHCl_2$, $—CCl_3$, $—CH_2CN$, $—CH_2OH$, $—OCH_2F$, $—OCHF_2$, $—OCF_3$, $—OCH_3$, $—NHCH_3$, $—N(CH_3)_2$, and $—CH_2NH_2$.

In a further aspect, each of $R^{20a}$, $R^{20b}$, $R^{20c}$, $R^{20d}$, and $R^{20e}$ is independently selected from hydrogen, halogen, C1-C4 haloalkyl, C1-C4 haloalkoxy, and C1-C4 alkoxy. In a still further aspect, each of $R^{20a}$, $R^{20b}$, $R^{20c}$, $R^{20d}$, and $R^{20e}$ is independently selected from hydrogen, —F, —Cl, $—CH_2F$, $—CHF_2$, $—CF_3$, $—CH_2CH_2F$, $—CH_2CH_2CH_2F$, $—CH(CH_3)CH_2F$, $—CH_2Cl$, $—CHCl_2$, $—CCl_3$, $—CH_2CH_2Cl$, $—CH_2CH_2CH_2Cl$, $—CH(CH_3)CH_2Cl$, $—OCH_2F$, $—OCHF_2$, $—OCF_3$, $—OCH_2CH_2F$, $—OCH_2CH_2CH_2F$, $—OCH(CH_3)CH_2F$, $—OCH_3$, $—OCH_2CH_3$, $—OCH_2CH_2CH_3$, and $—OCH(CH_3)_2$. In yet a further aspect, each of $R^{20a}$, $R^{20b}$, $R^{20c}$, $R^{20d}$, and $R^{20e}$ is independently selected from hydrogen, —F, —Cl, $—CH_2F$, $—CHF_2$, $—CF_3$, $—CH_2CH_2F$, $—CH_2Cl$, $—CHCl_2$, $—CCl_3$, $—CH_2CH_2Cl$, $—OCH_2F$, $—OCHF_2$, $—OCF_3$, $—OCH_2CH_2F$, $—OCH_3$, and $—OCH_2CH_3$. In an even further aspect, each of $R^{20a}$, $R^{20b}$, $R^{20c}$, $R^{20d}$, and $R^{20e}$ is independently selected from hydrogen, —F, —Cl, $—CH_2F$, $—CHF_2$, $—CF_3$, $—CH_2Cl$, $—CHCl_2$, $—CCl_3$, $—OCH_2F$, $—OCHF_2$, $—OCF_3$, and $—OCH_3$.

In various aspects, each of $R^{20a}$, $R^{20b}$, $R^{20c}$, $R^{20d}$, and $R^{20e}$ is independently selected from hydrogen, halogen, —CN, $—NO_2$, C1-C4 haloalkyl, C1-C4 cyanoalkyl, and C1-C4 haloalkoxy. In a further aspect, each of $R^{20a}$, $R^{20b}$, $R^{20c}$, $R^{20d}$, and $R^{20e}$ is independently selected from hydrogen, —F, —Cl, —CN, $—NO_2$, $—CH_2F$, $—CHF_2$, $—CF_3$, $—CH_2CH_2F$, $—CH_2CH_2CH_2F$, $—CH(CH_3)CH_2F$, $—CH_2Cl$, $—CHCl_2$, $—CCl_3$, $—CH_2CH_2Cl$, $—CH_2CH_2CH_2Cl$, $—CH(CH_3)CH_2Cl$, $—CH_2CN$, $—CH_2CH_2CN$, $—CH_2CH_2CH_2CN$, $—CH(CH_3)CH_2CN$, $—OCF_3$, $—OCH_2CH_2F$, $—OCH_2CH_2CH_2F$, and $—OCH(CH_3)CH_2F$. In a still further aspect, each of $R^{20a}$, $R^{20b}$, $R^{20c}$, $R^{20d}$, and $R^{20e}$ is independently selected from hydrogen, —F, —Cl, —CN, $—NO_2$, $—CH_2F$, $—CHF_2$, $—CF_3$, $—CH_2CH_2F$, $—CH_2Cl$, $—CHCl_2$, $—CCl_3$, $—CH_2CH_2Cl$, $—CH_2CN$, $—CH_2CH_2CN$, $—OCH_2F$, $—OCHF_2$, $—OCF_3$, and $—OCH_2CH_2F$. In yet a further aspect, each of $R^{20a}$, $R^{20b}$, $R^{20c}$, $R^{20d}$, and $R^{20e}$ is independently selected from hydrogen, —F, —Cl, —CN, $—NO_2$, $—CH_2F$, $—CHF_2$, $—CF_3$, $—CH_2Cl$, $—CHCl_2$, $—CCl_3$, $—CH_2CN$, $—OCH_2F$, $—OCHF_2$, and $—OCF_3$.

In various aspects, each of $R^{20a}$, $R^{20b}$, $R^{20c}$, $R^{20d}$, and $R^{20e}$ is independently selected from hydrogen, $—NH_2$, —OH, C1-C4 hydroxyalkyl, C1-C4 alkoxy, C1-C4 alkylamino, (C1-C4)(C1-C4) dialkylamino, and C1-C4 aminoalkyl. In a further aspect, each of $R^{20a}$, $R^{20b}$, $R^{20c}$, $R^{20d}$, and $R^{20e}$ is independently selected from hydrogen, $—NH_2$, —OH, $—CH_2OH$, $—CH_2CH_2OH$, $—CH_2CH_2CH_2OH$, $—CH(CH_3)CH_2OH$, $—OCH_3$, $—OCH_2CH_3$, $—OCH_2CH_2CH_3$, $—OCH(CH_3)_2$, $—NHCH_3$, $—NHCH_2CH_3$, $—NHCH_2CH_2CH_3$, $—NHCH(CH_3)_2$, $—N(CH_3)_2$, $—N(CH_2CH_3)_2$, $—N(CH_3)(CH_2CH_3)$, $—N(CH_2CH_2CH_3)_2$, $—N(CH(CH_3)_2)_2$, $—CH_2NH_2$, $—CH_2CH_2NH_2$, $—CH_2CH_2CH_2NH_2$, and $—CH(CH_3)CH_2NH_2$. In a still further aspect, each of $R^{20a}$, $R^{20b}$, $R^{20c}$, $R^{20d}$, and $R^{20e}$ is independently selected from hydrogen, $—NH_2$, —OH, $—CH_2OH$, $—CH_2CH_2OH$, $—OCH_3$, $—OCH_2CH_3$, $—NHCH_3$, $—NHCH_2CH_3$, $—N(CH_3)_2$, $—N(CH_2CH_3)_2$, $—N(CH_3)(CH_2CH_3)$, $—CH_2NH_2$, and $—CH_2CH_2NH_2$. In yet a further aspect, each of $R^{20a}$, $R^{20b}$, $R^{20c}$, $R^{20d}$, and $R^{20e}$ is independently selected from hydrogen, $—NH_2$, —OH, $—CH_2OH$, $—OCH_3$, $—NHCH_3$, $—N(CH_3)_2$, and $—CH_2NH_2$.

In various aspects, each of $R^{20a}$, $R^{20b}$, $R^{20c}$, $R^{20d}$, and $R^{20e}$ is independently selected from hydrogen, C1-C4 alkyl, and C2-C4 alkenyl. In a further aspect, each of $R^{20a}$, $R^{20b}$, $R^{20c}$, $R^{20d}$, and $R^{20e}$ is independently selected from hydrogen, methyl, ethyl, n-propyl, isopropyl, ethenyl, n-propenyl, and isopropenyl. In a still further aspect, each of $R^{20a}$, $R^{20b}$, $R^{20c}$, $R^{20d}$, and $R^{20e}$ is independently selected from hydrogen, methyl, ethyl, and ethenyl. In yet a further aspect, each of $R^{20a}$, $R^{20b}$, $R^{20c}$, $R^{20d}$, and $R^{20e}$ is independently selected from hydrogen and methyl.

In a further aspect, each of $R^{20a}$, $R^{20b}$, $R^{20c}$, $R^{20d}$, and $R^{20e}$ is independently independently selected from hydrogen and halogen. In a still further aspect, each of $R^{20a}$, $R^{20b}$, $R^{20c}$, $R^{20d}$, and $R^{20e}$ is independently selected from hydrogen, —F, —Cl, and —Br. In yet a further aspect, each of $R^{20a}$, $R^{20b}$, $R^{20c}$, $R^{20d}$, and $R^{20e}$ is independently selected from hydrogen, —F, and —Cl. In an even further aspect, each of $R^{20a}$, $R^{20b}$, $R^{20c}$, $R^{20d}$, and $R^{20e}$ is independently selected from hydrogen and —Cl. In a still further aspect, each of $R^{20a}$, $R^{20b}$, $R^{20c}$, $R^{20d}$, and $R^{20e}$ is independently selected from hydrogen and —F.

In a further aspect, each of $R^{20a}$, $R^{20b}$, $R^{20c}$, $R^{20d}$, and $R^{20e}$ is hydrogen.

j. $R^{21a}$ and $R^{21b}$ Groups

In one aspect, each of $R^{21a}$ and $R^{21b}$ is independently selected from hydrogen and C1-C4 alkyl. In a further aspect, each of $R^{21a}$ and $R^{21b}$ is independently selected from hydrogen, methyl, ethyl, n-propyl, and isopropyl. In a still further aspect, each of $R^{21a}$ and $R^{21b}$ is independently selected from hydrogen, methyl, and ethyl. In yet a further aspect, each of $R^{21a}$ and $R^{21b}$ is independently selected from hydrogen and ethyl. In an even further aspect, each of $R^{21a}$ and $R^{21b}$ is independently selected from hydrogen and methyl.

In a further aspect, each of $R^{21a}$ and $R^{21b}$ is hydrogen.

In various aspects, each of $R^{21a}$ and $R^{21b}$ is independently C1-C4 alkyl. In a further aspect, each of $R^{21a}$ and $R^{21b}$ is independently selected from methyl, ethyl, n-propyl, and isopropyl. In a still further aspect, each of $R^{21a}$ and $R^{21b}$ is independently selected from methyl and ethyl. In yet a further aspect, each of $R^{21a}$ and $R^{21b}$ is ethyl. In an even further aspect, each of $R^{21a}$ and $R^{21b}$ is methyl.

k. $Ar^1$ Groups

In one aspect, $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Ar^1$ is selected from C6-C14 aryl and C2-C10 heteroaryl, and is substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Ar^1$ is selected from C6-C14 aryl and C2-C10 heteroaryl, and is substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Ar^1$ is selected from C6-C14 aryl and C2-C10 heteroaryl, and is monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Ar^1$ is selected from C6-C14 aryl and C2-C10 heteroaryl, and is unsubstituted.

In various aspects, $Ar^1$ is C6-C14 aryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C6-C14 aryls include, but are not limited to, phenyl, naphthyl, anthracenyl, and phenanthrenyl. In a further aspect, $Ar^1$ is C6-C14 aryl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Ar^1$ is C6-C14 aryl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Ar^1$ is C6-C14 aryl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Ar^1$ is unsubstituted C6-C14 aryl.

In various aspects, $Ar^1$ is phenyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Ar^1$ is phenyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Ar^1$ is phenyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Ar^1$ is phenyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Ar^1$ is unsubstituted phenyl.

In various aspects, $Ar^1$ is phenyl substituted with 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Ar^1$ is phenyl para-substituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Ar^1$ is phenyl para-substituted with a halogen group. In yet a further aspect, $Ar^1$ is phenyl para-substituted with a —F group.

In various aspects, $Ar^1$ is C2-C10 heteroaryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C2-C10 heteroaryls include, but are not limited to, furanyl, thiophenyl, pyrrolyl, benzo[d]thiazole, pyrazolyl, imidazolyl, triazolyl, oxazolyl, thiazolyl, pyridinyl, pyrimidinyl, imidazolyl, purinyl, indolyl, and quinolinyl. In a further aspect, $Ar^1$ is C2-C10 heteroaryl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Ar^1$ is C2-C10 heteroaryl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Ar^1$ is C2-C10 heteroaryl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Ar^1$ is unsubstituted C2-C10 heteroaryl.

In various aspects, $Ar^1$ is benzo[d]thiazole substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Ar^1$ is benzo[d]thiazole substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Ar^1$ is benzo[d]thiazole substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Ar^1$ is benzo[d]thiazole monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Ar^1$ is unsubstituted benzo[d]thiazole.

2. Example Compounds

In one aspect, a compound can be present as:

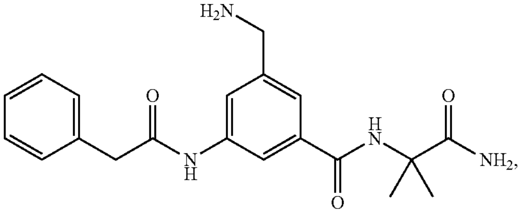

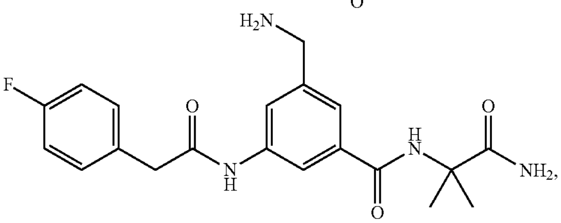

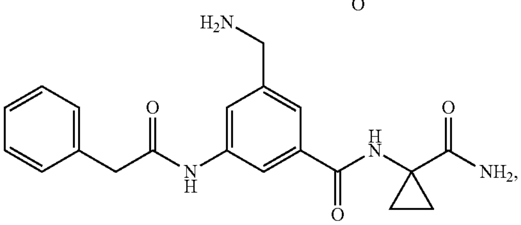

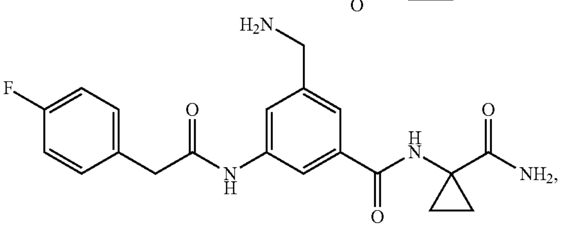

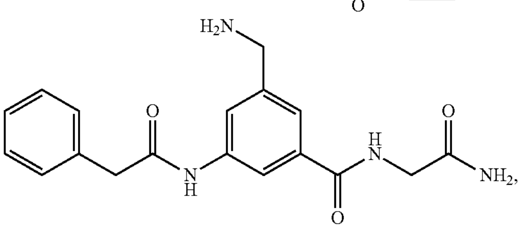

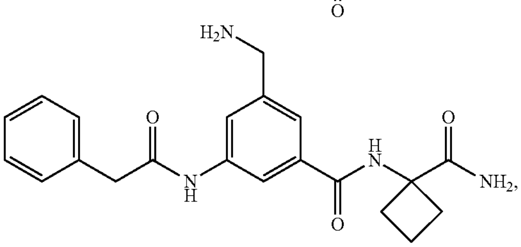

-continued

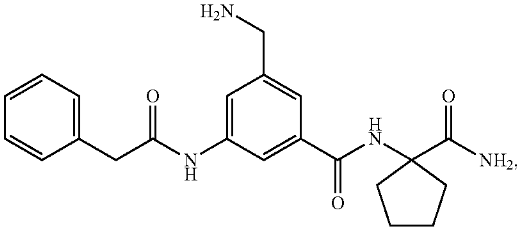

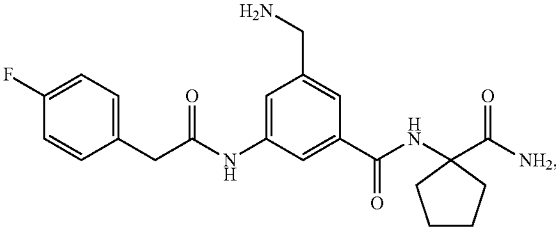

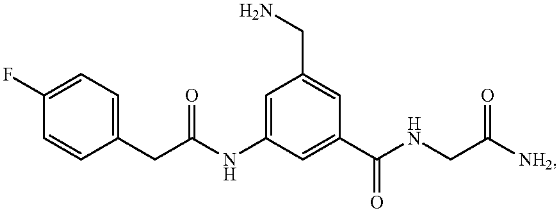

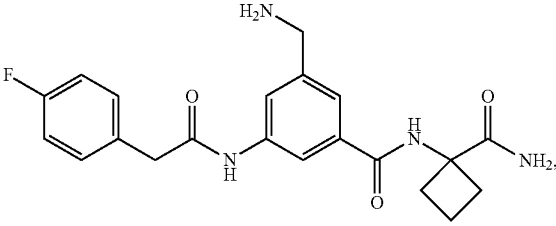

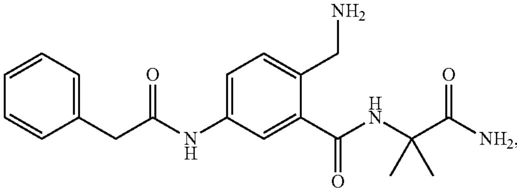

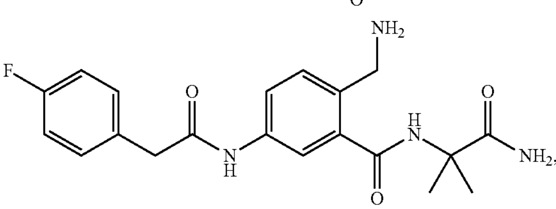

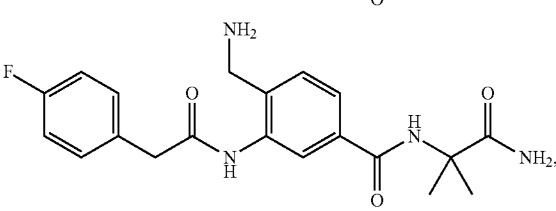

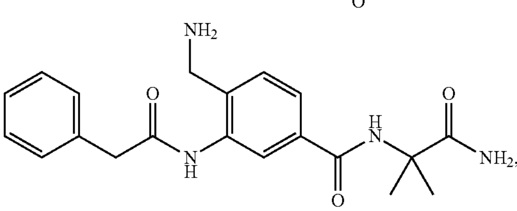

-continued
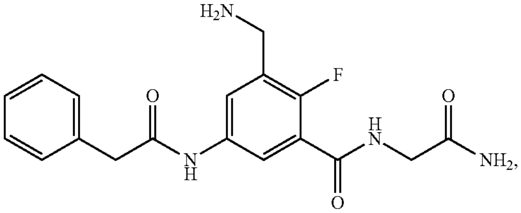
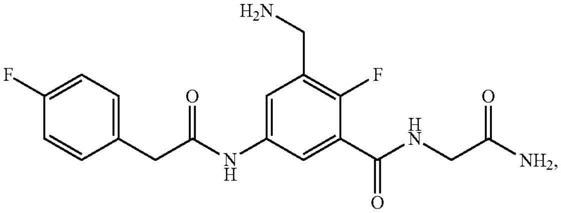
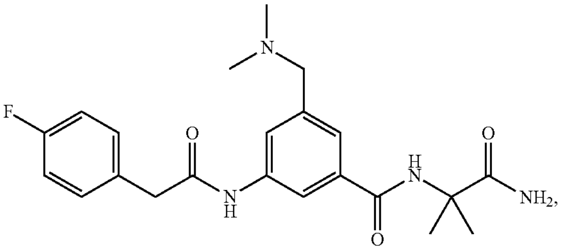
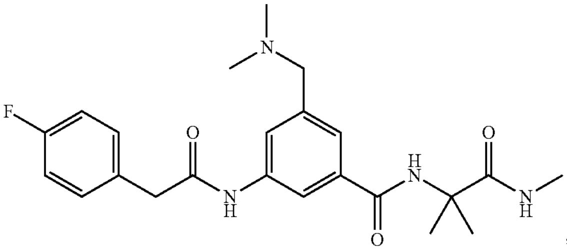
,
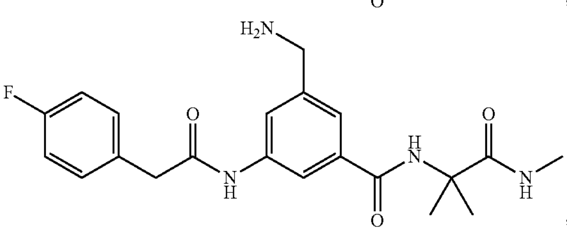
,
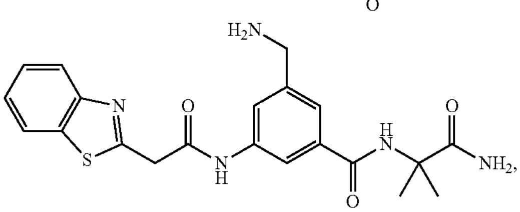
and
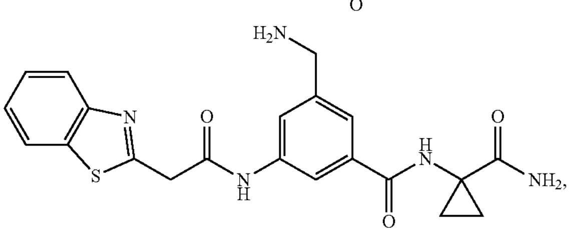
or a pharmaceutically acceptable salt thereof.
In one aspect, a compound can be present as:
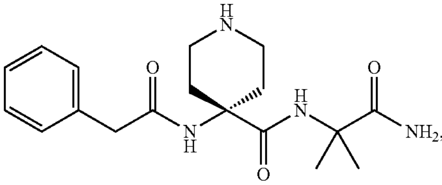
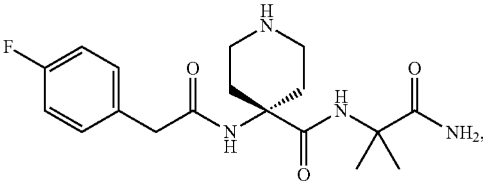
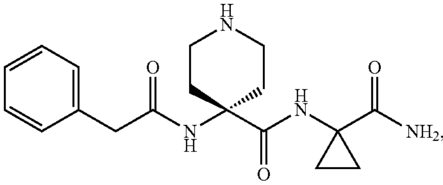
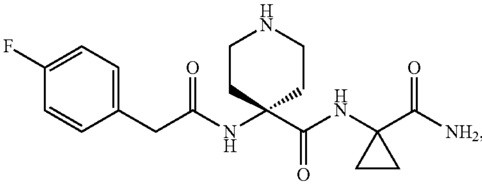
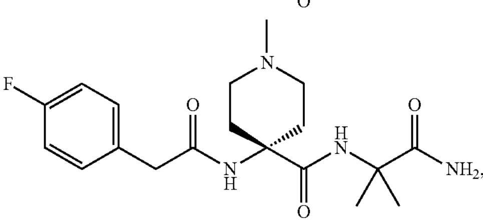
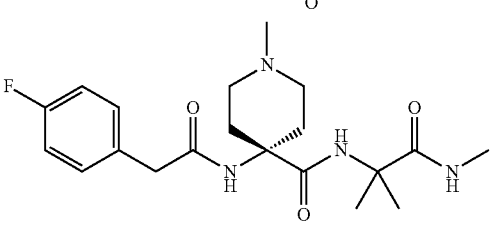
,
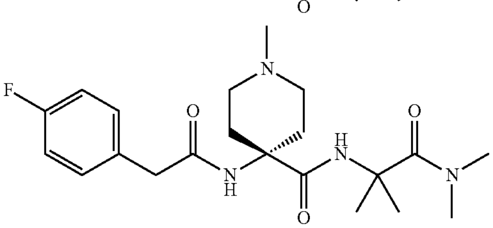
,
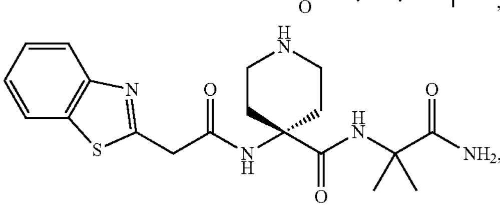

-continued

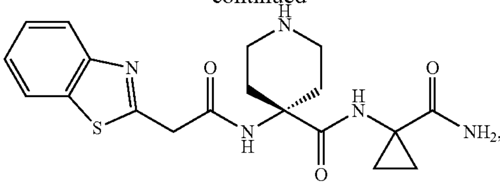

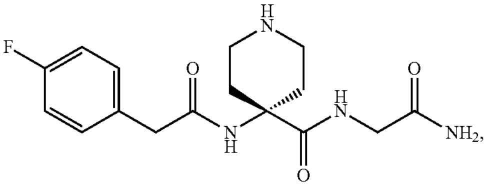

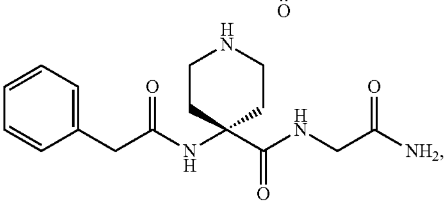

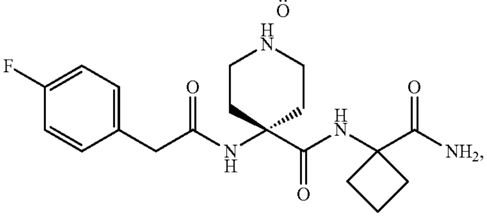

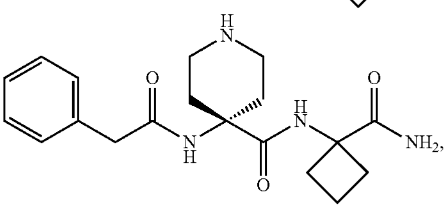

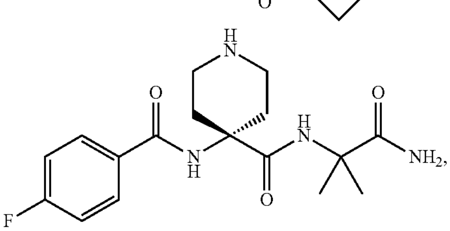

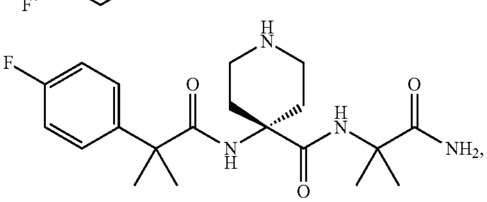

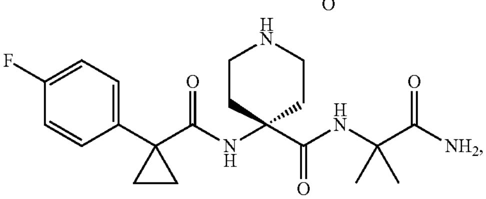

and

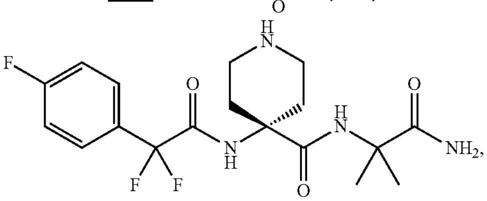

or a pharmaceutically acceptable salt thereof.

It is contemplated that one or more compounds can optionally be omitted from the disclosed invention.

It is understood that the disclosed compounds can be used in connection with the disclosed methods, compositions, kits, and uses.

It is understood that pharmaceutical acceptable derivatives of the disclosed compounds can be used also in connection with the disclosed methods, compositions, kits, and uses. The pharmaceutical acceptable derivatives of the compounds can include any suitable derivative, such as pharmaceutically acceptable salts as discussed below, isomers, radiolabeled analogs, tautomers, and the like.

C. Pharmaceutical Compositions

In one aspect, disclosed are pharmaceutical compositions comprising a disclosed compound, or a pharmaceutically acceptable salt thereof and a pharmaceutically acceptable carrier.

Thus, in one aspect, disclosed are pharmaceutical compositions comprising a therapeutically effective amount of a compound having a structure represented by a formula selected from:

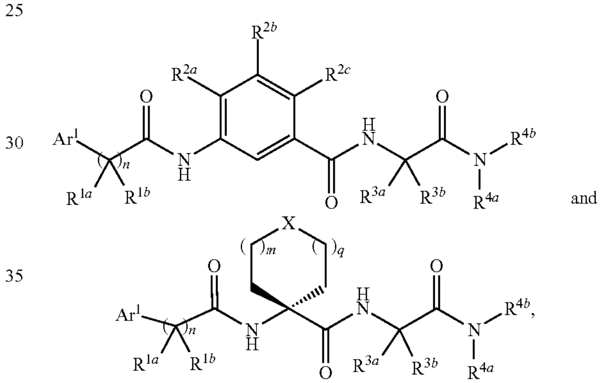

and wherein each of n, m, and q, when present, is independently selected from 0 and 1; wherein X, when present, is selected from —O—, —S—, and —$NR^{10}$—; wherein $R^{10}$, when present, is selected from hydrogen and C1-C4 alkyl; wherein each of $R^{1a}$ and $R^{1b}$, when present, is independently selected from hydrogen, halogen, and C1-C4 alkyl; or wherein each of $R^{1a}$ and $R^{1b}$, when present, together comprise a C3-C6 cycloalkyl; wherein each of $R^{2a}$, $R^{2b}$, and $R^{2c}$, when present, is independently selected from hydrogen, halogen, and —$CH_2NR^{11a}R^{11b}$, provided that at least one of $R^{2a}$, $R^{2b}$, and $R^{2c}$ is —$CH_2NR^{11a}R^{11b}$; wherein each of $R^{11a}$ and $R^{11b}$, when present, is independently selected from hydrogen and C1-C4 alkyl; wherein each of $R^{3a}$ and $R^{3b}$ is independently selected from hydrogen and C1-C4 alkyl, or wherein each of $R^{3a}$ and $R^{3b}$ together comprise a C3-C6 cycloalkyl; wherein each of $R^{4a}$ and $R^{4b}$ is independently selected from hydrogen and C1-C4 alkyl; and wherein $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, and a pharmaceutically acceptable carrier.

In various aspects, the compounds and compositions of the invention can be administered in pharmaceutical compositions, which are formulated according to the intended method of administration. The compounds and compositions described herein can be formulated in a conventional manner using one or more physiologically acceptable carriers or excipients. For example, a pharmaceutical composition can be formulated for local or systemic administration, intravenous, topical, or oral administration.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, P A 1990.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, an effective amount is a therapeutically effective amount. In a still further aspect, an effective amount is a prophylactically effective amount.

In a further aspect, the pharmaceutical composition is administered to a mammal. In a still further aspect, the mammal is a human. In an even further aspect, the human is a patient.

In a further aspect, the pharmaceutical composition is used to treat a disorder of uncontrolled cellular proliferation such as, for example, cancers including, but not limited to, sarcomas, carcinomas, hematological cancers, solid tumors, breast cancer, cervical cancer, gastrointestinal cancer, colorectal cancer, brain cancer, skin cancer, prostate cancer, ovarian cancer, bladder cancer, thyroid cancer, testicular cancer, pancreatic cancer, endometrial cancer, melanomas, gliomas, leukemias, lymphomas, chronic myeloproliferative disorders, myelodysplastic syndromes, myeloproliferative neoplasms, and plasma cell neoplasms (myelomas).

It is understood that the disclosed compositions can be prepared from the disclosed compounds. It is also understood that the disclosed compositions can be employed in the disclosed methods of using.

D. Methods of Making a Compound

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. In certain specific examples, the disclosed compounds can be prepared by Routes I-III, as described and exemplified below. The following examples are provided so that the invention might be more fully understood, are illustrative only, and should not be construed as limiting.

1. Route I

In one aspect, substituted phenyl analogs can be prepared as shown below.

SCHEME 1A.

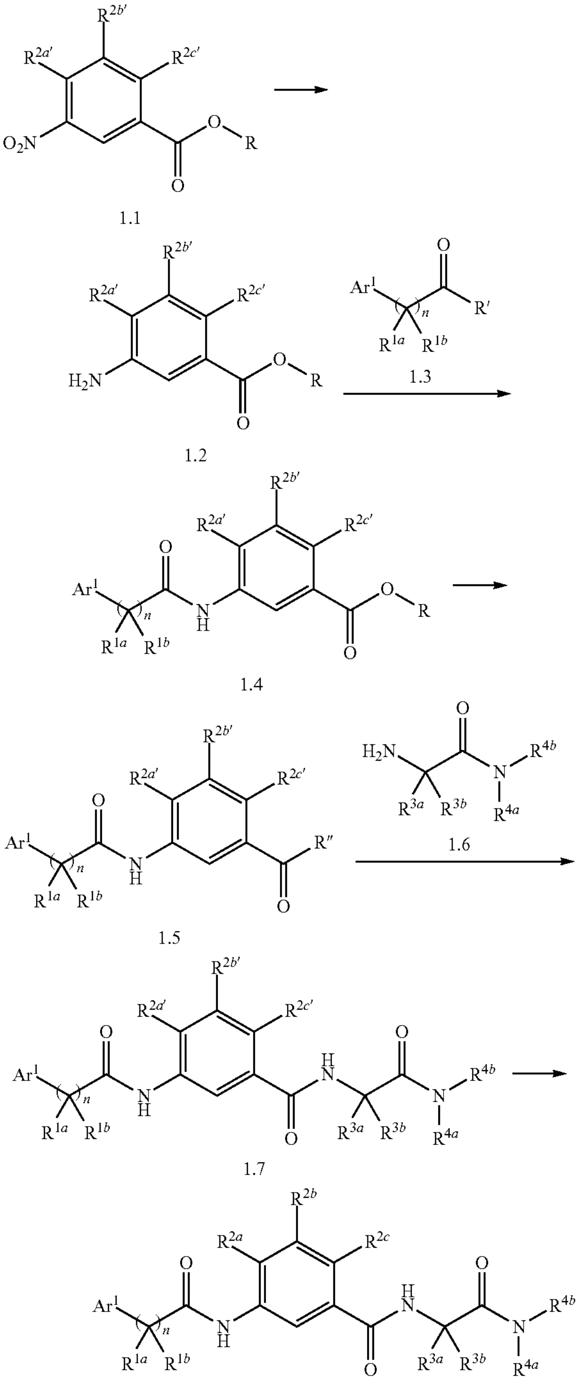

1.1

1.2

1.3

1.4

1.5

1.6

1.7

1.8

Compounds are represented in generic form, wherein R is a C1-C4 alkyl, wherein each of R' and R" is independently selected from halogen and —OH, wherein each of $R^{2a'}$, $R^{2b'}$, and $R^{2c'}$ is independently selected from hydrogen, halogen, —$CH_2NR^{11a}R^{11b}$, and —CN, provided that one and only one of of $R^{2a'}$, $R^{2b'}$, and $R^{2c'}$ is —CN, and with other substituents as noted in compound descriptions elsewhere herein. A more specific example is set forth below.

SCHEME 1B.

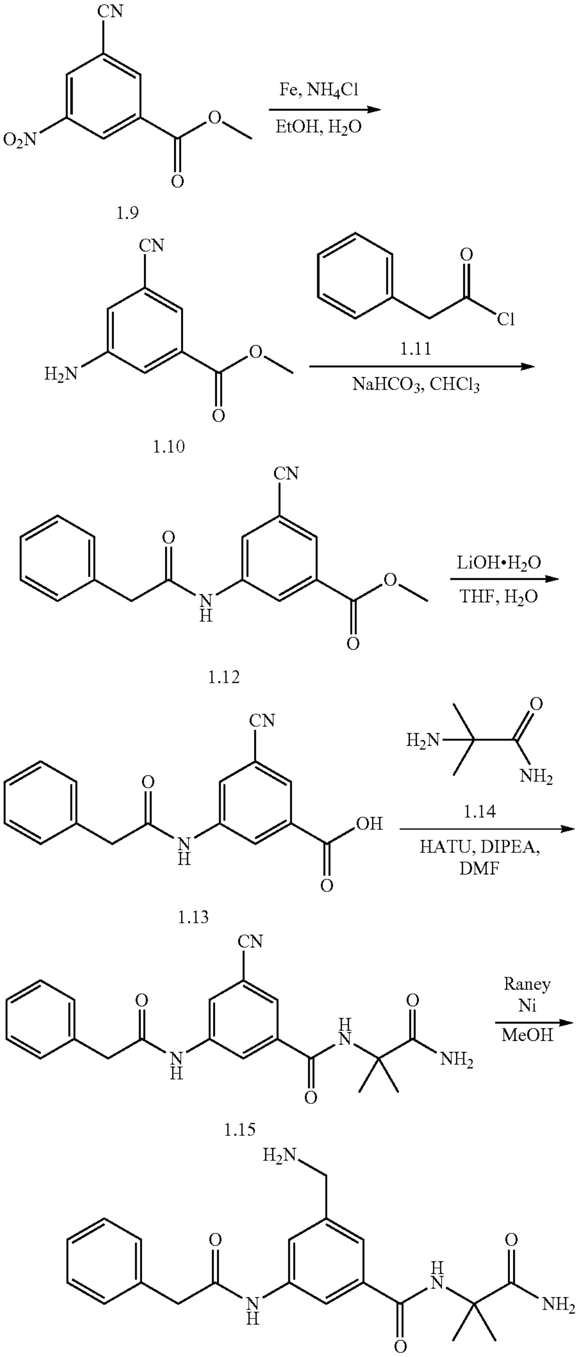

1.9, 1.10, 1.12, 1.13, 1.15, 1.16

In one aspect, compounds of type 1.16, and similar compounds, can be prepared according to reaction Scheme 1B above. Thus, compounds of type 1.10 can be prepared by reduction of an appropriate nitro analog, e.g., 1.9 as shown above. Appropriate nitro analogs are commercially available or prepared by methods known to one skilled in the art. The reduction reaction is carried out in the presence of an appropriate reducing agent, e.g., iron, and an appropriate hydride source, e.g., ammonium chloride, in an appropriate solvent system, e.g., ethanol and water. Compounds of type 1.12 can be prepared by a coupling reaction between an appropriate amine, e.g., 1.10 as shown above, and an appropriate acyl halide or carboxylic acid, e.g., 1.11 as shown above. Appropriate acyl halides and appropriate carboxylic acids are commercially available or prepared by methods known to one skilled in the art. The coupling reaction is carried out in the presence of an appropriate base, e.g., sodium bicarbonate, in an appropriate solvent, e.g., chloroform. Compounds of type 1.13 can be prepared by reduction of an appropriate ester, e.g., 1.12 as shown above. The reduction is carried out in the presence of an appropriate reducing agent, e.g., aqueous lithium hydroxide, in an appropriate solvent system, e.g., tetrahydrofuran and water. Compounds of type 1.15 can be prepared by a coupling reaction between an appropriate acyl halide or carboxylic acid, e.g., 1.13 as shown above, and an appropriate amine, e.g., 1.14 as shown above. Appropriate amines are commercially available or prepared by methods known to one skilled in the art. The coupling reaction is carried out in the presence of an appropriate coupling agent, e.g., e.g., 1-[Bis(dimethylamino)methylene]-1H-1,2,3-triazolo[4,5-b]pyridinium 3-oxid hexafluorophosphate (HATU), and an appropriate base, e.g., N,N-diisopropylethylamine (DIPEA), in an appropriate solvent, e.g., dimethylformamide. Compounds of type 1.16 can be prepared by reduction of an appropriate nitrile, e.g., 1.15 as shown above. The reduction is carried out in the presence of an appropriate reducing agent, e.g., Raney nickel, in an appropriate protic solvent, e.g., methanol. As can be appreciated by one skilled in the art, the above reaction provides an example of a generalized approach wherein compounds similar in structure to the specific reactants above (compounds similar to compounds of type 1.1, 1.2, 1.3, 1.4, 1.5, 1.6, and 1.7), can be substituted in the reaction to provide substituted phenyl analogs similar to Formula 1.8.

2. Route II

In one aspect, substituted piperidinyl analogs can be prepared as shown below.

SCHEME 2A.

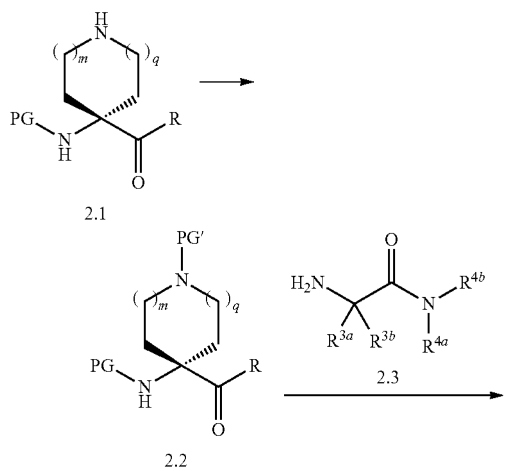

2.1, 2.2, 2.3

-continued

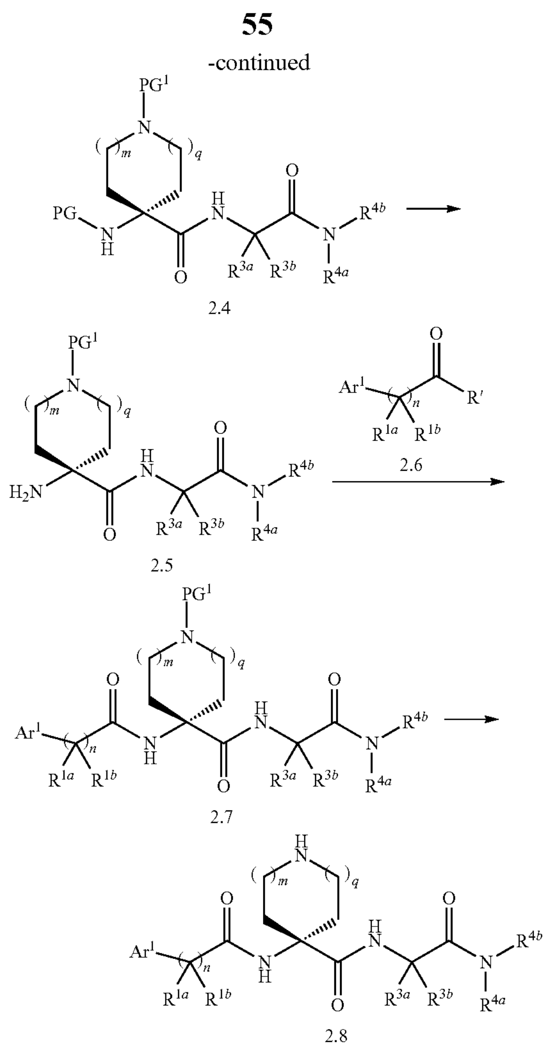

2.4

2.5

2.7

2.8

Compounds are represented in generic form, wherein each of R and R' is independently selected from halogen and —OH, wherein each of PG and PG' is independently an amine protecting group, and with other substituents as noted in compound descriptions elsewhere herein. A more specific example is set forth below.

SCHEME 2B.

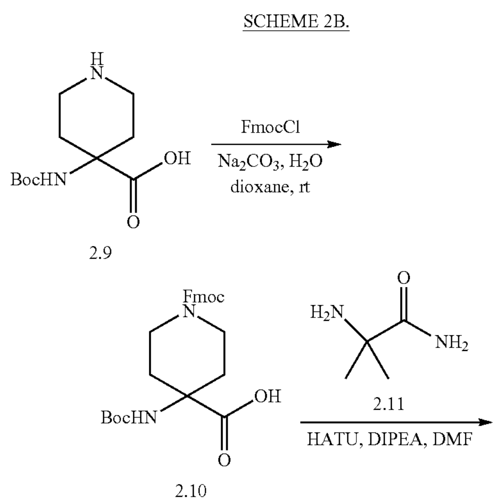

2.9

2.10

-continued

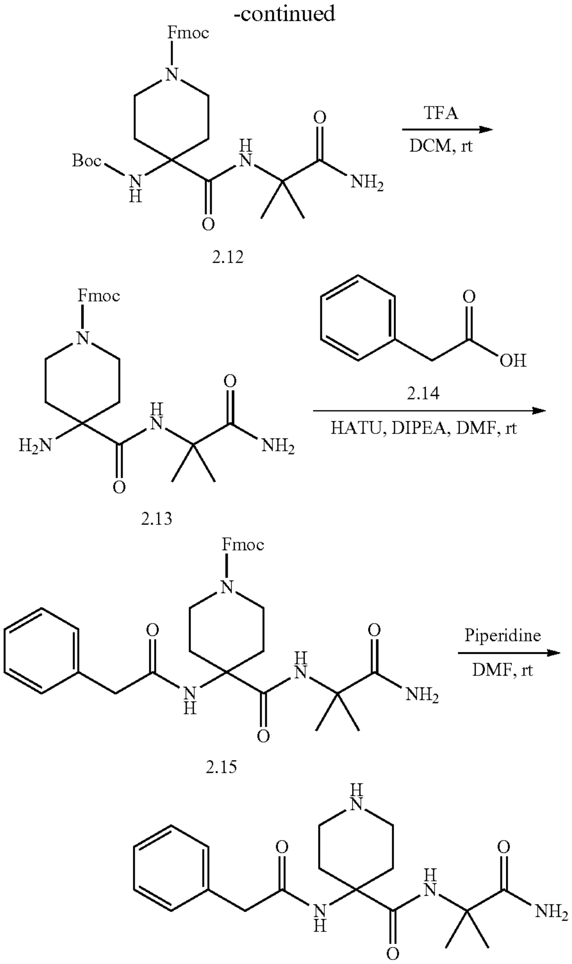

2.12

2.13

2.15

2.16

In one aspect, compounds of type 2.16, and similar compounds, can be prepared according to reaction Scheme 2B above. Thus, compounds of type 2.10 can be prepared by protection of an appropriate amine, e.g., 2.9 as shown above. Appropriate amines are commercially available or prepared by methods known to one skilled in the art. The protection is carried out in the presence of an appropriate protecting agent, e.g., fluorenylmethyloxycarbonyl chloride, and an appropriate base, e.g., aqueous sodium carbonate, in an appropriate solvent, e.g., dioxane. Compounds of type 2.12 can be prepared by a coupling reaction between an appropriate acyl halide or carboxylic acid, e.g., 2.10 as shown above, and an appropriate amine, e.g., 2.11 as shown above. Appropriate amines are commercially available or prepared by methods known to one skilled in the art. The coupling reaction is carried out in the presence of an appropriate coupling agent, e.g., e.g., 1-[Bis(dimethylamino)methylene]-1H-1,2,3-triazolo[4,5-b]pyridinium 3-oxid hexafluorophosphate (HATU), and an appropriate base, e.g., N,N-diisopropylethylamine (DIPEA), in an appropriate solvent, e.g., dimethylformamide. Compounds of type 2.13 can be prepared by deprotection of an appropriate primary amine, e.g., 2.12 as shown above. The deprotection is carried out in the presence of an appropriate deprotecting agent, e.g., trifluoacetic acid, in an appropriate solvent, e.g., dichloromethane. Compounds of type 2.15 can be prepared by a coupling reaction between an appropriate amine, e.g., 2.13 as shown above, and an appropriate acyl halide or carboxlic acid, e.g., 2.14 as shown above. Appropriate acyl halides and appropriate carboxylic acids are commercially available or prepared by methods known to one skilled in the art. The coupling reaction is carried out in the presence of an appropriate coupling agent, e.g., e.g., 1-[Bis(dimethylamino)methylene]-1H-1,2,3-triazolo[4,5-b]pyridinium 3-oxid hexafluorophosphate (HATU), and an appropriate base, e.g., N,N-diisopropylethylamine (DIPEA), in an appropriate solvent, e.g., dimethylformamide. Compounds of type 2.16 can be prepared by deprotection secondary amine, e.g., 2.15 as shown above. The deprotection is carried out in the presence of an appropriate deprotecting agent, e.g., piperidine, in an appropriate solvent, e.g., dimethylformamide. As can be appreciated by one skilled in the art, the above reaction provides an example of a generalized approach wherein compounds similar in structure to the specific reactants above (compounds similar to compounds of type 2.1, 2.2, 2.3, 2.4, 2.5, 2.6, and 2.7), can be substituted in the reaction to provide substituted piperidinyl analogs similar to Formula 2.8.

3. Route III

In one aspect, substituted heterocycloalkyl analogs can be prepared as shown below.

SCHEME 3A.

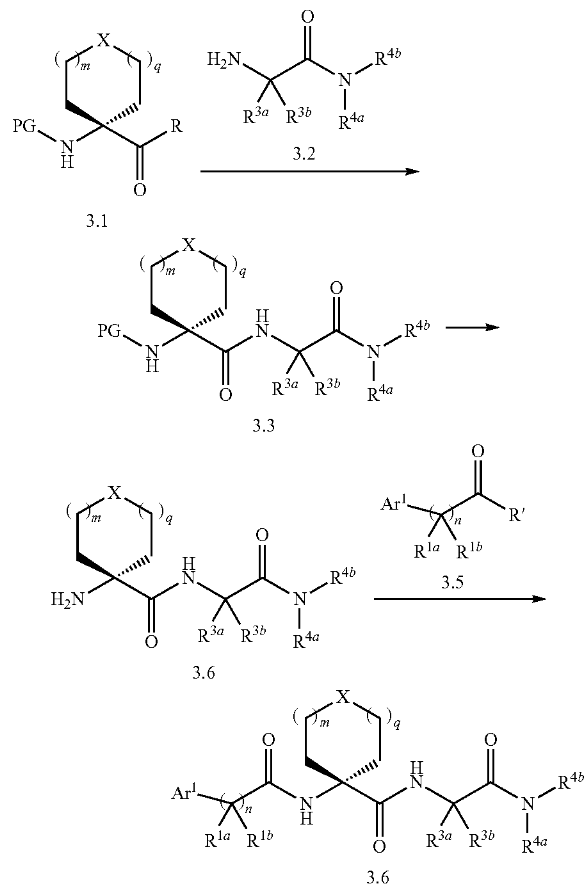

3.1 3.2 3.3 3.6 3.5 3.6

Compounds are represented in generic form, wherein each of R and R' is independently selected from halogen and —OH, wherein each of PG and PG' is independently an amine protecting group, and with other substituents as noted in compound descriptions elsewhere herein. A more specific example is set forth below.

SCHEME 3B.

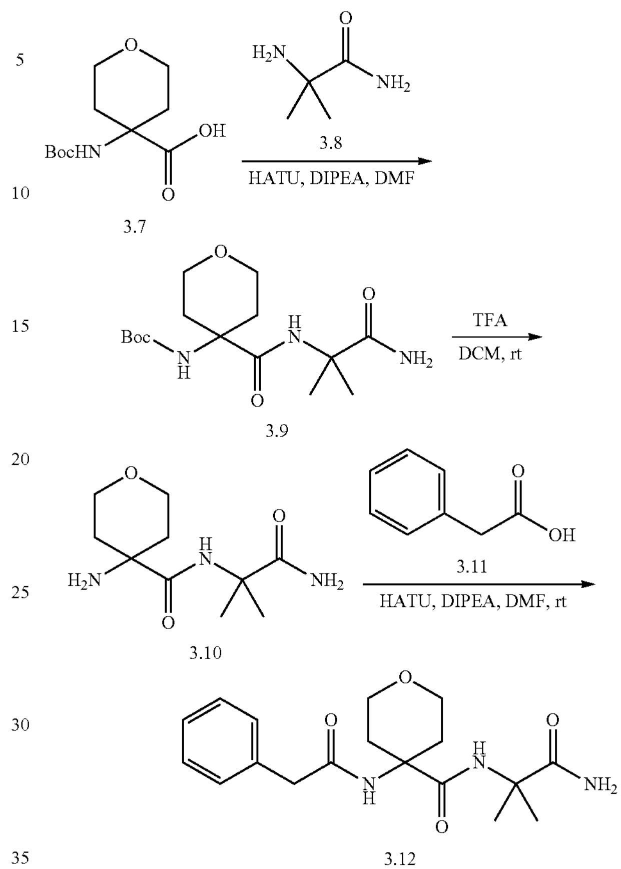

3.7 3.8 3.9 3.10 3.11 3.12

In one aspect, compounds of type 3.12, and similar compounds, can be prepared according to reaction Scheme 3B above. Thus, compounds of type 3.0 can be prepared by a coupling reaction between an appropriate acyl halide or carboxylic acid, e.g., 3.7 as shown above, and an appropriate amine, e.g., 3.8 as shown above. Appropriate amines are commercially available or prepared by methods known to one skilled in the art. The coupling reaction is carried out in the presence of an appropriate coupling agent, e.g., e.g., 1-[Bis(dimethylamino)methylene]-1H-1,2,3-triazolo[4,5-b] pyridinium 3-oxid hexafluorophosphate (HATU), and an appropriate base, e.g., N,N-diisopropylethylamine (DIPEA), in an appropriate solvent, e.g., dimethylformamide. Compounds of type 3.10 can be prepared by deprotection of an appropriate primary amine, e.g., 3.9 as shown above. The deprotection is carried out in the presence of an appropriate deprotecting agent, e.g., trifluoacetic acid, in an appropriate solvent, e.g., dichloromethane. Compounds of type 3.12 can be prepared by a coupling reaction between an appropriate amine, e.g., 3.10 as shown above, and an appropriate acyl halide or carboxlic acid, e.g., 3.11 as shown above. Appropriate acyl halides and appropriate carboxylic acids are commercially available or prepared by methods known to one skilled in the art. The coupling reaction is carried out in the presence of an appropriate coupling agent, e.g., e.g., 1-[Bis(dimethylamino)methylene]-1H-1,2,3-triazolo[4,5-b] pyridinium 3-oxid hexafluorophosphate (HATU), and an appropriate base, e.g., N,N-diisopropylethylamine (DIPEA), in an appropriate solvent, e.g., dimethylformamide. As can be appreciated by one skilled in the art, the above reaction provides an example of a generalized approach wherein compounds similar in structure to the specific reactants above (compounds similar to compounds of type 3.1, 3.2, 3.3, 3.4, and 3.5), can be substituted in the reaction to provide substituted heterocycloalkyl analogs similar to Formula 3.6.

E. Treating a Disorder of Uncontrolled Cellular Proliferation

In one aspect, disclosed are methods of treating a disorder of uncontrolled cellular proliferation in a subject, the method comprising the step of administering to the subject an effective amount of at least one disclosed compound, or a pharmaceutically acceptable salt thereof.

Thus, in one aspect, disclosed are methods for treating a disorder of uncontrolled cellular proliferation in a subject, the method comprising administering to the subject an effective amount of a compound having a structure represented by a formula selected from:

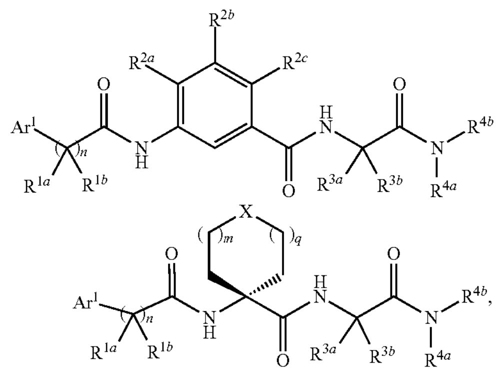

and wherein each of n, m, and q, when present, is independently selected from 0 and 1; wherein X, when present, is selected from —O—, —S—, —$NR^{10}$—, and —$CR^{12a}R^{12b}$; wherein $R^{10}$, when present, is selected from hydrogen and C1-C4 alkyl; wherein each of $R^{12a}$ and $R^{12b}$, when present, is independently selected from hydrogen and C1-C4 alkyl; wherein each of $R^{1a}$ and $R^{1b}$, when present, is independently selected from hydrogen, halogen, and C1-C4 alkyl; or wherein each of $R^{1a}$ and $R^{1b}$, when present, together comprise a C3-C6 cycloalkyl; wherein each of $R^{2a}$, $R^{2b}$, and $R^{2c}$, when present, is independently selected from hydrogen, halogen, and —$CH_2NR^{11a}R^{11b}$, provided that at least one of $R^{2a}$, $R^{2b}$, and $R^{2c}$ is —$CH_2NR^{11a}R^{11b}$; wherein each of $R^{11a}$ and $R^{11b}$, when present, is independently selected from hydrogen and C1-C4 alkyl; wherein each of $R^{3a}$ and $R^{3b}$ is independently selected from hydrogen and C1-C4 alkyl, or wherein each of $R^{3a}$ and $R^{3b}$ together comprise a C3-C6 cycloalkyl; wherein each of $R^{4a}$ and $R^{4b}$ is independently selected from hydrogen and C1-C4 alkyl; and wherein $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that when X is —$CR^{12a}R^{12b}$, then each of m and q is 1, or a pharmaceutically acceptable salt thereof.

In one aspect, disclosed are methods for treating a disorder of uncontrolled cellular proliferation in a subject, the method comprising administering to the subject an effective amount of a compound having a structure represented by a formula selected from:

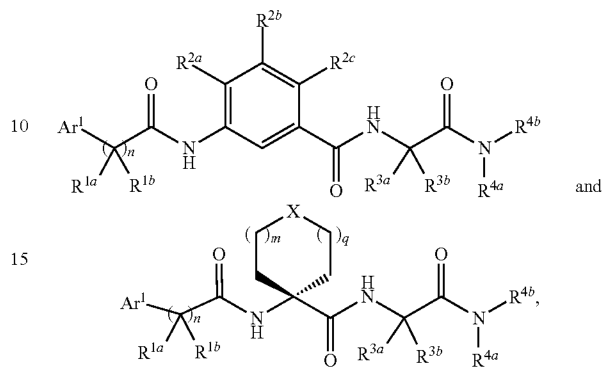

and wherein each of n, m, and q, when present, is independently selected from 0 and 1; wherein X, when present, is selected from —O—, —S—, and —$NR^{10}$—; wherein $R^{10}$, when present, is selected from hydrogen and C1-C4 alkyl; wherein each of $R^{1a}$ and $R^{1b}$, when present, is independently selected from hydrogen, halogen, and C1-C4 alkyl; or wherein each of $R^{1a}$ and $R^{1b}$, when present, together comprise a C3-C6 cycloalkyl; wherein each of $R^{2a}$, $R^{2b}$, and $R^{2c}$, when present, is independently selected from hydrogen, halogen, and —$CH_2NR^{11a}R^{11b}$, provided that at least one of $R^{2a}$, $R^{2b}$, and $R^{2c}$ is —$CH_2NR^{11a}R^{11b}$; wherein each of $R^{11a}$ and $R^{11b}$, when present, is independently selected from hydrogen and C1-C4 alkyl; wherein each of $R^{3a}$ and $R^{3b}$ is independently selected from hydrogen and C1-C4 alkyl, or wherein each of $R^{3a}$ and $R^{3b}$ together comprise a C3-C6 cycloalkyl; wherein each of $R^{4a}$ and $R^{4b}$ is independently selected from hydrogen and C1-C4 alkyl; and wherein $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, thereby treating the disorder.

In a further aspect, the subject has been diagnosed with a need for treatment of the disorder prior to the administering step.

In a further aspect, the subject is a mammal. In a still further aspect, the mammal is a human.

In a further aspect, the method further comprises the step of identifying a subject in need of treatment of the disorder.

In a further aspect, the disorder is a cancer. In a still further aspect, the cancer is selected from a sarcoma, a carcinoma, a hematological cancer, a solid tumor, breast cancer, cervical cancer, gastrointestinal cancer, colorectal cancer, brain cancer, skin cancer, prostate cancer, ovarian cancer, thyroid cancer, testicular cancer, pancreatic cancer, liver cancer, endometrial cancer, melanoma, a glioma, leukemia, lymphoma, chronic myeloproliferative disorder, myelodysplastic syndrome, myeloproliferative neoplasm, non-small cell lung carcinoma, and plasma cell neoplasm (myeloma).

In a further aspect, the cancer is a solid tumor.

In a further aspect, the effective amount is a therapeutically effective amount.

In a still further aspect, the effective amount is a prophylactically effective amount.

In a further aspect, the method further comprises the step of administering a therapeutically effective amount of at least one agent associated with the treatment of a disorder of uncontrolled cellular proliferation. In a still further aspect, the at least one agent is a chemotherapeutic agent. In yet a further aspect, the chemotherapeutic agent is selected from an alkylating agent, an antimetabolite agent, an antineoplastic antibiotic agent, a mitotic inhibitor agent, and a mTor inhibitor agent.

In various aspects, the antineoplastic antibiotic agent is selected from doxorubicin, mitoxantrone, bleomycin, daunorubicin, dactinomycin, epirubicin, idarubicin, plicamycin, mitomycin, pentostatin, and valrubicin, or a pharmaceutically acceptable salt thereof.

In various aspects, the antimetabolite agent is selected from gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt thereof.

In various aspects, the alkylating agent is selected from carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt thereof.

In various aspects, the mitotic inhibitor agent is selected from irinotecan, topotecan, rubitecan, cabazitaxel, docetaxel, paclitaxel, etopside, vincristine, ixabepilone, vinorelbine, vinblastine, and teniposide, or a pharmaceutically acceptable salt thereof.

In various aspects, the mTor inhibitor agent is selected from everolimus, siroliumus, and temsirolimus, or a pharmaceutically acceptable salt, hydrate, solvate, or polymorph thereof.

In a further aspect, the at least one compound and the at least one agent are administered sequentially. In a still further aspect, the at least one compound and the at least one agent are administered simultaneously.

In a further aspect, the at least one compound and the at least one agent are co-formulated. In a still further aspect, the at least one compound and the at least one agent are co-packaged.

F. Modifying Programmed Death-Ligand-1 Signaling in a Subject

In one aspect, disclosed are methods of modifying PDL-1 signaling in a subject, the method comprising the step of administering to the subject an effective amount of at least one disclosed compound, or a pharmaceutically acceptable salt thereof.

Thus, in one aspect, disclosed are methods for modifying programmed death-ligand-1 (PDL-1) signaling in a subject, the method comprising administering to the subject an effective amount of a compound having a structure represented by a formula selected from:

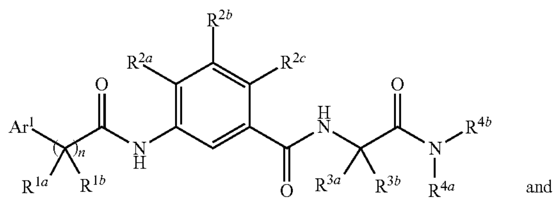

and

-continued

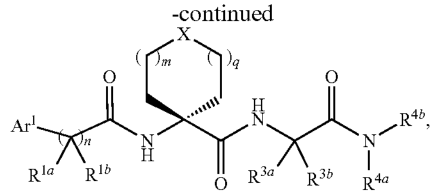

wherein each of n, m, and q, when present, is independently selected from 0 and 1; wherein X, when present, is selected from —O—, —S—, —$NR^{10}$—, and —$CR^{12a}R^{12b}$; wherein $R^{10}$, when present, is selected from hydrogen and C1-C4 alkyl; wherein each of $R^{12a}$ and $R^{12b}$, when present, is independently selected from hydrogen and C1-C4 alkyl; wherein each of $R^{1a}$ and $R^{1b}$, when present, is independently selected from hydrogen, halogen, and C1-C4 alkyl; or wherein each of $R^{1a}$ and $R^{1b}$, when present, together comprise a C3-C6 cycloalkyl; wherein each of $R^{2a}$, $R^{2b}$, and $R^{2c}$, when present, is independently selected from hydrogen, halogen, and —$CH_2NR^{11a}R^{11b}$, provided that at least one of $R^{2a}$, $R^{2b}$, and $R^{2c}$ is —$CH_2NR^{11a}R^{11b}$; wherein each of $R^{11a}$ and $R^{11b}$, when present, is independently selected from hydrogen and C1-C4 alkyl; wherein each of $R^{3a}$ and $R^{3b}$ is independently selected from hydrogen and C1-C4 alkyl, or wherein each of $R^{3a}$ and $R^{3b}$ together comprise a C3-C6 cycloalkyl; wherein each of $R^{4a}$ and $R^{4b}$ is independently selected from hydrogen and C1-C4 alkyl; and wherein $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that when X is —$CR^{12a}R^{12b}$, then each of m and q is 1, or a pharmaceutically acceptable salt thereof, thereby modifying PDL-1 signaling in the subject.

In one aspect, disclosed are methods for modifying PDL-1 signaling in a subject, the method comprising administering to the subject an effective amount of a compound having a structure represented by a formula selected from:

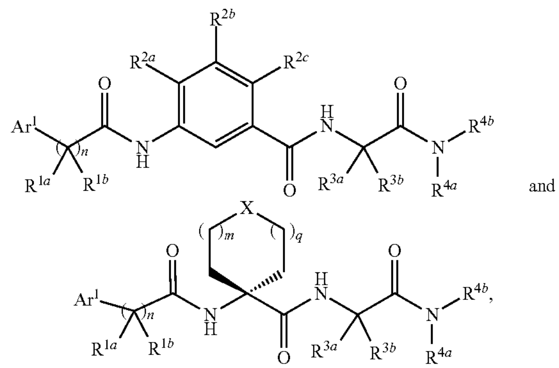

and wherein each of n, m, and q, when present, is independently selected from 0 and 1; wherein X, when present, is selected from —O—, —S—, and —$NR^{10}$—; wherein $R^{10}$, when present, is selected from hydrogen and C1-C4 alkyl; wherein each of $R^{1a}$ and $R^{1b}$, when present, is independently selected from hydrogen, halogen, and C1-C4 alkyl; or wherein each of $R^{1a}$ and $R^{1b}$, when present, together comprise a C3-C6 cycloalkyl; wherein each of $R^{2a}$, $R^{2b}$, and $R^{2c}$, when present, is independently selected from hydrogen, halogen, and —$CH_2NR^{11a}R^{11b}$, provided that at least one of $R^{2a}$, $R^{2b}$, and $R^{2c}$ is —$CH_2NR^{11a}R^{11b}$; wherein each of $R^{11a}$ and $R^{11b}$, when present, is independently selected from hydrogen and C1-C4 alkyl; wherein each of $R^{3a}$ and $R^{3b}$ is independently selected from hydrogen and C1-C4 alkyl, or wherein each of $R^{3a}$ and $R^{3b}$ together comprise a C3-C6 cycloalkyl; wherein each of $R^{4a}$ and $R^{4b}$ is independently selected from hydrogen and C1-C4 alkyl; and wherein $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, thereby modifying PDL-1 signaling in the subject.

In a further aspect, modifying is decreasing. In a still further aspect, modifying is inhibiting.

In a further aspect, the subject has been diagnosed with a disorder of uncontrolled cellular proliferation prior to the administering step.

In a further aspect, the subject has been diagnosed with a need for modifying PDL-1 signaling prior to the administering step.

In a further aspect, the subject has been diagnosed with a need for treatment of a disorder associated with PDL-1 signaling dysfunction prior to the administering step.

In a further aspect, the method further comprises the step of identifying a subject in need of treatment of a disorder associated with PDL-1 signaling dysfunction.

G. Modifying Programmed Death-Ligand-1 in at Least One Cell

In one aspect, disclosed are methods of modifying PDL-1 signaling in a cell, the method comprising the step of contacting the cell with an effective amount of at least one disclosed compound, or a pharmaceutically acceptable salt thereof.

Thus, in one aspect, disclosed are methods for modifying PDL-1 signaling in a cell, the method comprising contacting the cell with an effective amount of a compound having a structure represented by a formula selected from:

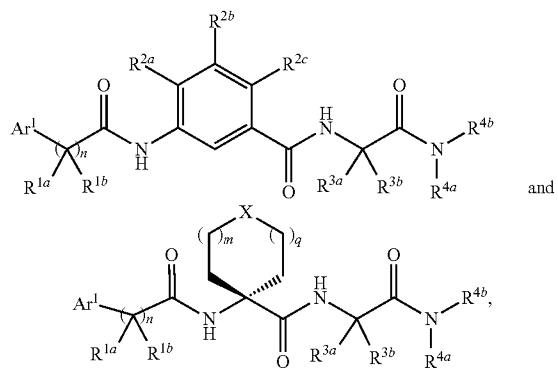

and wherein each of n, m, and q, when present, is independently selected from 0 and 1; wherein X, when present, is selected from —O—, —S—, —$NR^{10}$—, and —$CR^{12a}R^{12b}$; wherein $R^{10}$, when present, is selected from hydrogen and C1-C4 alkyl; wherein each of $R^{12a}$ and $R^{12b}$, when present, is independently selected from hydrogen and C1-C4 alkyl; wherein each of $R^{1a}$ and $R^{1b}$, when present, is independently selected from hydrogen, halogen, and C1-C4 alkyl; or wherein each of $R^{1a}$ and $R^{1b}$, when present, together comprise a C3-C6 cycloalkyl; wherein each of $R^{2a}$, $R^{2b}$, and $R^{2c}$, when present, is independently selected from hydrogen, halogen, and —$CH_2NR^{11a}R^{11b}$, provided that at least one of $R^{2a}$, $R^{2b}$, and $R^{2c}$ is —$CH_2NR^{11a}R^{11b}$; wherein each of $R^{11a}$ and $R^{11b}$, when present, is independently selected from hydrogen and C1-C4 alkyl; wherein each of $R^{3a}$ and $R^{3b}$ is independently selected from hydrogen and C1-C4 alkyl, or wherein each of $R^{3a}$ and $R^{3b}$ together comprise a C3-C6 cycloalkyl; wherein each of $R^{4a}$ and $R^{4b}$ is independently selected from hydrogen and C1-C4 alkyl; and wherein $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that when X is —$CR^{12a}R^{12b}$, then each of m and q is 1, or a pharmaceutically acceptable salt thereof, thereby modifying PDL-1 signaling in the cell.

In one aspect, disclosed are methods for modifying PDL-1 signaling in a cell, the method comprising contacting the cell with an effective amount of a compound having a structure represented by a formula selected from:

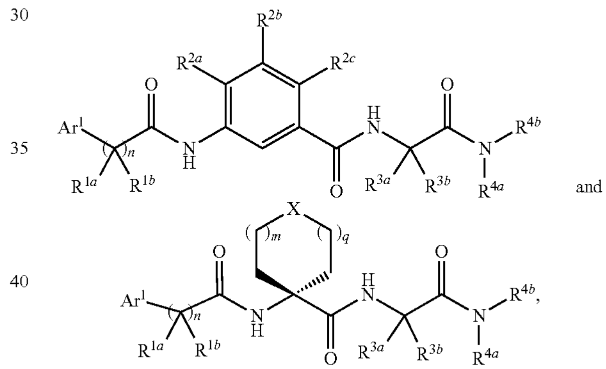

and wherein each of n, m, and q, when present, is independently selected from 0 and 1; wherein X, when present, is selected from —O—, —S—, and —$NR^{10}$—; wherein $R^{10}$, when present, is selected from hydrogen and C1-C4 alkyl; wherein each of $R^{1a}$ and $R^{1b}$, when present, is independently selected from hydrogen, halogen, and C1-C4 alkyl; or wherein each of $R^{1a}$ and $R^{1b}$, when present, together comprise a C3-C6 cycloalkyl; wherein each of $R^{2a}$, $R^{2b}$, and $R^{2c}$, when present, is independently selected from hydrogen, halogen, and —$CH_2NR^{11a}R^{11b}$, provided that at least one of $R^{2a}$, $R^{2b}$, and $R^{2c}$ is —$CH_2NR^{11a}R^{11b}$; wherein each of $R^{11a}$ and $R^{11b}$, when present, is independently selected from hydrogen and C1-C4 alkyl; wherein each of $R^{3a}$ and $R^{3b}$ is independently selected from hydrogen and C1-C4 alkyl, or wherein each of $R^{3a}$ and $R^{3b}$ together comprise a C3-C6 cycloalkyl; wherein each of $R^{4a}$ and $R^{4b}$ is independently selected from hydrogen and C1-C4 alkyl; and wherein $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-

C4) dialkylamino, and C1-C4 aminoalkyl, or a pharmaceutically acceptable salt thereof, thereby modifying PDL-1 signaling in the cell.

In a further aspect, modifying is decreasing. In a still further aspect, modifying is inhibiting.

In a further aspect, the cell is mammalian. In a still further aspect, the cell is human.

In a further aspect, the cell has been isolated from a human prior to the administering step.

In a further aspect, contacting is via administration to a subject. In a still further aspect, the subject has been diagnosed with a need for modification of PDL-1 signaling prior to the administering step. In yet a further aspect, the subject has been diagnosed with a need for treatment of a disorder associated with PDL-1 signaling dysfunction.

H. Additional Methods of Using the Compounds

The compounds and pharmaceutical compositions of the invention are useful in treating or controlling disorders associated with uncontrolled cellular proliferation and in particular, cancer.

Examples of disorders of uncontrolled cellular proliferation for which the compounds and compositions can be useful in treating, include, but are not limited to, cancers such as, for example, sarcomas, carcinomas, hematological cancers, solid tumors, breast cancer, cervical cancer, gastrointestinal cancer, colorectal cancer, brain cancer, skin cancer, prostate cancer, ovarian cancer, bladder cancer, thyroid cancer, testicular cancer, pancreatic cancer, endometrial cancer, melanomas, gliomas, leukemias, lymphomas, chronic myeloproliferative disorders, myelodysplastic syndromes, myeloproliferative neoplasms, and plasma cell neoplasms (myelomas).

To treat or control the disorder, the compounds and pharmaceutical compositions comprising the compounds are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. The subject is preferably a mammal, such as a human. Prior to administering the compounds or compositions, the subject can be diagnosed with a need for treatment of a disorder of uncontrolled cellular proliferation, such as cancer.

The compounds or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a disorder of uncontrolled cellular proliferation, such as cancer.

The therapeutically effective amount or dosage of the compound can vary within wide limits. Such a dosage is adjusted to the individual requirements in each particular case including the specific compound(s) being administered, the route of administration, the condition being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

1. Use of Compounds

In one aspect, the invention relates to the use of a disclosed compound or a product of a disclosed method. In a further aspect, a use relates to the manufacture of a medicament for the treatment of a disorder of uncontrolled cellular proliferation in a subject.

Also provided are the uses of the disclosed compounds and products. In one aspect, the invention relates to use of at least one disclosed compound; or a pharmaceutically acceptable salt, hydrate, solvate, or polymorph thereof. In a further aspect, the compound used is a product of a disclosed method of making.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In various aspects, the use relates to a treatment of a disorder of uncontrolled cellular proliferation in a subject. In one aspect, the use is characterized in that the subject is a human. In one aspect, the use is characterized in that the disorder of uncontrolled cellular proliferation is a cancer.

In a further aspect, the use relates to the manufacture of a medicament for the treatment of a disorder of uncontrolled cellular proliferation in a subject.

It is understood that the disclosed uses can be employed in connection with the disclosed compounds, products of disclosed methods of making, methods, compositions, and kits. In a further aspect, the invention relates to the use of a disclosed compound or a disclosed product in the manufacture of a medicament for the treatment of a disorder of uncontrolled cellular proliferation in a mammal. In a further aspect, the disorder of uncontrolled cellular proliferation is a cancer.

2. Manufacture of a Medicament

In one aspect, the invention relates to a method for the manufacture of a medicament for treating a disorder of uncontrolled cellular proliferation in a subject having the disorder, the method comprising combining a therapeutically effective amount of a disclosed compound or product of a disclosed method with a pharmaceutically acceptable carrier or diluent.

As regards these applications, the present method includes the administration to an animal, particularly a mammal, and more particularly a human, of a therapeutically effective amount of the compound effective in the treatment of a disorder of uncontrolled cellular proliferation. The dose administered to an animal, particularly a human, in the context of the present invention should be sufficient to affect a therapeutic response in the animal over a reasonable time frame. One skilled in the art will recognize that dosage will depend upon a variety of factors including the condition of the animal and the body weight of the animal.

The total amount of the compound of the present disclosure administered in a typical treatment is preferably between about 0.05 mg/kg and about 100 mg/kg of body weight for mice, and more preferably between 0.05 mg/kg and about 50 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

3. Kits

In one aspect, disclosed are kits comprising an effective amount of a disclosed compound, and one or more of: (a) at least one agent associated with the treatment of a disorder of uncontrolled cellular proliferation; (b) instructions for administering the compound in connection with treating a disorder of uncontrolled cellular proliferation; and (c) instructions for treating a disorder of uncontrolled cellular proliferation.

Thus, in one aspect, disclosed are kits comprising a compound having a structure represented by a formula selected from:

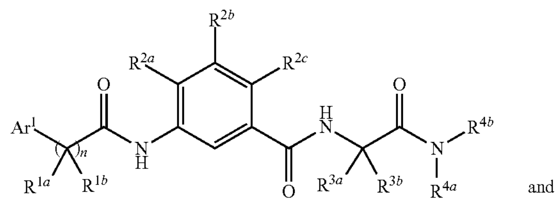

and

-continued

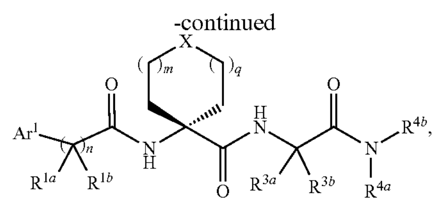

wherein each of n, m, and q, when present, is independently selected from 0 and 1; wherein X, when present, is selected from —O—, —S—, —$NR^{10}$—, and —$CR^{12a}R^{12b}$; wherein $R^{10}$, when present, is selected from hydrogen and C1-C4 alkyl; wherein each of $R^{12a}$ and $R^{12b}$, when present, is independently selected from hydrogen and C1-C4 alkyl; wherein each of $R^{1a}$ and $R^{1b}$, when present, is independently selected from hydrogen, halogen, and C1-C4 alkyl; or wherein each of $R^{1a}$ and $R^{1b}$, when present, together comprise a C3-C6 cycloalkyl; wherein each of $R^{2a}$, $R^{2b}$, and $R^{2c}$, when present, is independently selected from hydrogen, halogen, and —$CH_2NR^{11a}R^{11b}$, provided that at least one of $R^{2a}$, $R^{2b}$, and $R^{2c}$ is —$CH_2NR^{11a}R^{11b}$; wherein each of $R^{11a}$ and $R^{11b}$, when present, is independently selected from hydrogen and C1-C4 alkyl; wherein each of $R^{3a}$ and $R^{3b}$ is independently selected from hydrogen and C1-C4 alkyl, or wherein each of $R^{3a}$ and $R^{3b}$ together comprise a C3-C6 cycloalkyl; wherein each of $R^{4a}$ and $R^{4b}$ is independently selected from hydrogen and C1-C4 alkyl; and wherein $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that when X is —$CR^{12a}R^{12b}$, then each of m and q is 1, or a pharmaceutically acceptable salt thereof, and one or more of: (a) at least one agent associated with the treatment of a disorder of uncontrolled cellular proliferation; (b) instructions for administering the compound in connection with treating a disorder of uncontrolled cellular proliferation; and (c) instructions for treating a disorder of uncontrolled cellular proliferation.

In one aspect, disclosed are kits comprising an effective amount of a compounds having a structure represented by a formula selected from:

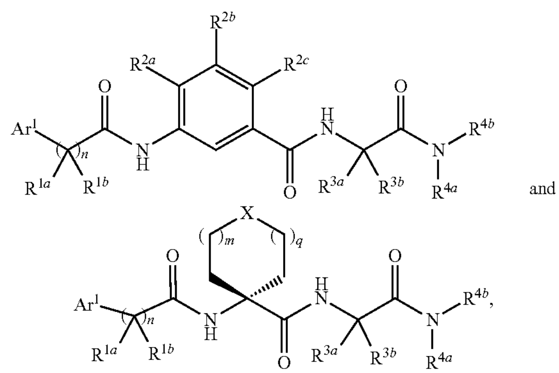

and wherein each of n, m, and q, when present, is independently selected from 0 and 1; wherein X, when present, is selected from —O—, —S—, and —$NR^{10}$—; wherein $R^{10}$, when present, is selected from hydrogen and C1-C4 alkyl; wherein each of $R^{1a}$ and $R^{1b}$, when present, is independently selected from hydrogen, halogen, and C1-C4 alkyl; or wherein each of $R^{1a}$ and $R^{1b}$, when present, together comprise a C3-C6 cycloalkyl; wherein each of $R^{2a}$, $R^{2b}$, and $R^{2c}$, when present, is independently selected from hydrogen, halogen, and —$CH_2NR^{11a}R^{11b}$, provided that at least one of $R^{2a}$, $R^{2b}$, and $R^{2c}$ is —$CH_2NR^{11a}R^{11b}$; wherein each of $R^{11a}$ and $R^{11b}$, when present, is independently selected from hydrogen and C1-C4 alkyl; wherein each of $R^{3a}$ and $R^{3b}$ is independently selected from hydrogen and C1-C4 alkyl, or wherein each of $R^{3a}$ and $R^{3b}$ together comprise a C3-C6 cycloalkyl; wherein each of $R^{4a}$ and $R^{4b}$ is independently selected from hydrogen and C1-C4 alkyl; and wherein $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, and one or more of: (a) at least one agent associated with the treatment of a disorder of uncontrolled cellular proliferation; (b) instructions for administering the compound in connection with treating a disorder of uncontrolled cellular proliferation; and (c) instructions for treating a disorder of uncontrolled cellular proliferation.

In a further aspect, the disorder is a cancer. In a still further aspect, the cancer is selected from a sarcoma, a carcinoma, a hematological cancer, a solid tumor, breast cancer, cervical cancer, gastrointestinal cancer, colorectal cancer, brain cancer, skin cancer, prostate cancer, ovarian cancer, thyroid cancer, testicular cancer, pancreatic cancer, liver cancer, endometrial cancer, melanoma, a glioma, leukemia, lymphoma, chronic myeloproliferative disorder, myelodysplastic syndrome, myeloproliferative neoplasm, non-small cell lung carcinoma, and plasma cell neoplasm (myeloma).

In a further aspect, the cancer is a solid tumor.

In a further aspect, the agent is a chemotherapeutic agent. In yet a further aspect, the chemotherapeutic agent is selected from an alkylating agent, an antimetabolite agent, an antineoplastic antibiotic agent, a mitotic inhibitor agent, and a mTor inhibitor agent.

In various aspects, the antineoplastic antibiotic agent is selected from doxorubicin, mitoxantrone, bleomycin, daunorubicin, dactinomycin, epirubicin, idarubicin, plicamycin, mitomycin, pentostatin, and valrubicin, or a pharmaceutically acceptable salt thereof.

In various aspects, the antimetabolite agent is selected from gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt thereof.

In various aspects, the alkylating agent is selected from carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt thereof.

In various aspects, the mitotic inhibitor agent is selected from irinotecan, topotecan, rubitecan, cabazitaxel, docetaxel, paclitaxel, etopside, vincristine, ixabepilone, vinorelbine, vinblastine, and teniposide, or a pharmaceutically acceptable salt thereof.

In various aspects, the mTor inhibitor agent is selected from everolimus, siroliumus, and temsirolimus, or a pharmaceutically acceptable salt, hydrate, solvate, or polymorph thereof.

In a further aspect, the compound and the agent are co-formulated. In a further aspect, the compound and the agent are co-packaged.

In a further aspect, the compound and the agent are administered sequentially. In a still further aspect, the compound and the agent are administered simultaneously.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

I. Examples

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Chemistry Experimentals

All reactions were carried out in an oven- or flame-dried glassware under argon atmosphere using standard gas-tight syringe, cannula, and septa. The reaction temperatures were measured externally. Stirring was achieved with oven dried magnetic bars. All the reactions were done in anhydrous solvents (DMF, MeCN, $CH_2Cl_2$) purchased from Sigma-Aldrich. All commercially purchased reagents were used without purification. The reactions were monitored by thin-layer chromatography (TLC) on a pre-coated silica gel (60 F254) glass/aluminum plates from EMD Millipore and visualized using UV light (254 nm). Purification of the compounds was performed on Teledyne-ISCO Combiflash Rf 200 purification system by using Redisep Rf® normal phase silica gel columns 230-400 mesh. Proton NMR spectra were recorded on a Varian Unity 400 NMR spectrometer operating at 400 MHz calibrated to the solvent peak and TMS peak. The chemical formula and Exact Mass for target compounds were determined from the $(M+H)^+$ by high resolution mass spectroscopy using an Agilent 6210 Electrospray Time of Flight. ESI-MS spectra were recorded on a BioTof-2 time-of-flight mass spectrometer.

a. Representative Synthesis of Phenyl Analogs—Synthesis of Compound No. 1

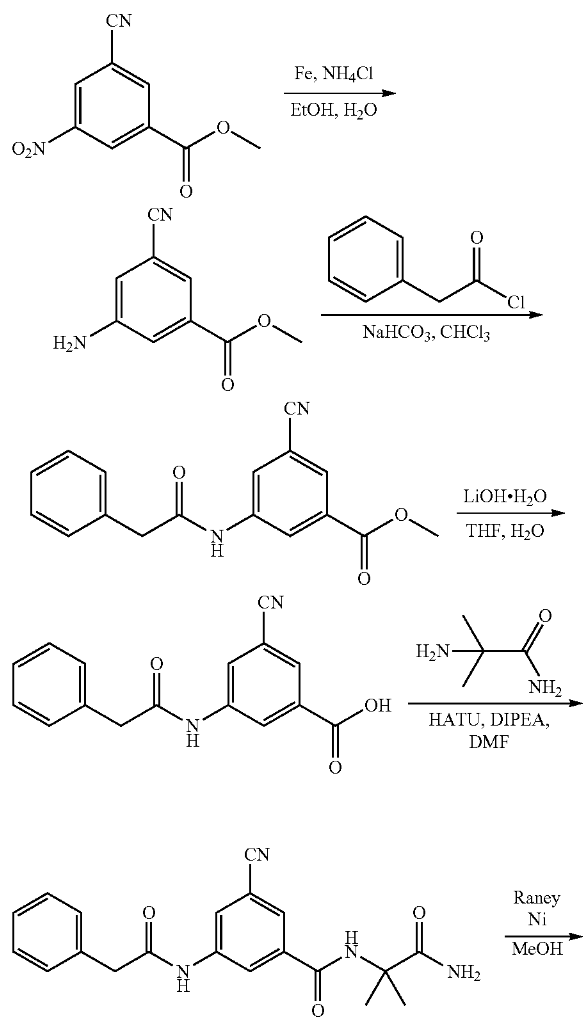

-continued

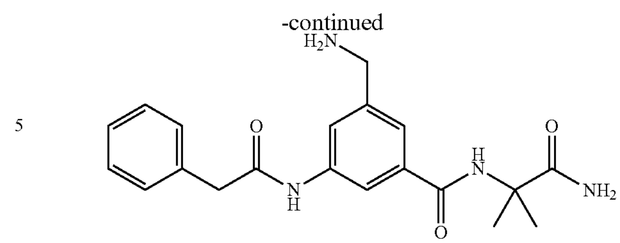

Methyl 3-amino-5-cyanobenzoate. A solution of methyl 3-cyano-5-nitrobenzoate (2.00 g, 9.70 mmol) and $NH_4Cl$ (5.19 g, 97.0 mmol) in EtOH (100 mL) and $H_2O$ (20.0 mL) was added iron powder (5.43 g) at room temperature. The resulting solution was stirred at 80° C. for 1 h. The reaction mixture was diluted with EtOAc. Then the solid was filtered out. The filtrate was quenched with water and extracted with EtOAc. The organic layer was dried over anhydrous sodium sulfate and concentrated under vacuum. The residue was purified by flash chromatography on silica gel eluting with EtOAc/petroleum ether (0%-70%) to afford methyl 3-amino-5-cyanobenzoate (1.50 g, 87.7%) as a light yellow solid. H-NMR-PH-SRE-I001-007-1: $^1H$ NMR (300 MHz, DMSO-$d_6$) δ 7.46 (s, 1H), 7.35 (s, 1H), 7.13-7.06 (s, 1H), 5.81 (s, 2H), 3.84 (s, 3H).

Methyl 3-cyano-5-(2-phenylacetamido)benzoate. A solution of methyl 3-amino-5-cyanobenzoate (700 mg, 3.97 mmol) and $NaHCO_3$ (667 mg, 7.94 mmol) in $CHCl_3$ (20.0 mL) was added phenylacetyl chloride (737 mg, 4.77 mmol) at room temperature. The resulting solution was stirred at room temperature for 2 h. The reaction mixture was quenched with water and extracted with DCM. The organic layer was dried over anhydrous sodium sulfate and concentrated under vacuum. The residue was purified by flash chromatography on silica gel eluting with EtOAc/petroleum ether (0%-80%) to afford methyl 3-cyano-5-(2-phenylacetamido)benzoate (800 mg, 68.4%) as an off-white solid. LCMS: m/z=295 $[M+H]^+$.

3-Cyano-5-(2-phenylacetamido)benzoic acid. A solution of methyl 3-cyano-5-(2-phenylacetamido)benzoate (700 mg, 2.38 mmol) in THF (10.0 mL) was added $LiOH \cdot H_2O$ (120 mg, 2.86 mmol) in $H_2O$ (3.00 mL) at room temperature. The resulting solution was stirred at room temperature for 3 h. The reaction mixture was acidified to pH 5-6 with diluted hydrochloric acid (1M). Then the solvent was concentrated under vacuum. The crude solid was re-dissolved in DMF and purified by reverse phase flash chromatography eluting with ACN/water (0%-30%, acidic system) to afford 3-cyano-5-(2-phenylacetamido)benzoic acid (500 mg, 75.0%) as a white solid. LCMS: m/z=281 $[M+H]^+$.

2-[[3-Cyano-5-(2-phenylacetamido)phenyl]formamido]-2-methylpropanamide. A solution of 3-cyano-5-(2-phenylacetamido)benzoic acid (450 mg, 1.61 mmol), 2-amino-2-methylpropanamide (197 mg, 1.93 mmol) and HATU (733 mg, 1.93 mmol) in DMF (10.0 mL, 12.9 mmol) was added DIPEA (415 mg, 3.21 mmol) and stirred at room temperature for 0.5 h. The reaction mixture was quenched with water, extracted with EtOAc and washed with brine. The organic layer was dried over anhydrous sodium sulfate and concentrated under vacuum. The residue was purified by flash chromatography on silica gel eluting with MeOH/DCM (0%-20%) to afford 2-[[3-cyano-5-(2-phenylacetamido)phenyl]formamido]-2-methylpropanamide (480 mg, 82.0%) as a white solid. LCMS: m/z=365 $[M+H]^+$.

2-[[3-(Aminomethyl)-5-(2-phenylacetamido)phenyl]formamido]-2-methylpropanamide (1, SRI-43234). Under hydrogen, a solution of 2-[[3-cyano-5-(2-phenylacetamido) phenyl]formamido]-2-methylpropanamide (100 mg, 0.274 mmol) in methanol (20.0 mL) was added Raney Ni (50.2 mg, 0.586 mmol) at room temperature. The resulting solution was stirred at room temperature for 4 h. The solid was filtered out and the filtrate was concentrated under vacuum. The residue was purified by reverse phase flash chromatography eluting with ACN/water (0%-40%, neutral system) to afford 2-[[3-(aminomethyl)-5-(2-phenylacetamido)phenyl] formamido]-2-methylpropanamide (30.1 mg, 29.8%) as a white solid. LCMS: m/z=369[M+H]$^+$. $^1$H NMR (400 MHz, Methanol-$d_4$): δ 7.88-7.86 (m, 1H), 7.74-7.72 (m, 1H), 7.57-7.55 (m, 1H), 7.39-7.32 (m, 4H), 7.29-7.24 (m, 1H), 3.88 (s, 2H), 3.72 (s, 2H), 1.61 (s, 6H).

Phenyl analogs 2-21 were synthesized by following the above synthetic procedures.

b. Representative Synthesis of Heterocycloalkyl Analogs—Synthesis of Compound No. 22

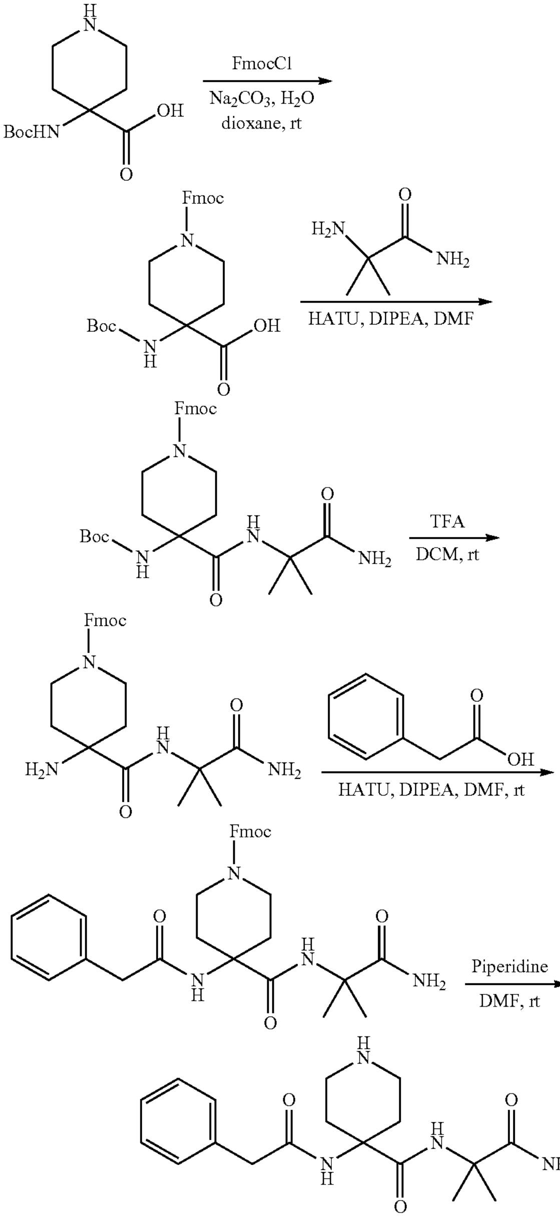

A 4-[(tert-Butoxycarbonyl)amino]-1-[(9H-fluoren-9-ylmethoxy)carbonyl]piperidine-4-carboxylic acid. To a solution of 4-[(tert-butoxycarbonyl)amino]piperidine-4-carboxylic acid (500.0 mg, 2.047 mmol) in dioxane (8.0 mL) was added a solution of Na2CO3 (282.1 mg, 2.661 mmol) in H2O (8.0 mL) and was stirred for 30 min at 25° C. Then fluorenylmethyloxycarbonyl chloride (582.4 mg, 2.251 mmol) was added and was stirred for 1 overnight at 25° C. The resulting solution was diluted with 20 mL of $H_2O$. The resulting solution was extracted with EtOAc. The pH value of the solution was adjusted to 3 with HCl (1 mmol/L). The solids were collected by filtration. This resulted in 858 mg (89%) of 4-[(tert-butoxycarbonyl)amino]-1-[(9H-fluoren-9-ylmethoxy)carbonyl]piperidine-4-carboxylic acid as a white solid. LCMS (ESI): [M+H]$^+$-467.

9H-fluoren-9-ylmethyl 4-[(tert-butoxycarbonyl)amino]-4-[(1-carbamoyl-1-methylethyl)carbamoyl]piperidine-1-carboxylate. To a solution of placed 4-[(tert-butoxycarbonyl)amino]-1-[(9H-fluoren-9-ylmethoxy)carbonyl] piperidine-4-carboxylic acid (700.0 mg, 1.500 mmol), 2-amino-2-methylpropanamide 2,2,2-trifluoroacetate (389.2 mg, 1.801 mmol) and DIPEA (775.7 mg, 6.002 mmol) in DMF (5.0 mL) was added HATU (684.6 mg, 1.801 mmol) and was stirred for 1 h at 25° C. The residue was purified by reverse phase with 0.05% TFA of water/ACN (1:1). This resulted in 803 mg (97%) of 9H-fluoren-9-ylmethyl 4-[(tert-butoxycarbonyl)amino]-4-[(1-carbamoyl-1-methylethyl) carbamoyl]piperidine-1-carboxylate as a white solid. LCMS (ESI): [M+H]$^+$-551.

9H-fluoren-9-ylmethyl 4-amino-4-[(1-carbamoyl-1-methylethyl)carbamoyl]piperidine-1-carboxylate. To a solution of 9H-fluoren-9-ylmethyl 4-[(tert-butoxycarbonyl) amino]-4-[(1-carbamoyl-1-methylethyl)carbamoyl] piperidine-1-carboxylate (803.0 mg, 1.458 mmol) in DCM (2.0 mL) was added $CF_3COOH$ (1.0 mL) and was stirred for 1 h at 25° C. The residue was purified by reverse phase with 0.05% TFA of water/ACN (8:2). This resulted in 601 mg (91%) of 9H-fluoren-9-ylmethyl 4-amino-4-[(1-carbamoyl-1-methylethyl)carbamoyl]piperidine-1-carboxylate as a white solid. LCMS (ESI): [M+H]$^+$=451.

9H-fluoren-9-ylmethyl 4-[(1-carbamoyl-1-methylethyl) carbamoyl]-4-(2-phenylacetamido)piperidine-1-carboxylate. To a solution of 9H-fluoren-9-ylmethyl 4-amino-4-[(1-carbamoyl-1-methylethyl)carbamoyl]piperidine-1-carboxylate (200.0 mg, 0.444 mmol), phenylacetic acid (72.5 mg, 0.533 mmol) and DIPEA (229.5 mg, 1.776 mmol) in DMF (3.0 mL) was added HATU (219.4 mg, 0.577 mmol) at 25° C. and was stirred for 1 h at 25° C. The residue was purified by reverse phase with 0.05% TFA of water/CAN (1:1). This resulted in 223 mg (88%) of 9H-fluoren-9-ylmethyl 4-[(1-carbamoyl-1-methylethyl)carbamoyl]-4-(2-phenylacetamido)piperidine-1-carboxylate as a yellow solid. LCMS (ESI): [M+H]$^+$=569.

2-methyl-2-[[4-(2-phenylacetamido)piperidin-4-yl]formamido]propanamide. To a solution of 9H-fluoren-9-ylmethyl 4-[(1-carbamoyl-1-methylethyl)carbamoyl]-4-(2-phenylacetamido)piperidine-1-carboxylate (213.00 mg, 0.375 mmol, 1.00 equiv) in DMF (2.00 mL) was added piperidine (0.50 mL) and was stirred for 30 min at 25° C. The crude product was purified by Prep-HPLC with the following conditions (2 #SHIMADZU (HPLC-01)): Column, XBridge Prep Amide OBD Column, 150 mm 5 um 13 nm; mobile phase, Water (10 MMOL/L NH4HCO3) and ACN (95% PhaseB down to 50% in 7 min). This resulted in 27.6 mg (21%) of 2-methyl-2-[[4-(2-phenylacetamido)piperidin-4-yl]formamido]propanamide as a white solid. LCMS (ESI): [M+H]$^+$=347. $^1$H NMR (300 MHz, Methanol-$d_4$) δ 7.38-7.23 (m, 5H), 3.62 (s, 2H), 3.00-2.92 (m, 2H), 2.85-2.76 (m, 2H), 2.08-1.99 (m, 4H), 1.36 (s, 6H).

Piperidine analogs 22-38 were synthesized by following the above synthetic procedures.

2. Evaluation of Exemplary Phenyl and Heterocycloalkyl Compounds

A list of compounds evaluated is shown in Table 1 below.

TABLE 1

| No. | Structure | KD | EC50 (μM) Luci-ferase | Min/Max % Luciferase | HRMS/LCMS | $^1$H NMR (400 MHz, DMSO-d6 or MeOH-$d_4$) |
|---|---|---|---|---|---|---|
| 1 | 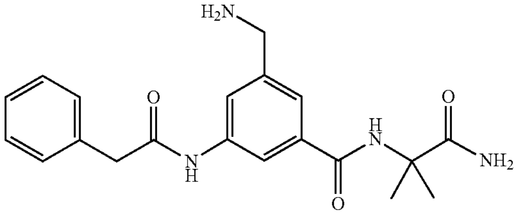 [SMILES: CC(C)(NC(=O)c1cc(CN)cc(NC(=O)Cc2ccccc2)c1)C(N)=O] | No Binding | 0.39 | Pending | m/z = 369 [M + H]$^+$ | δ 7.88-7.86 (m, 1H), 7.74-7.72 (m, 1H), 7.57-7.55 (m, 1H), 7.39-7.32 (m, 4H), 7.29-7.24 (m, 1H), 3.88 (s, 2H), 3.72 (s, 2H), 1.61 (s, 6H) |
| 2 | 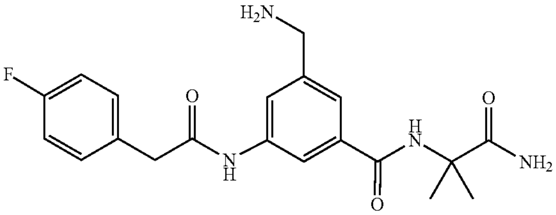 [SMILES: CC(C)(NC(=O)c1cc(CN)cc(NC(=O)Cc2ccc(F)cc2)c1)C(N)=O] | 8.60E-07 | 0.93 | 41.2/52.6 | m/z = 387 [M + H]$^+$ | δ 7.88-7.86 (m, 1H), 7.74-7.72 (m, 1H), 7.58-7.56 (m, 1H), 7.41-7.38 (m, 2H), 7.10-7.06 (m, 2H), 3.88 (s, 2H), 3.71 (s, 2H), 1.61 (s, 6H). |
| 3 | 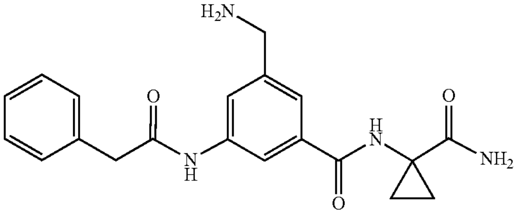 [SMILES: NCc1cc(NC(=O)Cc2ccccc2)cc(C(=O)NC2(C(N)=O)CC2)c1] | 6.70E-05 | 12.56 | Pending | m/z = 367 [M + H]$^+$ | δ 7.93 (t, J = 1.8 Hz, 1H), 7.71 (t, J = 1.8 Hz, 1H), 7.58 (t, J = 1.6 Hz, 1H), 7.43-7.22 (m, 5H), 3.85 (s, 2H), 3.72 (s, 2H), 1.62-1.52 (m, 2H), 1.21-1.10 (m, 2H). |
| 4 | 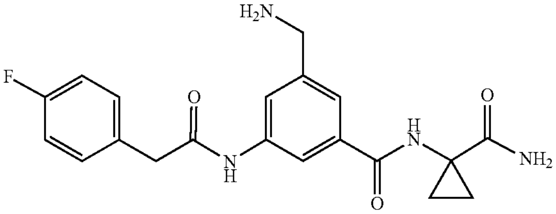 [SMILES: NCc1cc(NC(=O)Cc2ccc(F)cc2)cc(C(=O)NC2(C(N)=O)CC2)c1] | 2.40E-05 | 15.66 | 31.6/36.6 | m/z = 385 [M + H]$^+$ | δ 7.92 (t, J = 1.9 Hz, 1H), 7.72 (s, 1H), 7.59 (s, 1H), 7.39-7.35 (m, 2H), 7.07 (t, J = 8.8 Hz, 2H), 3.88 (s, 2H), 3.70 (s, 2H), 1.62-1.51 (m, 2H), 1.15-1.11 m, 2H). |
| 5 | 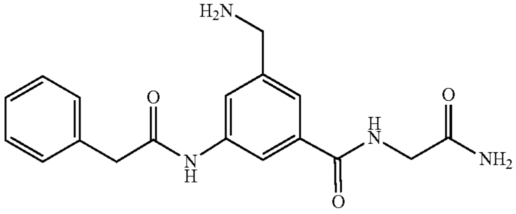 [SMILES: NCc1cc(NC(=O)Cc2ccccc2)cc(C(=O)NCC(N)=O)c1] | No Binding | 14.77 | 29.6/40.6 | m/z = 480 [M + H]$^+$ | δ 7.92 (d, J = 1.6 Hz, 2H), 7.63 (d, J = 1.7 Hz, 1H), 7.43-7.31 (m, 4H), 7.31-7.24 (m, 1H), 4.04 (d, J = 8.6 Hz, 4H), 3.73 (s, 2H). |
| 6 | 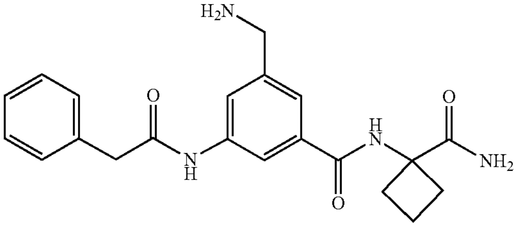 [SMILES: NCc1cc(NC(=O)Cc2ccccc2)cc(C(=O)NC2(C(N)=O)CCC2)c1] | 5.61E-06 | 27.14 | 28.9/42.88 | m/z = 381 [M + H]$^+$ | δ 7.93 (t, J = 1.9 Hz, 1H), 7.72 (t, J = 1.9 Hz, 1H), 7.61 (t, J = 1.6 Hz, 1H), 7.43-7.30 (m, 4H), 7.31-7.23 (m, 1H), 3.87 (s, 2H), 3.72 (s, 2H), 2.80-2.69 (m, 2H), 2.42-2.30 (m, 2H), 2.08-2.00 (m, 2H). |

TABLE 1-continued

| No. | Structure | KD | EC50 (μM) Luci-ferase | Min/Max % Luciferase | HRMS/ LCMS | $^1$H NMR (400 MHz, DMSO-d6 or MeOH-$d_4$) |
|---|---|---|---|---|---|---|
| 7 | 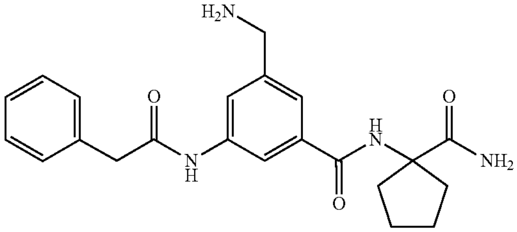 [SMILES: NCc1cc(NC(=O)Cc2ccccc2)cc(C(=O)NC2(C(N)=O)CCCC2)c1] | No Binding | 26.1 | 27.76/53.7 | m/z = 395 $[M + H]^+$ | δ 7.88 (s, 1H), 7.74 (s, 1H), 7.57 (s, 1H), 7.36-7.32 (m, 4H), 7.29-7.25 (m, 1H), 3.91 (s, 2H), 3.72 (s, 2H), 2.96-2.27 (m, 2H), 2.13-2.03 (m, 2H), 1.84-1.78 (m, 4H). |
| 8 | 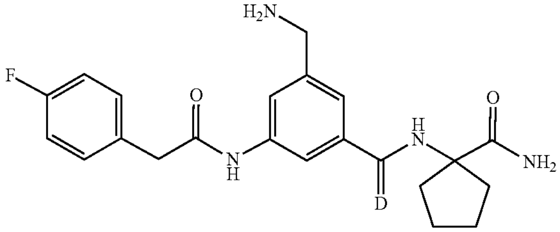 | 1.14E-04 | 63.6 | 33.9/66.18 | m/z = 413 $[M + H]^+$ | δ 11.28 (s, 1H), 9.06 (s, 1H), 8.79 (d, J = 2.2 Hz, 1H), 8.67 (t, J = 1.7 Hz, 1H), 8.45 (s, 1H), 8.24-8.14 (m, 2H), 8.03-7.93 (m, 2H), 7.78 (s, 1H), 7.64 (s, 1H), 4.82 (s, 2H), 4.48 (s, 2H), 2.99-2.88 (m, 2H), 2.84-2.80 (m, 2H), 2.52-2.43 (m, 4H). |
| 9 | 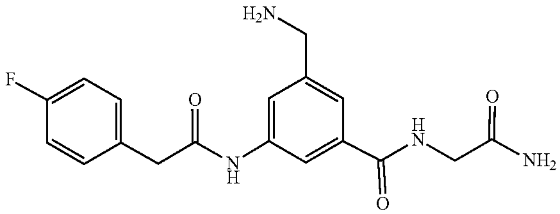 [SMILES: NCc1cc(NC(=O)Cc2ccc(F)cc2)cc(C(=O)NCC(N)=O)c1] | 6.30E-05 | 0.07 | 25.7/38.0 | m/z = 359 $[M + H]^+$ | δ 8.02 (t, J = 1.9 Hz, 1H), 7.91 (t, J = 1.8 Hz, 1H), 7.66 (t, J = 1.6 Hz, 1H), 7.44-7.34 (m, 2H), 7.15-7.02 (m, 2H), 4.15 (s, 2H), 4.06 (s, 2H), 3.72 (s, 2H). |
| 10 | 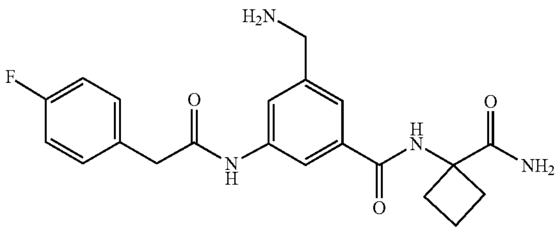 [SMILES: NCc1cc(NC(=O)Cc2ccc(F)cc2)cc(C(=O)NC2(C(N)=O)CCC2)c1] | 1.63E-06 | 7.057 | 19.8/28.2 | m/z = 399 $[M + H]^+$ | δ 10.27 (s, 1H), 8.69 (s, 1H), 7.85 (s, 1H), 7.76 (s, 1H), 7.59 (s, 1H), 7.41-7.33 (m, 2H), 7.15 (t, J = 8.9 Hz, 2H), 6.94 (s, 1H), 6.80 (s, 1H), 3.75 (s, 2H), 3.63 (s, 2H), 2.89-2.82 (m, 2H), 2.24-2.17 (m, 2H), 1.92-1.79 (m, 2H). |
| 11 | 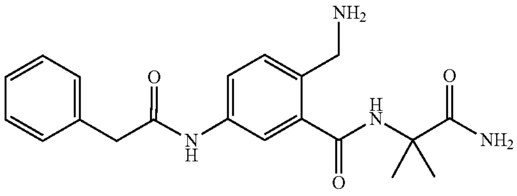 [SMILES: CC(C)(NC(=O)c1cc(NC(=O)Cc2ccccc2)ccc1CN)C(N)=O] | 1.10E-04 | 19.98 | 19.2/24.4 | m/z = 369 $[M + H]^+$ | δ 7.82 (d, J = 2.3 Hz, 1H), 7.60-7.57 (m, 1H), 7.41-7.30 (m, 5H), 7.30-7.22 (m, 1H), 3.89 (s, 2H), 3.70 (s, 2H), 1.59 (s, 6H). |
| 12 | 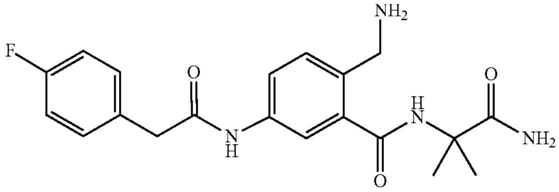 [SMILES: CC(C)(NC(=O)c1cc(NC(=O)Cc2ccc(F)cc2)ccc1CN)C(N)=O] | 1.0E-06 | 14.28 | 21.4/27.1 | m/z = 387 $[M + H]^+$ | δ 7.77 (d, J = 1.5 Hz, 1H), 7.58-7.56 (m, 1H), 7.40-7.37 (m, 3H), 7.11-7.06 (m, 2H), 3.83 (s, 2H), 3.69 (s, 2H), 1.59 (s, 6H). |

TABLE 1-continued

| No. | Structure | KD | EC50 (μM) Luci-ferase | Min/Max % Luciferase | HRMS/ LCMS | $^1$H NMR (400 MHz, DMSO-d6 or MeOH-$d_4$) |
|---|---|---|---|---|---|---|
| 13 | 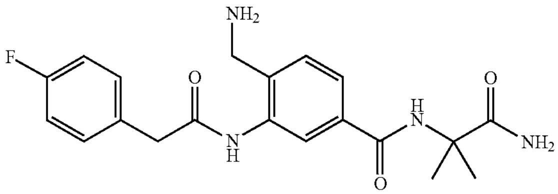 [SMILES: CC(C)(NC(=O)c1ccc(CN)c(NC(=O)Cc2ccc(F)cc2)c1)C(N)=O] | 2.50E-04 | 20.4 | 21.7/28.7 | m/z = 387 $[M + H]^+$ | δ 10.10 (s, 1H), 8.24-8.17 (m, 4H), 7.80-7.65 (m, 2H), 7.54 (d, J = 8.1 Hz, 1H), 7.42-7.37 (m, 2H), 7.21-7.15 (m, 2H), 6.90 (s, 1H), 3.96 (s, 2H), 3.73 (s, 2H), 1.46 (s, 6H). |
| 14 | 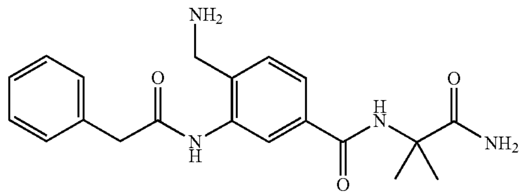 [SMILES: CC(C)(NC(=O)c1ccc(CN)c(NC(=O)Cc2ccccc2)c1)C(N)=O] | 2.47E-05 | 1.19 | 19.7/29.8 | m/z = 369 $[M + H]^+$ | δ 10.10 (s, 1H), 8.23 (s, 1H), 8.15 (s, 2H), 7.82-7.73 (m, 2H), 7.54 (d, J = 8.1 Hz, 1H), 7.40-7.31 (m, 4H), 7.28-7.27 (m, 1H), 7.19 (s, 1H), 6.90 (s, 1H), 3.95 (s, 2H), 3.73 (s, 2H), 1.46 (s, 6H). |
| 15 | 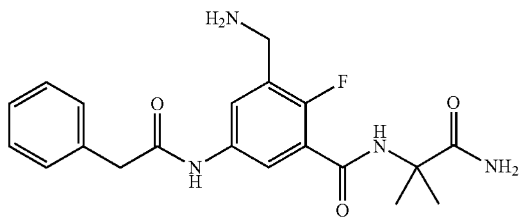 [SMILES: CC(C)(NC(=O)c1cc(NC(=O)Cc2ccccc2)cc(CN)c1F)C(N)=O] | 1.03E-05 | 19.3 | 14.6/36.6 | m/z = 387 $[M + H]^+$ | δ 10.32 (s, 1H), 8.24 (d, J = 6.6 Hz, 1H), 7.82 (d, J = 6.3 Hz, 2H), 7.34-7.14 (m, 7H), 3.76 (s, 2H), 3.62 (s, 3H), 1.50 (s, 6H). |
| 16 | 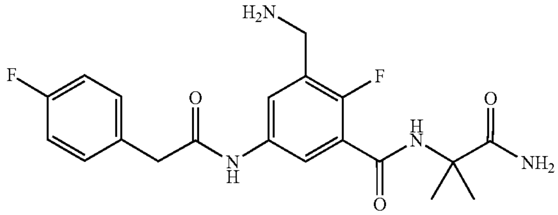 [SMILES: CC(C)(NC(=O)c1cc(NC(=O)Cc2ccc(F)cc2)cc(CN)c1F)C(N)=O] | No Binding | 20.6 | 16.1/21.6 | m/z = 405 $[M + H]^+$ | δ 10.32 (s, 1H), 8.25 (d, J = 6.0 Hz, 1H), 7.82 (d, J = 2.4 Hz, 2H), 7.36 (t, J = 6.5 Hz, 2H), 7.27 (s, 1H), 7.21-7.09 (m, 3H), 3.77 (s, 2H), 3.62 (s, 2H), 1.50 (s, 6H). |
| 17 | 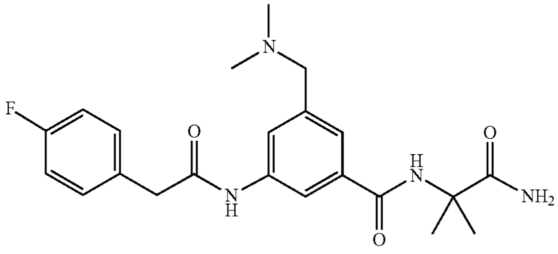 [SMILES: CN(C)Cc1cc(NC(=O)Cc2ccc(F)cc2)cc(C(=O)NC(C)(C)C(N)=O)c1] | 6.84E-05 | 0.21 | 13.1/20.1 | m/z = 415 $[M + H]^+$ | δ 7.94 (t, J = 1.8 Hz, 1H), 7.67 (d, J = 1.6 Hz, 1H), 7.54 (s, 1H), 7.41-7.39 (m, 2H), 7.10-7.06 (m, 2H), 3.70 (s, 2H), 3.51 (s, 2H), 2.27 (s, 6H), 1.60 (s, 6H). |
| 18 | 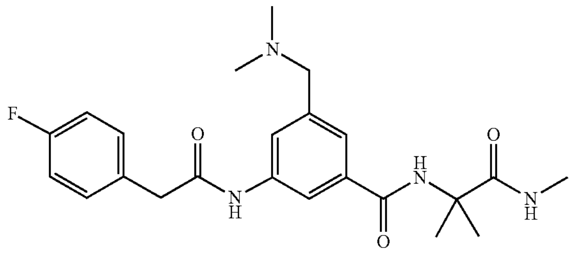 [SMILES: CNC(=O)C(C)(C)NC(=O)c1cc(CN(C)C)cc(NC(=O)Cc2ccc(F)cc2)c1] | No Binding | 21.04 | 17.9/24.67 | m/z = 429 $[M + H]^+$ | δ 7.94 (t, J = 1.8 Hz, 1H), 7.66 (s, 1H), 7.54 (s, 1H), 7.71-7.36 (m, 2H), 7.10-7.04 (m, 2H), 3.70 (s, 2H), 3.54 (s, 2H), 2.76 (s, 3H), 2.29 (s, 6H), 1.56 (s, 6H). |

TABLE 1-continued

| No. | Structure | KD | EC50 (μM) Luci-ferase | Min/Max % Luciferase | HRMS/ LCMS | $^1$H NMR (400 MHz, DMSO-d6 or MeOH-$d_4$) |
| --- | --- | --- | --- | --- | --- | --- |
| 19 | 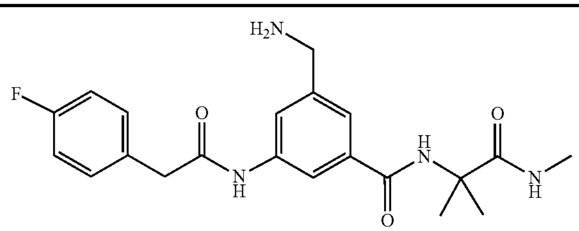 | 1.24E-06 | 20.7 | 18.7/26.8 | m/z = 401 $[M + H]^+$ | δ 7.87 (t, J = 1.8 Hz, 1H), 7.71 (s, 1H), 7.57 (s, 1H), 7.42-7.37 (m, 2H), 7.11-7.05 (m, 2H), 3.87 (s, 2H), 3.71 (s, 2H), 2.75 (s, 3H), 1.57 (s, 6H). |
| 20 | 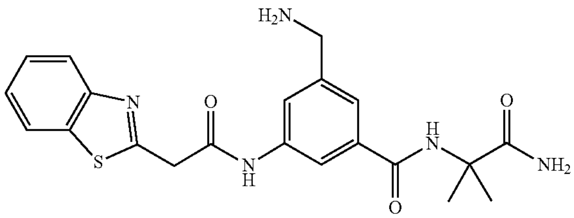 [SMILES: CC(C)(NC(=O)c1cc(CN)cc(NC(=O)Cc2nc3ccccc3s2)c1)C(N)=O] | | | | m/z = 426 $[M + H]^+$ | δ 8.01-7.96 (m, 3H), 7.93 (s, 1H), 7.63 (s, 1H), 7.56-7.50 (m, 1H), 7.47-7.42 (m, 1H), 4.83 (s, 2H), 4.16 (s, 2H), 1.61 (s, 6H) |
| 21 | 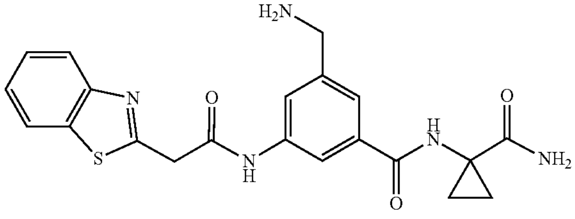 [SMILES: NCc1cc(NC(=O)Cc2nc3ccccc3s2)cc(C(=O)NC2(C(N)=O)CC2)c1] | | | | m/z = 424 $[M + H]^+$ | δ 8.03-7.97 (m, 4H), 7.70 (s, 1H), 7.57-7.52 (m, 1H), 7.49-7.45 (m, 1H), 4.89 (s, 2H), 4.14 (s, 2H), 1.58 (d, J = 3.2 Hz, 2H), 1.18 (t, J = 3.8 Hz, 2H). |
| 22 | 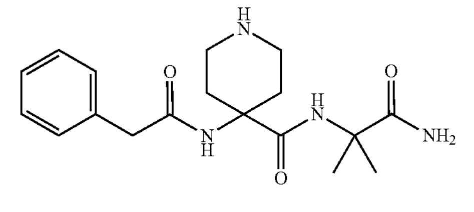 [SMILES: CC(C)(NC(=O)C1(NC(=O)Cc2ccccc2)CCNCC1)C(N)=O] | 6.53E-06 | 4.22 | 28.67/44.58 | m/z = 347.2 $[M + H]^+$ | δ 7.38-7.23 (m, 5H), 3.62 (s, 2H), 3.00-2.92(m, 2H), 2.85-2.76 (m, 2H), 2.08-1.99 (m, 4H), 1.36 (s, 6H). |
| 23 | 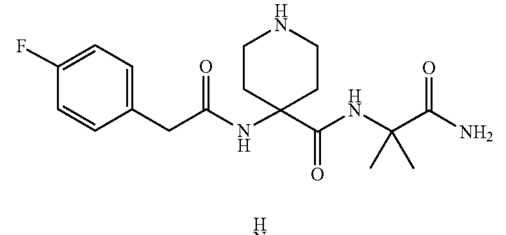 | 9.00E-06 | 9.02 | 26.13/34.93 | m/z = 365.2 $[M + H]^+$ | δ 7.38-7.33 (m, 2H), 7.19-7.03 (m, 2H), 3.61 (s, 2H), 2.99-2.93 (m, 2H), 2.86-2.77 (m, 2H), 2.08-1.96 (m, 4H), 1.39 (s, 6H). |
| 24 | 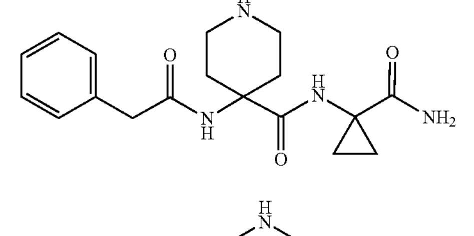 | 1.90E-05 | 7.73 | 32.88/47.58 | m/z = 345.25 $[M + H]^+$ | δ 7.35-7.23 (m, 5H), 3.64 (s, 2H), 2.97-2.91 (m, 2H), 2.82-2.76 (m, 2H), 2.03-1.89 (m, 4H), 1.47-1.44 (m, 2H), 0.99-0.95 (m, 2H). |
| 25 | 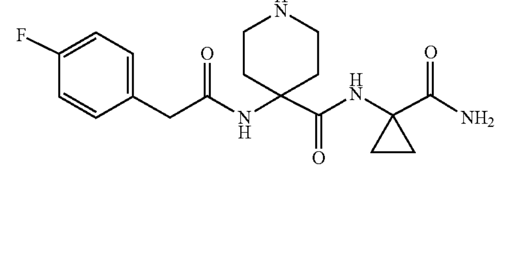 | 5.55E-05 | 0.36 | 30.43/46.70 | m/z = 363.25 $[M + H]^+$ | δ 7.35-7.31 (m, 2H), 7.08-7.02 (m, 2H), 3.62 (s, 2H), 2.93-2.87 (m, 2H), 2.79-2.71 (m, 2H), 2.00-1.86 (m, 4H), 1.48-1.45 (m, 2H), 0.99-0.96 (m, 2H). |

TABLE 1-continued
| No. | Structure | KD | EC50 (μM) Luci-ferase | Min/Max % Luciferase | HRMS/ LCMS | $^1$H NMR (400 MHz, DMSO-d6 or MeOH-$d_4$) |
| --- | --- | --- | --- | --- | --- | --- |
| 26 | 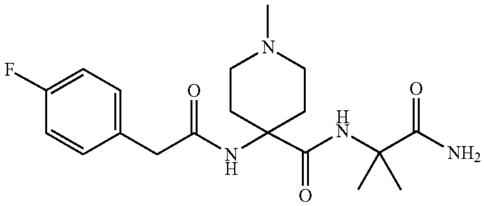 [SMILES: CN1CCC(NC(=O)Cc2ccc(F)cc2)(C(=O)NC(C)(C)C(N)=O)CC1] | | | | m/z = 379 $[M + H]^+$ | δ 7.39-7.34 (m, 2H), 7.11-7.04 (m, 2H), 3.60 (s, 2H), 2.77-2.70 (m, 2H), 2.35-2.28 (m, 5H), 2.18-2.00 (m, 4H), 1.42 (s, 6H). |
| 27 | 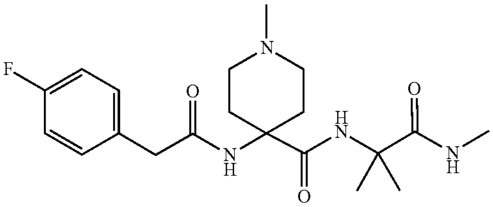 [SMILES: CNC(=O)C(C)(C)NC(=O)C1(NC(=O)Cc2ccc(F)cc2)CCN(C)CC1] | | | | m/z = 393 $[M + H]^+$ | δ 7.37-7.32 (m, 2H), 7.09-7.02 (m, 2H), 3.59 (s, 2H), 2.70-2.64 (m, 2H), 2.59 (s, 3H), 2.60 (s, 5H), 2.13-1.97 (m, 4H), 1.34 (s, 6H). |
| 28 | 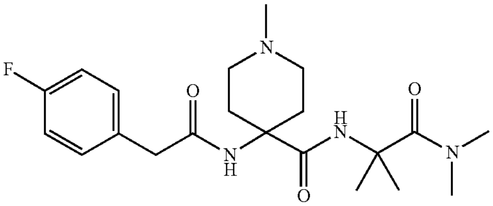 [SMILES: CN1CCC(NC(=O)Cc2ccc(F)cc2)(C(=O)NC(C)(C)C(=O)N(C)C)CC1] | | | | m/z = 407 $[M + H]^+$ | δ 7.37-7.33 (m, 1H), 7.09-7.03 (m, 2H), 3.55 (s, 2H), 2.93 (s, 6H), 2.66 (d, J = 11.4 Hz, 2H), 2.26 (s, 3H), 2.22-2.04 (m, 6H), 1.38 (s, 6H). |
| 29 | 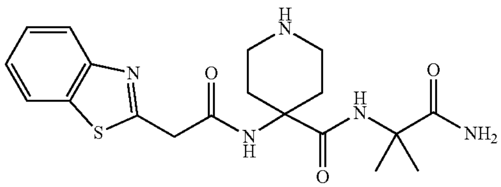 [SMILES: CC(C)(NC(=O)C1(NC(=O)Cc2nc3ccccc3s2)CCNCC1)C(N)=O] | | | | m/z = 404 $[M + H]^+$ | δ 8.50 (s, 1H), 8.07-8.05 (m, 1H), 7.95-7.93 (m, 1H), 7.52-7.39 (m, 3H), 6.85 (s, 1H), 6.79 (s, 1H), 4.20 (s, 2H), 2.73 (s, 4H), 1.79 (s, 4H), 1.30 (s, 6H). |
| 30 | 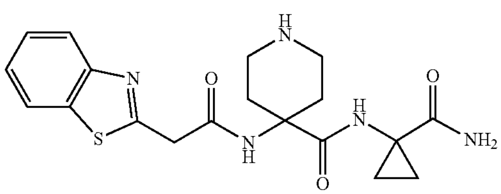 [SMILES: NC(=O)C1(NC(=O)C2(NC(=O)Cc3nc4ccccc4s3)CCNCC2)CC1] | | | | m/z = 402 $[M + H]^+$ | δ 7.99-7.92 (m, 2H), 7.56-7.42 (m, 2H), 4.70 (s, 2H), 3.12-3.07 (m, 2H), 3.03-2.91 (m, 2H), 2.04-1.93 (m, 4H), 1.44-1.34 (m, 2H), 1.08-0.97 (m, 2H). |
| 31 | 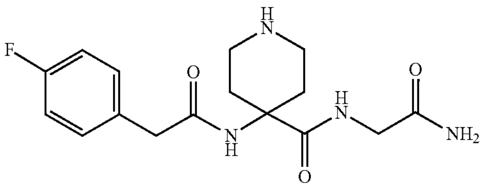 [SMILES: NC(=O)CNC(=O)C1(NC(=O)Cc2ccc(F)cc2)CCNCC1] | | | | m/z = 337 $[M + H]^+$ | δ 7.34-7.29 (m, 2H), 7.06-7.00 (m, 2H), 3.77 (s, 2H), 3.61 (s, 2H), 2.97-2.93 (m, 2H), 2.83-2.74 (m, 2H), 2.05-1.99 (m, 4H). |
| 32 | 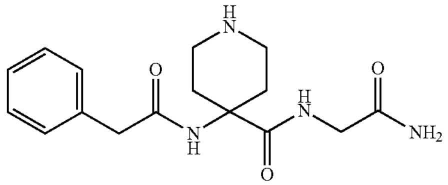 [SMILES: NC(=O)CNC(=O)C1(NC(=O)Cc2ccccc2)CCNCC1] | | | | m/z = 319 $[M + H]^+$ | δ 7.52-7.25 (m, 5H), 3.79 (s, 2H), 3.64 (s, 2H), 3.00-2.89 (m, 2H), 2.83-2.71 (m, 2H), 2.14-1.91 (m, 4H) |

TABLE 1-continued
| No. | Structure | KD | EC50 (μM) Luci-ferase | Min/Max % Luciferase | HRMS/ LCMS | $^1$H NMR (400 MHz, DMSO-d6 or MeOH-$d_4$) |
|---|---|---|---|---|---|---|
| 33 | 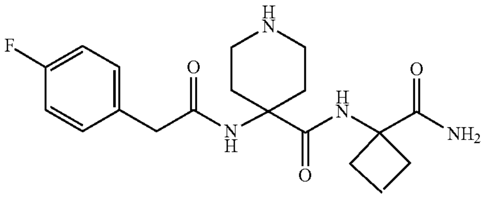 | | | | m/z = 377 $[M + H]^+$ | δ 7.29-7.26 (m, 2H), 7.09-7.04 (m, 2H), 3.60 (s, 2H), 2.98-2.92 (m, 2H), 2.81-2.74 (m, 2H), 2.48-2.2.41 (m, 2H), 2.06-1.77 (m, 8H). |
| 34 | 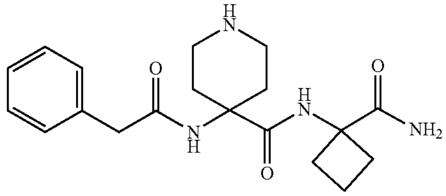 [SMILES: NC(=O)C1(NC(=O)C2(NC(=O)Cc3ccccc3)CCNCC2)CCC1] | | | | m/z = 351 $[M + H]^+$ | δ 7.37-7.24 (m, 5H), 3.63 (s, 2H), 3.01-2.85 (m, 2H), 2.84-2.80 (m, 2H), 2.64-2.57 (m, 2H), 2.16-2.06 (m, 8H). |
| 35 | 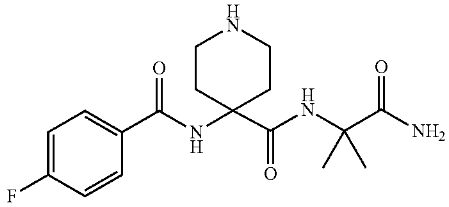 [SMILES: CC(C)(NC(=O)C1(NC(=O)c2ccc(F)cc2)CCNCC1)C(N)=O] | | | | m/z = 351 $[M + H]^+$ | δ 8.00-7.94 (m, 2H), 7.28-7.21 (m, 2H), 3.16-2.99 (m, 4H), 2.27-2.15 (m, 4H), 1.49 (s, 6H) |
| 36 | 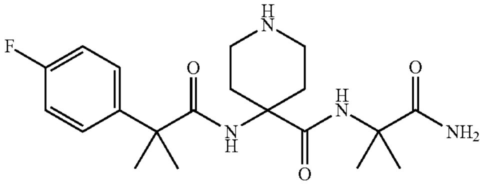 [SMILES: CC(C)(NC(=O)C1(NC(=O)C(C)(C)c2ccc(F)cc2)CCNCC1)C(N)=O] | | | | m/z = 393 $[M + H]^+$ | δ 7.50-7.45 (m, 2H), 7.16-7.10 (m, 2H), 2.96-2.89 (m, 2H), 2.63-2.54 (m, 2H), 2.05-1.93 (m, 4H), 1.61 (s, 6H), 1.47 (s, 6H). |
| 37 | 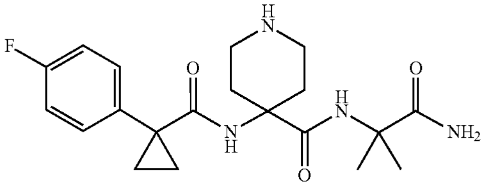 [SMILES: CC(C)(NC(=O)C1(NC(=O)C2(c3ccc(F)cc3)CC2)CCNCC1)C(N)=O] | | | | m/z = 391 $[M + H]^+$ | δ 7.61-7.55 (m, 2H), 7.21-7.15 (m, 2H), 2.88-2.81 (m, 2H), 2.43-2.33 (m, 2H), 1.94-1.80 (m, 4H), 1.51-1.47 (m, 2H), 1.46 (s, 6H), 1.15-1.11 (m, 2H). |
| 38 | 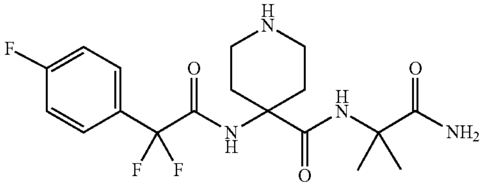 [SMILES: CC(C)(NC(=O)C1(NC(=O)C(F)(F)c2ccc(F)cc2)CCNCC1)C(N)=O] | | | | m/z = 401 $[M + H]^+$ | δ 7.73-7.68 (m, 2H), 7.26-7.21 (m, 2H), 2.98-2.91 (m, 2H), 2.82-2.73 (m, 2H), 2.12-1.98 (m, 4H), 1.38 (s, 6H). |

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula selected from:

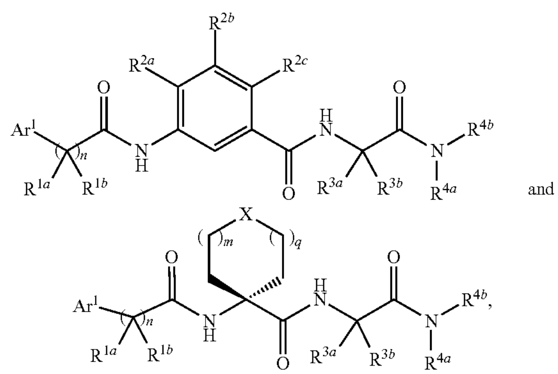

and wherein each of n, m, and q, when present, is independently selected from 0 and 1;

wherein X, when present, is selected from —O—, —S—, and —$NR^{10}$—;

wherein $R^{10}$, when present, is selected from hydrogen, methyl, ethyl, n-propyl, isopropyl, n-butyl, isobutyl, s-butyl, and t-butyl;

wherein each of $R^{1a}$ and $R^{1b}$, when present, is independently selected from hydrogen, halogen, methyl, ethyl, n-propyl, isopropyl, n-butyl, isobutyl, s-butyl, and t-butyl;

or wherein each of $R^{1a}$ and $R^{1b}$, when present, together comprise a $C_3$-$C_6$ cycloalkyl;

wherein each of $R^{2a}$, $R^{2b}$, and $R^{2c}$, when present, is independently selected from hydrogen, halogen, and —$CH_2NR^{11a}R^{11b}$, provided that at least one of $R^{2a}$, $R^{2b}$, and $R^{2c}$ is —$CH_2NR^{11a}R^{11b}$;

wherein each of $R^{11a}$ and $R^{11b}$, when present, is independently selected from hydrogen, methyl, ethyl, n-propyl, isopropyl, n-butyl, isobutyl, s-butyl, and t-butyl;

wherein each of $R^{3a}$ and $R^{3b}$ is independently selected from hydrogen, methyl, ethyl, n-propyl, isopropyl, n-butyl, isobutyl, s-butyl, and t-butyl, or wherein each of $R^{3a}$ and $R^{3b}$ together comprise a C3-C6 cycloalkyl;

wherein each of $R^{4a}$ and $R^{4b}$ is independently selected from hydrogen, methyl, ethyl, n-propyl, isopropyl, n-butyl, isobutyl, s-butyl, and t-butyl; and wherein $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4) (C1-C4) dialkylamino, and C1-C4 aminoalkyl, or a pharmaceutically acceptable salt thereof.

2. The compound of claim 1, wherein n is 1.

3. The compound of claim 1, wherein each of $R^{1a}$ and $R^{1b}$, when present, is hydrogen.

4. The compound of claim 1, wherein each of $R^{1a}$ and $R^{1b}$, when present, is selected from methyl, ethyl, n-propyl, isopropyl, n-butyl, isobutyl, s-butyl, and t-butyl.

5. The compound of claim 1, wherein each of $R^{1a}$ and $R^{1b}$, when present, is halogen.

6. The compound of claim 1, wherein each of $R^{1a}$ and $R^{1b}$, when present, together comprise a C3-C6 cycloalkyl.

7. The compound of claim 1, wherein two of $R^{2a}$, $R^{2b}$, and $R^{2c}$, when present, are hydrogen.

8. The compound of claim 1, wherein each of $R^{3a}$ and $R^{3b}$ is independently selected from hydrogen, methyl, ethyl, n-propyl, isopropyl, n-butyl, isobutyl, s-butyl, and t-butyl.

9. The compound of claim 1, wherein each of $R^{3a}$ and $R^{3b}$ together comprise a C3-C6 cycloalkyl.

10. The compound of claim 1, wherein $Ar^1$ is C6-C14 aryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4) (C1-C4) dialkylamino, and C1-C4 aminoalkyl.

11. The compound of claim 1, wherein $Ar^1$ is C2-C10 heteroaryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

12. The compound of claim 1, wherein the compound has a structure represented by a formula:

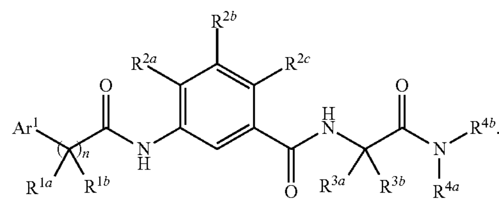

13. The compound of claim 12, wherein the compound is selected from:

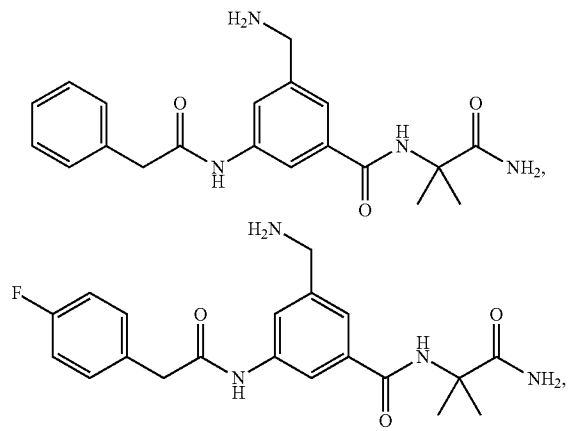

-continued
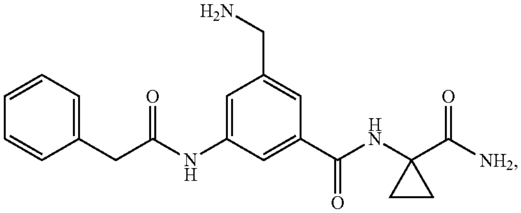
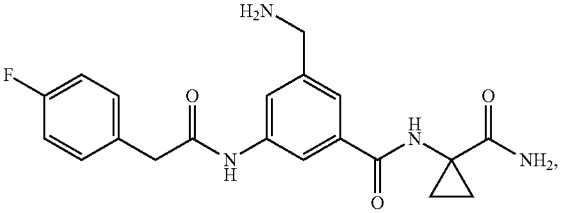
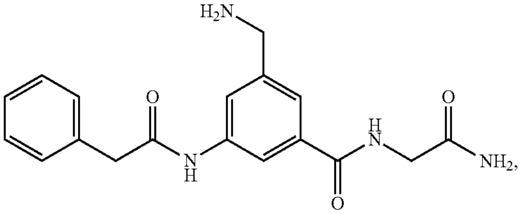
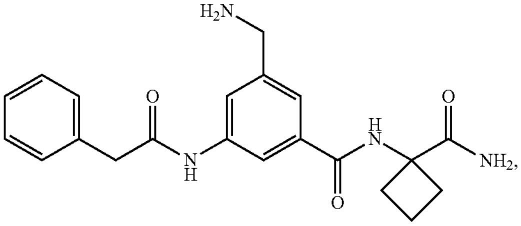
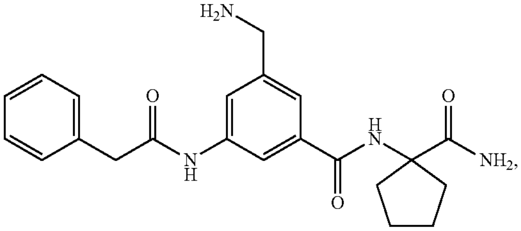
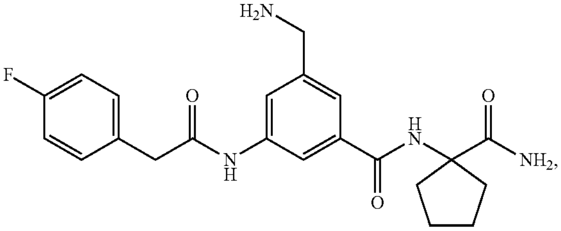
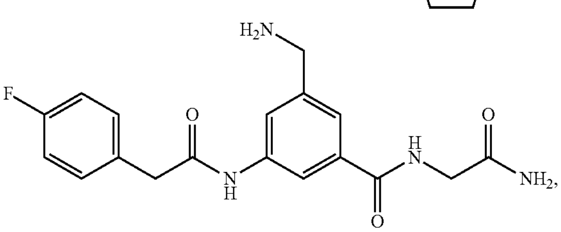
-continued
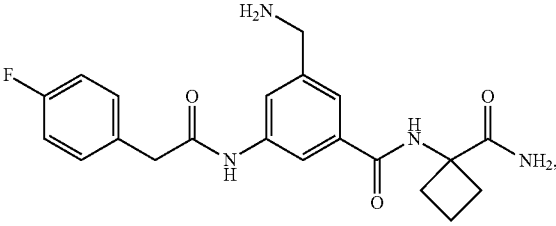
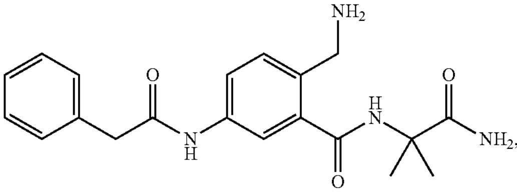
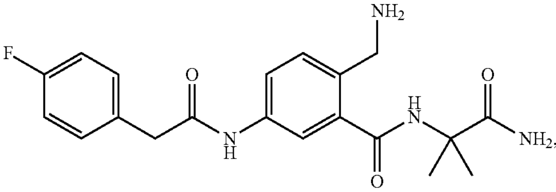
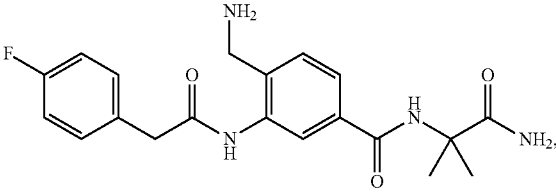
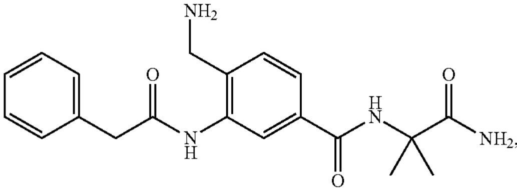
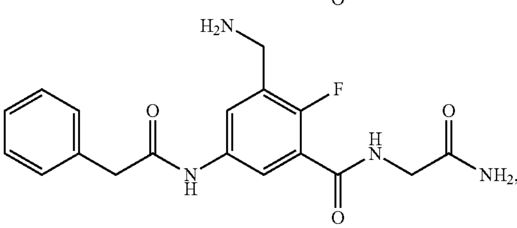
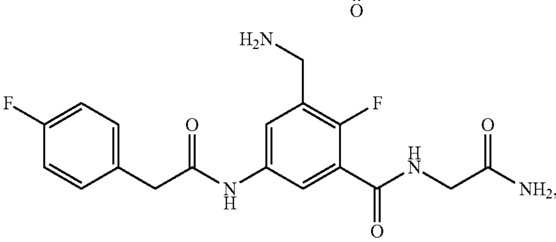
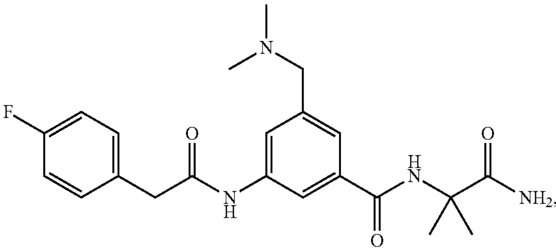

-continued

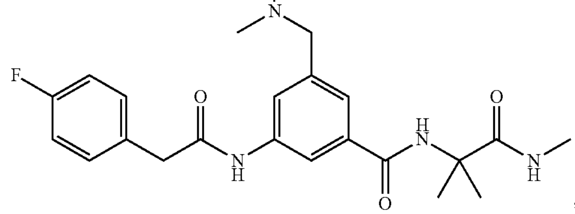

,

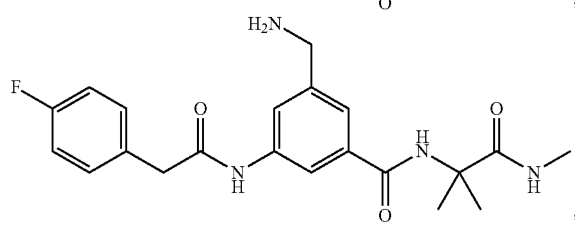

,

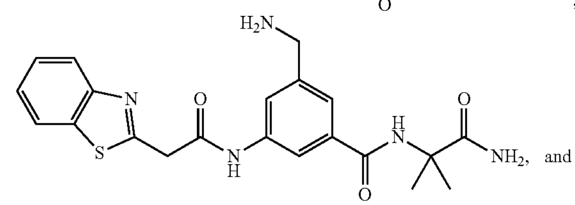

and

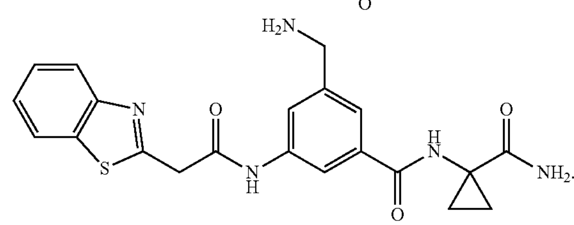

14. The compound of claim 1, wherein the compound has a structure represented by a formula:

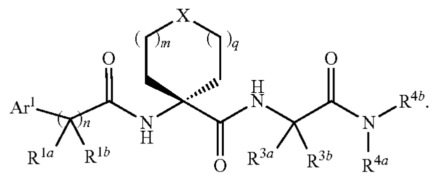

15. The compound of claim 1, wherein the compound has a structure represented by a formula:

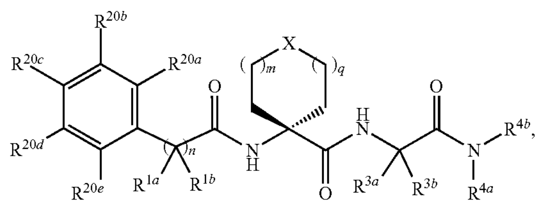

wherein each of $R^{20a}$, $R^{20b}$, $R^{20c}$, $R^{20d}$, and $R^{20e}$, is independently selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4) (C1-C4) dialkylamino, and C1-C4 aminoalkyl.

16. The compound of claim 15, wherein the compound is selected from:

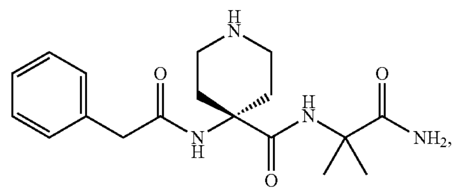

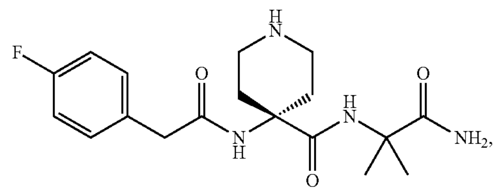

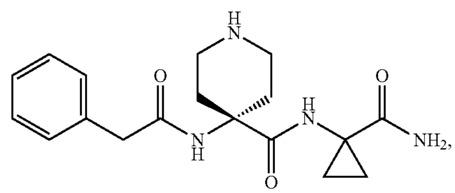

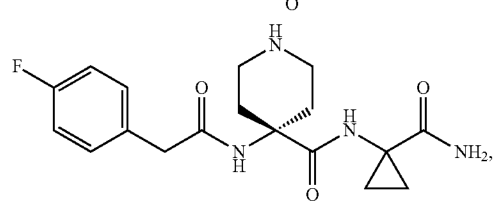

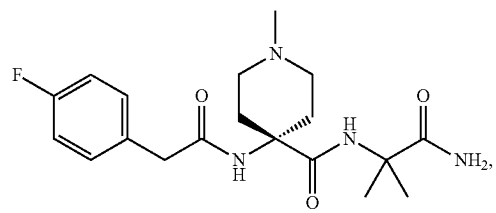

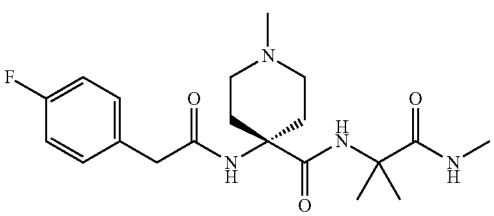

,

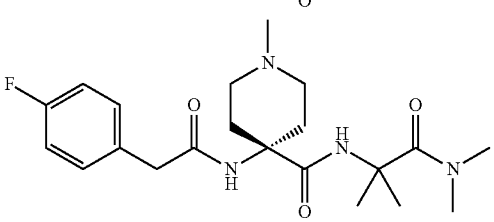

,

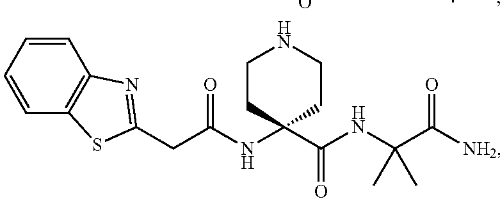

-continued
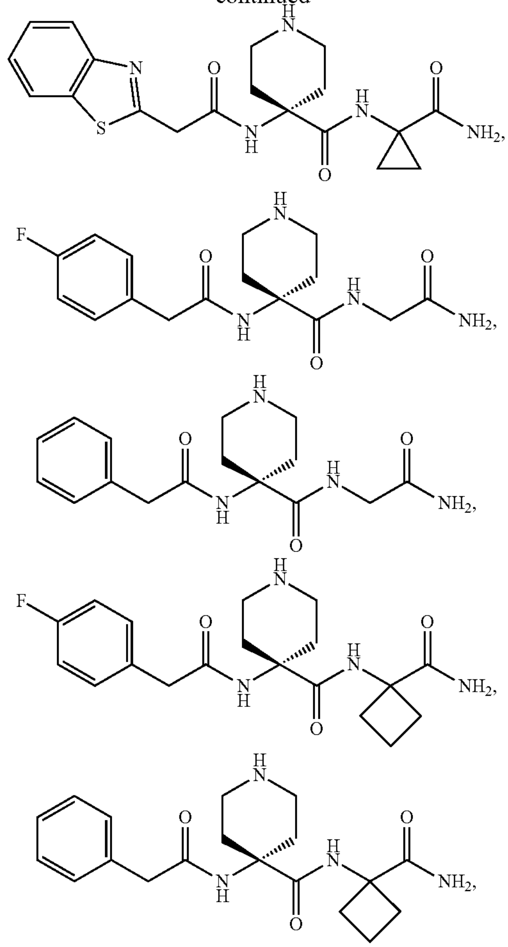
-continued
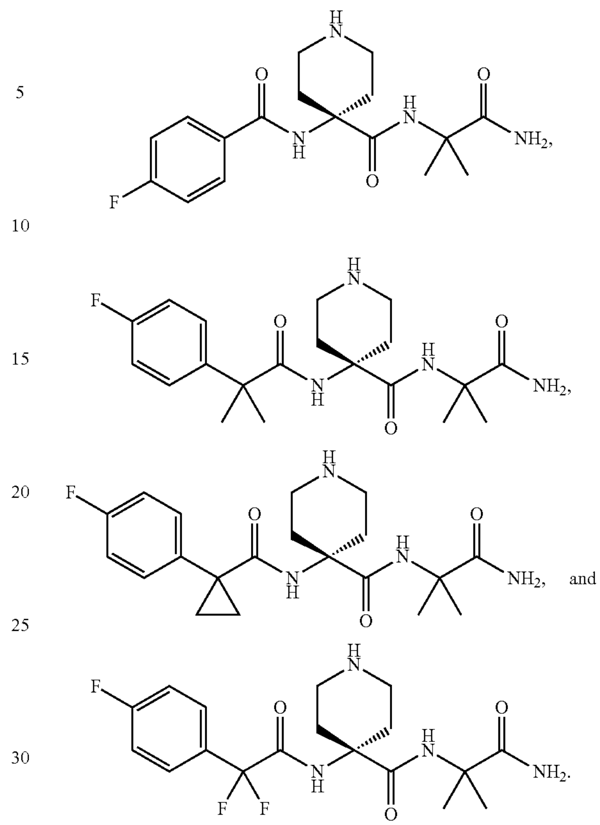
and
17. A pharmaceutical composition comprising the compound of claim 1, and a pharmaceutically acceptable carrier.
* * * * *